(12) United States Patent
Carson et al.

(10) Patent No.: US 8,729,088 B2
(45) Date of Patent: May 20, 2014

(54) TOLL-LIKE RECEPTOR MODULATORS AND TREATMENT OF DISEASES

(75) Inventors: Dennis A. Carson, La Jolla, CA (US); Howard B. Cottam, Escondido, CA (US); Tomoko Hayashi, San Diego, CA (US); Michael Chan, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 342 days.

(21) Appl. No.: 12/704,343

(22) Filed: Feb. 11, 2010

(65) Prior Publication Data

US 2010/0210598 A1 Aug. 19, 2010

Related U.S. Application Data

(60) Provisional application No. 61/151,737, filed on Feb. 11, 2009.

(51) Int. Cl.
*A61K 31/52* (2006.01)
*C07D 473/00* (2006.01)

(52) U.S. Cl.
USPC ........................................ 514/263.2; 544/276

(58) Field of Classification Search
USPC ......................... 514/263.37, 263.21; 544/276
See application file for complete search history.

(56) References Cited

U.S. PATENT DOCUMENTS

| | | | |
|---|---|---|---|
| 4,689,338 A | 8/1987 | Gerster | |
| 4,929,624 A | 5/1990 | Gerster et al. | |
| 4,938,949 A | 7/1990 | Borch et al. | |
| 5,037,986 A | 8/1991 | Gerster | |
| 5,175,296 A | 12/1992 | Gerster | |
| 5,238,944 A | 8/1993 | Wick et al. | |
| 5,352,784 A | 10/1994 | Nikolaides et al. | |
| 5,367,076 A | 11/1994 | Gerster | |
| 5,395,937 A | 3/1995 | Nikolaides et al. | |
| 5,444,065 A | 8/1995 | Nikolaides et al. | |
| 5,624,677 A | 4/1997 | El-Rashidy et al. | |
| 5,627,281 A | 5/1997 | Nikolaides et al. | |
| 5,648,516 A | 7/1997 | Nikolaides et al. | |
| 5,693,811 A | 12/1997 | Lindstrom | |
| 5,736,553 A | 4/1998 | Wick et al. | |
| 5,741,908 A | 4/1998 | Gerster et al. | |
| 5,998,619 A | 12/1999 | Gerster et al. | |
| 6,038,505 A | 3/2000 | Probst et al. | |
| 6,039,969 A | 3/2000 | Tomai et al. | |
| 6,083,505 A | 7/2000 | Miller et al. | |
| 6,150,523 A | 11/2000 | Gerster et al. | |
| 6,200,592 B1 | 3/2001 | Tomai et al. | |
| 6,245,776 B1 | 6/2001 | Skwierczynski et al. | |
| 6,329,381 B1 | 12/2001 | Kurimoto et al. | |
| 6,333,331 B1 | 12/2001 | Moschel et al. | |
| 6,372,725 B1 | 4/2002 | Zilch et al. | |
| 6,437,131 B1 | 8/2002 | Gerster et al. | |
| 6,486,168 B1 | 11/2002 | Skwierczynski et al. | |
| 6,534,654 B2 | 3/2003 | Gerster et al. | |
| 6,552,192 B1 | 4/2003 | Hans et al. | |
| 6,610,319 B2 | 8/2003 | Tomai et al. | |
| 6,613,902 B2 | 9/2003 | Gerster et al. | |
| 6,624,305 B2 | 9/2003 | Gerster | |
| 6,696,076 B2 | 2/2004 | Tomai et al. | |
| 6,706,728 B2 | 3/2004 | Hedenstrom et al. | |
| 6,716,840 B2 | 4/2004 | Chu et al. | |
| 6,733,764 B2 | 5/2004 | Martin | |
| 6,734,187 B1 | 5/2004 | Ono et al. | |
| 6,897,314 B2 | 5/2005 | Gerster et al. | |
| 6,960,582 B2 | 11/2005 | Boyce et al. | |
| 7,001,609 B1 | 2/2006 | Matson et al. | |
| 7,157,465 B2 | 1/2007 | Isobe et al. | |
| 7,189,727 B2 | 3/2007 | Boyce et al. | |
| 7,238,700 B2 | 7/2007 | Palle et al. | |

(Continued)

FOREIGN PATENT DOCUMENTS

AU 2006283524 B2 3/2013
AU 2008227128 B2 3/2013

(Continued)

OTHER PUBLICATIONS

Aromatic Ions (Chemgapedia), <http://www.chemgapedia.de/vsengine/vlu/vsc/en/ch/12/oc/vlu_organik/aromaten/aromaten/aromaten_gesamtvlu/Page/vsc/en/ch/12/oc/aromaten/aromaten/ar_ionen/ar_ionen.vscml.html> dowloaded from the internet Dec. 3, 2012.*
"U.S. Appl. No. 12/027,960, Non Final Office Action mailed Apr. 10, 2012", 16 pgs.
"U.S. Appl. No. 12/027,960, Preliminary Amendment mailed Dec. 8, 2010", 21 pgs.
"U.S. Appl. No. 12/027,960, Response filed Oct. 24, 2011 to Restriction Requirement mailed Sep. 23, 2011", 21 pgs.
"U.S. Appl. No. 12/027,960, Restriction Requirement mailed Sep. 23, 2011", 9 pgs.
"U.S. Appl. No. 12/064,529, Non Final Office Action mailed Apr. 9, 2012", 15 pgs.
"U.S. Appl. No. 12/064,529, Response filed Oct. 24, 2011 to Restriction Requirement mailed Aug. 24, 2011", 9 pgs.

(Continued)

*Primary Examiner* — Noble Jarrell
*Assistant Examiner* — Laura Daniel
(74) *Attorney, Agent, or Firm* — Schwegman, Lundberg & Woessner, P.A.

(57) ABSTRACT

Provided herein are small molecule conjugates that are agonists or antagonists of one or more toll-like receptors. For example, such conjugates include a structure according to Formula I:

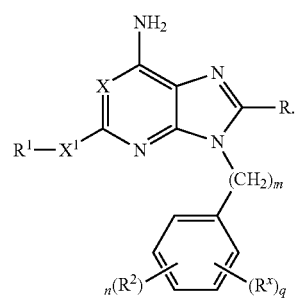

(Formula I)

18 Claims, 21 Drawing Sheets

(56) References Cited

U.S. PATENT DOCUMENTS

| | | |
|---|---|---|
| 7,241,890 B2 | 7/2007 | Kasibhatla et al. |
| 7,521,454 B2 | 4/2009 | Isobe et al. |
| 7,576,068 B2 | 8/2009 | Averett |
| 7,754,728 B2 * | 7/2010 | Isobe et al. ............... 514/263.2 |
| 7,968,544 B2 * | 6/2011 | Graupe et al. ............. 514/234.2 |
| 8,211,863 B2 | 7/2012 | Averett |
| 8,357,374 B2 | 1/2013 | Carson et al. |
| 2002/0127224 A1 | 9/2002 | Chen |
| 2002/0193595 A1 | 12/2002 | Chu et al. |
| 2003/0187261 A1 | 10/2003 | Havlicek et al. |
| 2003/0191086 A1 | 10/2003 | Hanus et al. |
| 2004/0023211 A1 | 2/2004 | Groen et al. |
| 2004/0132748 A1 | 7/2004 | Isobe et al. |
| 2004/0202663 A1 | 10/2004 | Hu et al. |
| 2004/0209899 A1 | 10/2004 | Palle et al. |
| 2004/0248895 A1 | 12/2004 | Chu et al. |
| 2004/0265351 A1 | 12/2004 | Miller et al. |
| 2005/0004144 A1 | 1/2005 | Carson et al. |
| 2005/0038027 A1 | 2/2005 | Boyce |
| 2005/0049263 A1 | 3/2005 | Kasibhatla et al. |
| 2005/0054590 A1 | 3/2005 | Averett |
| 2005/0059613 A1 | 3/2005 | Memarzadeh et al. |
| 2005/0266067 A1 | 12/2005 | Sengupta et al. |
| 2006/0052403 A1 | 3/2006 | Isobe et al. |
| 2006/0110746 A1 | 5/2006 | Andre et al. |
| 2007/0037832 A1 | 2/2007 | Isobe et al. |
| 2007/0087009 A1 | 4/2007 | Burdin |
| 2007/0100146 A1 | 5/2007 | Dzwiniel |
| 2007/0161582 A1 | 7/2007 | Mijikovic et al. |
| 2007/0173483 A1 | 7/2007 | Kasibhatla et al. |
| 2007/0190071 A1 | 8/2007 | Kurimoto et al. |
| 2007/0292418 A1 | 12/2007 | Fields et al. |
| 2008/0008682 A1 | 1/2008 | Chong et al. |
| 2008/0125446 A1 | 5/2008 | Kasibhatla et al. |
| 2008/0214580 A1 | 9/2008 | Neagu et al. |
| 2009/0047249 A1 | 2/2009 | Graupe et al. |
| 2009/0053186 A1 | 2/2009 | Hu et al. |
| 2009/0069289 A1 | 3/2009 | Neagu et al. |
| 2009/0099212 A1 | 4/2009 | Zablocki et al. |
| 2009/0105212 A1 | 4/2009 | Isobe et al. |
| 2009/0118263 A1 * | 5/2009 | Hashimoto et al. .......... 514/218 |
| 2009/0202484 A1 | 8/2009 | Chong et al. |
| 2009/0202626 A1 | 8/2009 | Carson et al. |
| 2009/0324551 A1 | 12/2009 | Carson et al. |
| 2011/0098248 A1 * | 4/2011 | Halcomb et al. .............. 514/64 |
| 2011/0098294 A1 | 4/2011 | Carson et al. |
| 2011/0319442 A1 | 12/2011 | Leoni et al. |
| 2012/0003298 A1 * | 1/2012 | Barberis et al. ............. 424/450 |
| 2012/0009247 A1 * | 1/2012 | Maj et al. ................... 424/450 |
| 2012/0083473 A1 * | 4/2012 | Holldack et al. ............. 514/150 |
| 2012/0148660 A1 * | 6/2012 | Carson et al. ................ 424/450 |
| 2012/0177681 A1 | 7/2012 | Singh et al. |
| 2013/0156807 A1 | 6/2013 | Carson et al. |
| 2013/0165455 A1 | 6/2013 | Carson et al. |
| 2013/0190494 A1 | 7/2013 | Carson et al. |

FOREIGN PATENT DOCUMENTS

| | | |
|---|---|---|
| AU | 2009210655 B2 | 8/2013 |
| CN | 101304748 A | 11/2008 |
| EP | 0145340 A2 | 6/1985 |
| EP | 0310950 A1 | 4/1989 |
| EP | 0389302 A1 | 9/1990 |
| EP | 0394026 A1 | 10/1990 |
| EP | 0553202 A1 | 8/1993 |
| EP | 0575549 A1 | 12/1993 |
| EP | 0636031 A1 | 2/1995 |
| EP | 0681570 A1 | 11/1995 |
| EP | 0708773 A1 | 5/1996 |
| EP | 0912564 A1 | 5/1999 |
| EP | 0912565 A1 | 5/1999 |
| EP | 0938315 A1 | 9/1999 |
| EP | 1035123 A1 | 9/2000 |
| EP | 1550662 A1 | 7/2005 |
| EP | 1939202 A1 | 7/2008 |
| JP | 2005089334 A | 4/2005 |
| JP | 2006-519784 A | 8/2006 |
| JP | 2007504232 A | 3/2007 |
| JP | 2009504803 A | 2/2009 |
| JP | 2009510096 A | 3/2009 |
| WO | WO-92/15581 A1 | 9/1992 |
| WO | WO-93/20847 A1 | 10/1993 |
| WO | WO-98/17279 A1 | 4/1998 |
| WO | WO-98/48805 A1 | 11/1998 |
| WO | WO-99/28321 A1 | 6/1999 |
| WO | WO-02/24225 A1 | 3/2002 |
| WO | WO-0230399 A2 | 4/2002 |
| WO | WO-03/077944 A1 | 9/2003 |
| WO | WO-2004/029054 A1 | 4/2004 |
| WO | WO-2004/066947 A2 | 8/2004 |
| WO | WO-2005/025583 A2 | 3/2005 |
| WO | WO-2005/060966 A1 | 7/2005 |
| WO | WO-2006/100226 A1 | 9/2006 |
| WO | WO-2007/024707 A2 | 3/2007 |
| WO | WO-2007034817 A1 | 3/2007 |
| WO | WO-2007034917 A1 | 3/2007 |
| WO | WO-2007038720 A2 | 4/2007 |
| WO | WO-2007/142755 A2 | 12/2007 |
| WO | WO-2008/115319 A2 | 9/2008 |
| WO | WO-2009/005687 A1 | 1/2009 |
| WO | WO-2009/099650 A2 | 8/2009 |
| WO | WO-2009/099650 A4 | 8/2009 |
| WO | WO-2010/093436 A2 | 8/2010 |
| WO | WO 2011139348 A2 * | 11/2011 |

OTHER PUBLICATIONS

"U.S. Appl. No. 12/064,529, Restriction Requirement mailed Aug. 24, 2011", 9 pgs.

"U.S. Appl. No. 12/367,172, Final Office Action mailed Jan. 18, 2012", 15 pgs.

"U.S. Appl. No. 12/367,172, Final Office Action mailed Apr. 13, 2012", 21 pgs.

"U.S. Appl. No. 12/367,172, Non Final Office Action mailed May 27, 2011", 20 pgs.

"U.S. Appl. No. 12/367,172, Response filed Mar. 8, 2011 to Restriction Requirement mailed Dec. 8, 2010", 11 pgs.

"U.S. Appl. No. 12/367,172, Response filed Nov. 16, 2011 to Non Final Office Action mailed May 27, 2011", 6 pgs.

"U.S. Appl. No. 12/367,172, Restriction Requirement mailed Dec. 8, 2010", 6 pgs.

"Australian Application Serial No. 2006283524, Office Action mailed Mar. 27, 2008", 1 pg.

"Australian Application Serial No. 2006283524, Office Action mailed Aug. 3, 2011", 4 pgs.

"Australian Application Serial No. 2006283524, Preliminary Amendment mailed Mar. 3, 2008", 18 pgs.

"Australian Application Serial No. 2006283524, Response filed May 19, 2008 to Office Action mailed Mar. 27, 2008", 10 pgs.

"Australian Application Serial No. 2007257423, Examiner Report mailed Jun. 6, 2011", 2 pgs.

"Australian Application Serial No. 2007257423, First Examiner Report mailed Sep. 22, 2010", 4 pgs.

"Australian Application Serial No. 2007257423, Office Action mailed Oct. 20, 2011", 2 pgs.

"Australian Application Serial No. 2007257423, Response flied Dec. 19, 2011 to Office Action mailed Oct. 20, 2011", 5 pgs.

"Australian Application Serial No. 2007257423, Response filed May 31, 2011 to First Examiner Report mailed Sep. 22, 2010", 16 pgs.

"Australian Application Serial No. 2007257423, Response filed Sep. 13, 2011 to Examination Report mailed Jun. 6, 2011", 12 pgs.

"Australian Application Serial No. 2008227128, Preliminary Amendment filed Sep. 7, 2009", 45 pgs.

"Brazilian Application Serial No. PI 0807196-9, Amendment filed Mar. 2, 2011", 13 pgs.

"Canadian Application Serial No. 2,653,941, Office Action mailed Aug. 23, 2010", 5 pgs.

"Canadian Application Serial No. 2,653,941, Response filed Feb. 23, 2011 to Office Action Received mailed Aug. 23, 2010", 20 pgs.

(56) References Cited

OTHER PUBLICATIONS

"Canadian Application Serial No. 2,677,733, Voluntary Amendment filed Aug. 7, 2009", 45 pgs.
"Chinese Application Serial No. 200680038761.X, Office Action mailed Mar. 22, 2012", 4 pgs.
"Chinese Application Serial No. 200680038761.X, Office Action mailed Apr. 14, 2010", (w/ English Translation), 9 pgs.
"Chinese Application Serial No. 200680038761.X, Office Action mailed Jun. 23, 2011", (w/ English Translation), 9 pgs.
"Chinese Application Serial No. 200680038761.X, Office Action Response Filed Oct. 29, 2010", (w/ English Translation of Amended Claims), 22 pgs.
"Chinese Application Seriai No. 200680038761.X, Response filed Sep. 7, 2011 to Office Action mailed Jun. 23, 2011", (w/ English Translation of Amended Claims), 19 pgs.
"Chinese Application Serial No. 200880011525.8, Office Action mailed Jan. 30, 2012", (English Translation), 6 pgs.
"Chinese Application Serial No. 200880011525.8, Voluntary Amendment filed Dec. 2, 2010", (w/ English Translation of Claims), 12 pgs.
"Chinese Application Serial No. 200980112411.7, Voluntary Amendment filed Jan. 31, 2011", (w/ English Translation of Claims), 74 pgs.
"Chinese Application Serial No. 200980112411.7, Office Action mailed Feb. 2, 2012", (w/ English Translation, 9 pgs.
"Eurasian Application Serial No. 200901078, Office Action mailed May 26, 2011", 5 pgs.
"Eurasian Application Serial No. 200901078, Office Action mailed Sep. 21, 2011", w/ English Translation), 4 pgs.
"Eurasian Application Serial No. 200901078, Office Action mailed Apr. 2, 2012", (w/ English Translation), 3 pgs.
"Eurasian Application Serial No. 200901078, Response filed Sep. 13, 2011", 13 pgs.
"Eurasian Application Serial No. 200901078, Response filed Mar. 21, 2012 to Office Action mailed Sep. 21, 2011", 8 pgs.
"European Application Serial No. 06813535.9, Extended Search Report mailed Oct. 24, 2011", 6 pgs.
"European Application Serial No. 06813535.9, Voluntary Amendment filed Apr. 22, 2008", 9 pgs.
"European Application Serial No. 08799591.6, Office Action mailed May 21, 2012", 4 pgs.
"European Application Serial No. 08799591.6, Office Action mailed Jun. 4, 2010", 4 pgs.
"European Application Serial No. 08799591.6, Response Filed Dec. 2, 2010 mailed Jun. 4, 2010" 20 pgs.
"European Application Serial No. 08799591,6, Response filed Nov. 22, 2011 to Office Action mailed May 17, 2011", 26 pgs.
"European Application Serial No. 08799591.6, Office Action mailed May 17, 2011", 5 pgs
"European Application Serial No. 09709019,5, Extended European Search Report mailed Feb. 15, 2011", 8 pgs.
"I. Pharmaceutical Importance of Crystallin Hydrates", [online]. [retrieved on May 30, 2008]. Retrieved from the Internet: <URL: http://www.netlibrary.com/nlreader.dll?bookid=12783 &filename=Page_126.html>, (2008), 126-127.
"International Application Serial No. PCT/US06/32371 , International Search Report mailed Jul. 23, 2007", 3 pgs.
"International Application Serial No. PCT/US06/32371, Written Opinion mailed Jul. 23, 2007", 6 pgs.
"International Application Serial No. PCT/U52007/009840, International Preliminary Report on Patentability mailed Dec. 18, 2008", 9 pgs.
"International Application Serial No. PCT/US2008/001631, International Preliminary Examination Report mailed Aug. 20, 2008", 12 pgs.
"International Application Serial No. PCT/US2008/001631, International Search Report mailed Jan. 21, 2009", 6 pgs.
"International Application Serial No. PCT/U52008/001631, Written Opinion mailed Jan. 2109", 9 pgs.

"International Application Serial No. PCT/US2009/000771, International Search Report mailed Aug. 28, 2009", 4 pgs.
"International Application Serial No. PCT/US2009/000771, Written Opinion mailed Aug. 28, 2009", 5 pgs.
"International Application Serial No. PCT/US2010/000369, International Preliminary Report on Patentability dated Jun. 28, 2011", 13 pgs.
"International Application Serial No. PCT/US2010/000369, International Search Report mailed Sep. 21, 2010", 6 pgs.
"International Application Serial No. PCT/U52010/000369, Partial International Search Report mailed Jul. 5, 2010", 6 pgs.
"International Application Serial No. PCT/US2010/000369, Written Opinion mailed Sep. 21, 2010", 9 pgs.
"Japanese Application Serial No. 2008-528017, Office Action mailed May 22, 2012", 3 pgs.
"Japanese Application Serial No. 2008-528017, Preliminary Amendment filed Aug. 12, 2009", 26 pgs.
"Japanese Application Serial No. 2009-549102, Voluntary Amendment filed Feb. 7, 2011", (w/ English Translation of Amended Claims), 24 pgs.
"Japanese Application Serial No. 2010-545884, Voluntary Amendment filed Oct. 7, 2010", 65 pgs.
"Mexican Application Serial No. MX/a/2010/008697, Office Action mailed Nov. 28, 2011", 4 pgs.
"Mexican Application Serial No. MX/a/2010/008697, Office Action mailed May 10, 2012", (English Translation), 3 pgs.
"Mexican Application Serial No. MX/a/2010/008697, Response filed Mar. 28, 2012", 22 pgs.
"Singapore Application Serial No. 201005638-0, Office Action mailed Nov. 9, 2011", 16 pgs.
"Singapore Application Serial No. 201005638-0, Search Report mailed Oct. 27, 2011", 7 pgs.
"Singapore Application Serial No. 201005638-0, Written Opinion mailed Oct. 27, 2011", 8 pgs.
"Singapore Application Serial No. 201005638-0, Office Action Response filed Mar. 29, 2012 to Office Action mailed Nov. 9, 2011", (English Translation), 91 pgs.
Baenziger, S., et al., "Triggering TLR7 in mice induces immune activation and lymphoid system disruption, resembling HIV-mediated pathology", *Blood*, 113(2), (Jan. 8, 2009), 377-388.
Bryan, G. T., et al., "Interferon (IFN) and IFN Inducers Protect Mouse Bladder Urothelium Against Carcinogenicity by FANFT", *Journal of Cancer Research and Clinical Oncology*, 116(Suppl. Part 1), (Abstract A3.106.36), (15th International Cancer Congress, Hamburg, Aug. 16-22, 1990), (1990), p. 308.
Carson, D. A., et al., "TLR Agonists", U.S. Appl. No. 60/710,337, filed Aug. 22, 2005, 52 pgs.
Chan, M., et al., "Synthesis and immunological characterization of toll-like receptor 7 agonistic conjugates", *Bioconjug Chem.*, 20(6), (Jun. 2009), 1194-200.
Colombo, R., et al., "Combination of intravesical chemotherapy and hyperthermia for the treatment of superficial bladder cancer: preliminary clinical experience", *Crit Rev Oncol Hematol.*, 47(2), (Aug. 2003), 127-139.
Dolan, M. E, et al., "Metabolism of $O^6$-benzylguanine, an inactivator of $O^6$-alkylguanine-DNA alkyltransferase.", *Cancer Res.*, 54(19), (Oct. 1, 1994), 5123-5130.
Hayashi, T., et al., "Mast cell-dependent anorexia and hypothermia induced by mucosal activation of Toll-like receptor 7", *Am J Physiol Regul Integr Comp Physiol.*, 295(1), (2008), R123-R132.
Jin, G., et al., "Synthesis and immunostimulatory activity of 8-substituted amino 9-benzyladenines as potent Toll-like receptor 7 agonists.", *Bioorg Med Chem Lett.*, 16(17), (Sep. 1, 2006), 4559-4563.
Kobayashi, H., et al., "Prepriming: a novel approach to DNA-based vaccination and immunomoduiation", *Springer Seminars in Immunopathology*, 22(Nos. 1-21, (2000), 85-96.
Kulikov, V. I, et al., "Lipid derivatives of prostaglandins and nonsteroidal antiinflammatory drugs (a review)", *Pharmaceutical Chemistry Journal*, 31(4), (1997), 173-177.
Kurimoto, A., et al., "Synthesis and structure-activity relationships of 2-amino-8-hydroxyadenines as orally active interferon inducing agents", *Bioorg. Med Chem.*, 11(24), (Dec. 1, 2003), 5501-8.

(56) References Cited

OTHER PUBLICATIONS

Lee, J., et al., "Molecular basis for the inimunostimulatory activity of guanine nucleoside analogs: Activation of Toll-like receptor 7", *Proc. Natl. Acad. Sci.*, 100(111, (2003), 6646-6651.

Liu, H., et al., "Tumour growth inhibition by an imidazoguinoline is associated with c-Myc down-regulation in urothelial cell carcinoma", *BJU International*, 101(7), (Apr. 2008), 894-901.

Mayer, R., et al., "A randomized controlled trial of intravesical bacillus cairnette-guerin for treatment refractory interstitial cystitis", *Journal of Urology*, 173(4), (Apr. 2005), 1186-1191.

Miller, R L, et al., "Imiquimod applied topically: a novel immune response modifier and new class of drug", *Int J Immunopharmacol.*, 21(1). (Jan. 1999), 1-14.

Mosmann, T. R., et al., "TH1 and TH2 cells: different patterns of lymphokine secretion lead to different functional properties", *Annual Review Immunology*, 7, (1989), 145-173.

Rohn, S., et al., "Antioxidant activity of protein-bound quercetin", *J Agric Food Chem.*, 52(15), (Jul. 28, 2004), 4725-4729.

Schon, M., et al,, "Tumor-Selective induction of Apoptosis and the Small-Molecule Immune Response Modifier Imiquimod", *J Natl Cancer Inst*, 95(15), (2003), 1138-1149.

Sidky, Y. A., et al., "Curative effectiveness of the interferon inducing imiquimod as a signal agent in mouse bladder tumors", *Proceedings, Eighty-Fourth Meeting of the American Association for Cancer Research*, vol. 34, (Abstract 2789) (May 19-22, 1993, Orlando, FL), (Mar. 1993), p. 467.

Sidky, Y. A, et al., "Effects of Treatment with an Oral Interferon Inducer, Imidazoquinolinamine (R-837), on the Growth of Mouse Bladder Carcinoma FCB", *Journal of Interferon Research*, 10(Supp 1), (Abstract II6-12) (Annual Meeting of the ISIR, San Francisco, CA, Nov. 14-18, 1990), (Nov. 1990), S123.

Sidky, Y. A., et al., "Effects of treatment with the oral interferon inducer, R-837, on the growth of mouse colon carcinoma, MC-26", Proceedings, 81st Annual Meeting of the *American Association for Cancer Research*, vol. 31, (Abstract 2574), (Mar. 1990), p. 433.

Sidky, Y. A, et al., "Inhibition of murine tumor growth by an interferon-inducing imidazoquinolinamine", *Cancer Research*, 52(13), (Jul. 1, 1992), 3528-33.

Sidky, Y. A., et al., "Inhibition of tumor-induced angiogenesis by the interferon inducer Imiquimod", Proceedings, Eighty-Third Annual Meeting of the American Association of *Cancer Research*, vol. 33, (Abstract 458) (May 20-23, 1992, San Diego, CA), (Mar. 1992).

Simons, M. P., et al., "Identification of the Mycobacterial Subcomponents Involved in the Release of Tumor Necrosis Factor-Related Apoptosis-Inducing Ligand from Human Neutrophils", *Infection and Immunity*, 75(3), (2007), 1265-1271.

Smith, E. B., et al., "Antitumor Effects of Imidazoquinolines in Urothelial Cell Carcinoma of the Bladder", *The Journal of Urology*, 177(6), (Abstract Only), (2007), 3 pgs.

Smith, E. B, et al., "Antitumor effects of imidazoquinolines in urothelial cell carcinoma of the bladder", *J Urol.*, 177(6), (May 2007), 2347-2351.

Smith, E. B., et al., "Effects of Imiquimod, a toll-like receptor-7 agonist, on cell proliferation and cytokine production in bladder cancer in vitro and in vivo", *Journal of Urology*, 173(4), (Suppl. 5), (Apr. 2005), p. 158.

Spohn, R., et al., "Synthetic lipopeptide adjuvants and Toll-like receptor 2-structure-activity relationships", *Vaccine*, 22(19), (Jun. 23, 2004), 2494-2499.

Veronese, F. M., et al., "The impact of PEFylation on biological therapies", *BioDrugs*, 22(5), (2008), 315-329.

Wille-Reece, U., et al., "HIV Gag protein conjugated to a Toll-like receptor 7/8 agonist improves the magnitude and quality of Th1 and CD8+ T cell responses in nonhuman primates", *Proc. Natl. Acad. Sci. USA*, 102(42), (Oct. 18, 2005), 15190-15194.

Wu, C., et al., "Immunotherapeutic activity of a conjugate of a Toll-like receptor 7 ligand", *Proc. Natl. Acad. Sci. USA*, 104(10), (2007), 3990-3995.

Yang, V. C., et al., "Bioconjugates for Effective Drug Targeting", *Advanced Drug Delivery Reviews* 55 (203), 169-170.

Zaks, K, et al., "Efficient immunization and cross-priming by vaccine adjuvants containing TLR3 or TLR9 agoinst complexed to cationic Liposomes", *Journal of Immunology*, 176(12), (Jun. 15, 2006), 7335-7345.

"U.S. Appl. No. 12/027,960, Response to Rule 312 Communication mailed Nov. 14, 2012", 2 pgs.

"U.S. Appl. No. 12/064,529, Preliminary Amendment filed Feb. 22, 2008", 11 pgs.

"U.S. Appl. No. 12/302,738, Non Final Office Action mailed Jan. 2, 2013", 11 pgs.

"U.S. Appl. No. 12/302,738, Response filed Nov. 19, 2012 to Restriction Requirement mailed Oct. 19, 2012", 7 pgs.

"U.S. Appl. No. 12/302,738, Restriction Requirement mailed Oct. 19, 2012", 7 pgs.

"Chinese Application Serial No. 200880011525.8, Office Action mailed Oct. 16, 2012", 13 pgs.

"Chinese Application Serial No. 200880011525.8, Response filed Feb. 27, 2013 to Office Action mailed Oct. 16, 2012", 10 pgs.

"Chinese Application Serial No. 200980112411.7, Office Action mailed Nov. 5, 2012", 15 pgs.

"Eurasian Application Serial No. 201101165, Office Action mailed Dec. 12, 2012", 7 pgs.

"Eurasian Application Serial No. 200901078, Office Action mailed Sep. 18, 2012", 4 pgs.

"Eurasian Application Serial No. 201001264, Response filed Dec. 19, 2012 to Office Action mailed Sep. 12, 2012", 10 pgs.

"European Application Serial No. 2004181.9, Extended EP Search Report mailed Sep. 13, 2012", 8 pgs.

"European Application Serial No. 10706399.2,Examination Notification mailed Oct. 2, 2012", 6 pgs.

"Israel Application Serial No. 207246, Office Action mailed Feb. 10, 2013", 2 pgs.

"Israeli Application Serial No. 200240, Examiner Report mailed Aug. 28, 2012", 4 pgs.

"Israeli Application Serial No. 200240, Response filed Dec. 17, 2012 to Examiner Report mailed Aug. 28, 2012", 9 pgs.

"Israeli Application Serial No. 214572, Office Action mailed Nov. 13, 2012", EN Office Action only, 2 pgs.

"Japanese Application Serial No. 2009-549102, Office Action mailed Oct. 16, 2012", 10 pgs.

"Japanese Application Serial No. 2009-549102, Response filed Mar. 22, 2013 to Office Action mailed Oct. 16, 2012", 7 pgs.

"Japanese Application Serial No. 2011-549168, Amendment Filed Dec. 27, 2012", 6 pgs.

"Singapore Application Serial No. 201005638-0, Office Action mailed Dec. 6, 2012", 6 pgs.

Jin, G., "Synthesis and immunostimulatory activity of 8-substituted amino 9-benzyladenines as potent Toll-like receptor 7 agonists", Bioorg Med Chem Lett., 16(17), (Sep. 1, 2006), 4559-63.

Smith, Eric B., et al., "Antitumor Effects of Imidazoquinolines in Urothelial Cell Carcinoma of the Bladder", The Journal of Urology, 177(6), (Jun. 2007), 2347-2351.

Wille-Reece, Ulrike, et al., "HIV Gag protein conjugated to a Toll-like receptor 7/8 agonist improves the magnitude and quality of Th1 and CD8+ T cell responses in nonhuman primates", Proc Natl Acad Sci U S A., 102(42), (Oct. 18, 2005), 15190-4.

Wu, Christina C, et al., "Immunotherapeutic activity of a conjugate of a Toll-like receptor 7 ligand", Proc Natl Acad Sci U S A., 104(10), (Mar. 6, 2007), 3990-5.

Zaks, Karen, et al., "Efficient immunization and cross-priming by vaccine adjuvants containing TLR3 or TLR9 agonists complexed to cationic liposomes", J Immunol., 176(12), (Jun. 15, 2006), 7335-45.

"U.S. Appl. No. 12/027,960, 312 Amendment filed Nov. 1, 2012", 7 pgs.

"U.S. Appl. No. 12/302,738, Preliminary Amendment filed Nov. 26, 2008", 8 pgs.

"U.S. Appl. No. 12/302,738, Response filed Jun. 26, 2013 to Non Final Office Action mailed Jan. 2, 2013", 10 pgs.

"U.S. Appl. No. 13/682,208, Preliminary Amendment filed Nov. 20, 2012", 7 pgs.

"U.S. Appl. No. 13/682,208, Restriction Requirement mailed Jun. 6, 2013", 9 pgs.

(56) References Cited

OTHER PUBLICATIONS

"U.S. Appl. No. 13/736,545, Preliminary Amendment filed Mar. 6, 2013", 3 pgs.
"U.S. Appl. No. 13/791,175, Non Final Office Action mailed Jun. 7, 2013", 11 pgs.
"U.S. Appl. No. 13/791,175, Preliminary Amendment filed Mar. 8, 2013", 4 pgs.
"Australian Application Serial No. 2009210655, Office Action mailed Apr. 19, 13", 3 pgs.
"Chinese Application Serial No. 200980112411.7—Translation of the cited CN OA—1133.050CN1", 8 pgs.
"Eurasian Application Serial No. 200901078—Pending Claims", 2 pgs.
"Eurasian Application Serial No. 201001264, Office Action mailed Mar. 21, 2013", 3 pgs.
"European Application Serial No. 09709019.5, Office Action mailed Mar. 19, 2013", 5 pgs.
"European Application Serial No. 10706399.2, Examination Notification mailed Apr. 17, 2013", 4 pgs.
"European Application Serial No. 13001458.2, Extended European Search Report mailed Apr. 22, 2013", 5 pgs.
"Israel Application Serial No. 207246, Response filed Jun. 10, 2013 to Office Action mailed Feb. 10, 2013", 7 pgs.
"Japanese Patent Application Serial No. 2008-528017—Translation of Office Action—103.044JP1", 4 pgs.
"Mexican Application Serial No. MX/a/2011/008500, Office Action mailed Jul. 4, 2013".
Butler, Roslyn S, et al., "Highly fluorescent donor—acceptor purines", J. Mater. Chem., 17, (2007), 1863-1865.
Tyagi, P., et al., "Local drug delivery to bladder using technology innovations", Urol Clin North Am., 33(4), (Nov. 2006), 519-30.
"U.S. Appl. No. 12/027,960, Notice of Allowance mailed Aug. 1, 2012", 11 pgs.
"U.S. Appl. No. 12/064,529, Final Office Action mailed Sep. 20, 2012", 14 pgs.
"U.S. Appl. No. 12/367,172 , Response filed Aug. 13, 2012 to Final Office Action mailed Apr. 13, 2012", 9 pgs.
"Australian Application Serial No. 2006283524, Response filed Aug. 2, 2012 to Examiner Report mailed Aug. 3, 2011", 34 pgs.
"Canadian Application Serial No. 2,620,182, Office Action mailed Aug. 24, 2012", 5 pgs.
"Chinese Application Serial No. 200880011525.8, Office Action mailed Jul. 5, 2012", 14 pgs.
"Chinese Application Serial No. 200880011525.8, Response filed Sep. 20, 2012 to Office action Mailed Jul. 5, 2012", 12 pgs.
"Chinese Application Serial No. 200980112411.7, Response filed Aug. 15, 2012 to Office Action mailed Feb. 2, 2012", (w/ English Translation of Amended Claims), 70 pgs.
"European Application Serial No. 08799591.6, Office Action Response Dated Sep. 20, 2012", 31 Pgs.
"Singapore Application Serial No. 201005638-0, Response filed Aug. 22, 2012 to Office Action mailed Jun. 27, 2012", 2 pgs.
U.S. Appl. No. 12/302,738, Response filed Dec. 3, 2013 to Final Office Action mailed Oct. 3, 2013, 8 pgs.
U.S. Appl. No. 13/682,208, Non Final Office Action mailed Nov. 7, 2013, 13 pgs.
U.S. Appl. No. 13/791,175, Response filed Nov. 1, 2013 to Non Final Office Action mailed Jun. 7, 2013, 8 pg.
Eurasian U.S. Appl. No. 201101165, Response filed Oct. 28, 2013 to Office Action mailed Jun. 28, 2013, (w/ English Translation of Amended Claims), 10 pgs.
Israeli Application Serial No. 214572, Response filed Nov. 3, 2013 to Office Action mailed Jul. 9, 2013, (English Translation of Claims), 5 pgs.
Mexican Application Serial No. MX/a/2011/008500, Response Action mailed Jun. 24, 2013, (w/ English Translation of Claims), 17 pgs.
Julien, R. M., "Chapter 2: Pharmacodynamics: How Drugs Act", *A Primer of Drug Action* (Ninth Edition); Worth Publishers, (2001), 37-57.
Lippard, Stephen J. et al., "Chemical synthesis: The art of chemistry", *Nature. 416.* (2002), pg. 587.
U.S. Appl. No. 12/302,738, Final Office Action mailed Oct. 3, 2013, 11 pgs.
U.S. Appl. No. 13/682,208, Response filed Aug. 7, 2013 to Restriction Requirement mailed Jun. 6, 2013, 8 pgs.
U.S. Appl. No. 13/736,545, Notice of Allowance mailed Aug. 2, 2013, 9 pgs.
Australian Application Serial No. 2009210655, Response filed Jul. 18, 2013 to First Examiner Report mailed Apr. 19, 2013, 19 pgs.
Brazilian Patent Application Serial No. PI0907907, Amendment filed Dec. 27, 2011, 11 pgs.
Chinese Application Serial No. 200980112411.7, Rejection Decision mailed Jul. 23, 2013, (w/ English Translation), 14 pgs.
Chinese Application Serial No. 201080016320.6, Office Action mailed Jul. 8, 2013, (w/ English Translation), 16 pgs.
Eurasian Application Serial No. 200901078, Response filed Jul. 29, 2013 to Office Action mailed Jan. 29, 2013, (w/ English Translation of Claims), 138 pgs.
Eurasian Application Serial No. 201001264, Office Action mailed Sep. 26, 2013, (w/ English Translation), 3 pgs.
Eurasian Application Serial No. 201001264, Response filed Jun. 5, 2013 to Office Action mailed Mar. 20, 2013, (w/ English Translation of Amended Claims), 11 pgs.
Eurasian Application Serial No. 201101165, Office Action mailed Jun. 28, 2013, (w/ English Translation), 3 pgs.
European Application Serial No. 06813535.9, Examination Notification Art. 94(3) mailed Sep. 24, 2013, 4 pgs.
European Application Serial No. 09709019.5, Examination Notification Art. 94(3) mailed Oct. 9, 2013, 6 pgs.
European Application Serial No. 09709019.5, Notification of Loss of Rights mailed Oct. 21, 2011, 2 pgs.
European Application Serial No. 09709019.5, Response filed Sep. 25, 2013 to Examination Notification Art. 94(3) mailed Mar. 19, 2013, 25 pgs.
European Application Serial No. 09709019.5, Response filed Dec. 7, 2011 to Communication pursuant to 70(2) and 70a(2) EPC and the Notification of Loss of Rights mailed Oct. 21, 2011, 41 pgs.
European Application Serial No. 10706399.2, Communication pursuant to Rules 16(1) and 162 EPC mailed Sep. 27, 2011, 2 pgs.
European Application Serial No. 10706399.2, Response filed Mar. 21, 2013 to Examination Notification mailed Oct. 2, 2012, 11 pgs.
European Application Serial No. 10706399.2, Response filed Aug. 13, 2013 to Examination Notification Art. 94(3) mailed Apr. 17, 2013, 12 pgs.
European Application Serial No. 12004181.9, Communication mailed Oct. 22, 2012, 2 pgs.
European Application Serial No. 12004181.9, Communication pursuant to Rule 112(1) EPC mailed May 31, 2013, 1 pg.
European Application Serial No. 12004181.9, Examination Notification Art. 94(3) mailed Sep. 2, 2013, 5 pgs.
European Application Serial No. 12004181.9, Response filed Jul. 31, 2013 to Communication pursuant to Rule 112(1) EPC mailed May 31, 2013 and Communication mailed Oct. 22, 2012, 9 pgs.
European Application Serial No. 13001458.2, Communication pursuant to Rules 70(2) and 70a(2) EPC mailed Jul. 1, 2013, 1 pg.
Indian Application Serial No. 2064/delnp/2008, Examination Report mailed Aug. 21, 2012, 5 pgs.
Indian Application Serial No. 5675/DELNP/2009, Voluntary Amendment filed Feb. 18, 2011, 7 pgs.
International Application Serial No. PCT/US06/32371, International Preliminary Report on Patentability mailed Mar. 5, 2008, 6 pgs.
International Application Serial No. PCT/US2009/000771, International Preliminary Report on Patentability mailed Aug. 19, 2010, 8 pgs.
Israel Application Serial No. 214572, Office Action mailed Jul. 19, 2013, (English Translation), 3 pgs.
Israeli Application Serial No. 200240, Examiner Report mailed Aug. 5, 2013, (English Translation), 3 pgs.
Japanese Application Serial No. 2009-549102, Response filed Aug. 20, 2013 to Office Action mailed May 29, 2013, (w/ English Translation of Amended Claims), 5 pgs.

(56) References Cited

OTHER PUBLICATIONS

Japanese Application Serial No. 2010-545884, Amendment filed Jan. 23, 2012, (English Translation), 7 pgs.

Japanese Application Serial No. 2010-545884, Office Action mailed Oct. 9, 2013, (w/ English Translation), 5 pgs.

Israeli Application Serial No. 214572, Office Action mailed Jan. 2, 2014, (English Translation), 2 pgs.

U.S. Appl. No. 12/302,738, Notice of Allowance mailed Dec. 27, 2013, 9 pgs.

U.S. Appl. No. 13/682,208, Response filed Feb. 7, 2014 to Non Final Office Action mailed Nov. 7, 2013, 9 pgs.

U.S. Appl. No. 13/736,545, Notice of Allowance mailed Mar. 18, 2014, 6 pgs.

U.S. Appl. No. 13/791,175, Final Office Action mailed Dec. 26, 2013, 12 pgs.

European Application Serial No. 13001458.2 Response filed Dec. 16, 2013 to Communication pursuant to Rules 70(2) and 70a(2) EPC mailed Jul. 1, 2013, 8 pgs.

Israeli Application Serial No. 200240, Response filed Nov. 25, 2013 to Examiner Report mailed Aug. 5, 2013, 8 pgs.

Korean Application Serial No. 10-2010-7019944, Amendment filed Jan. 10, 2014, 31 pgs.

Anders. H.-J., et al., "Molecular mechanisms of autoimmunity triggered by microbial infection", *Arthritis Reaearch &Therapy*, 7(5), (2005), 215-224.

Staros, E. B., et al., "New Approaches to Understanding Its Clinical Significance", *Am. J. Clin. Pathol.*, 123(2), (2005), 305-312.

Takeda, K., et al., "Toll-like receptors in innate immunity", *International Imminology*, 17(1), (2005), 1-14.

\* cited by examiner

OVA + VEHICLE

OVA + 6

TOLL-LIKE RECEPTOR MODULATORS AND TREATMENT OF DISEASES

CROSS-REFERENCE TO RELATED APPLICATIONS

The application claims the benefit of the filing date of U.S. application Ser. No. 61/151,737, filed on Feb. 11, 2009, the entirety of which is incorporated by reference herein.

STATEMENT OF GOVERNMENT RIGHTS

This invention was made with government support under AI056453 and AI077989 awarded by National Institutes of Health. The government has certain rights in the invention.

FIELD

The technology in part relates to molecules that modulate the function of a Toll-like receptor and methods for treating diseases by administering such molecules to a subject in need thereof.

BACKGROUND

Toll like receptors (TLRs) are pattern recognition receptors present on diverse cell types that recognize specific molecular patterns present in microbes such as bacteria, viruses or fungi (1). TLRs recognize lipoprotein (TLR2), double-stranded RNA (TLR3), lipopolysaccharide (LPS, TLR4), flagellin (TLR5), single-stranded RNA (TLR7/8), and bacterial or viral unmethylated CpG DNA (TLR9). All TLRs, except TLR3, signal through an adapter protein referred to as MyD88, resulting in the activation of NFkappaB and related cytokine genes (2).

TLR7 and 8, located intracellularly in endosome components, recognize single-stranded RNA and a distinct synthetic guanosine analog of host cells (3, 4). Guanine and uridine-rich single-stranded RNA has been identified as a natural ligand for TLR7 (5). In addition, several low molecular weight activators of TLR7 have been identified, including imidazoquinolines, and purine-like molecules (3, 6, 7). Among the latter, 9-benzyl-8-hydroxy-2-(2-methoxyethoxy) adenine ("SM"), has been identified as a potent and specific TLR7 agonist (8). Derivatives of SM have been synthesized by incorporating an aldehyde functional group on the benzyl moiety and coupling that intermediate to different auxiliary chemical entities through a bifunctional linker molecule containing a hydrazine and N-hydroxysuccinimide (9). Conjugation to mouse serum albumin (MSA) protein increased potency by 10 to 100-fold and improved the in vivo pharmacodynamics compared with the free drug. The MSA conjugate could be delivered to the respiratory system by intranasal or intratracheal administration. Drug delivery by intranasal proved to be effective in two mouse models of infectious disease, a bacterial infection and a viral infection (9). The SM intermediate also has been conjugated to a lipid, dioleoylphosphatidyl ethanolamine (DOPE), and it was determined that the conjugate possessed enhanced TLR7 agonist activity (e.g., WO 2008/115319, published on Sep. 25, 2008, based on International patent application no. PCT/US2008/001631 filed Feb. 7, 2008).

SUMMARY

Provided herein are small molecule conjugates that can modulate an activity of one or more toll-like receptors (e.g., the conjugates are agonists, antagonists, or both). The term "toll-like receptor" (TLR) refers to a member of a family of receptors that bind to pathogen-associated molecular patterns (PAMPs) and facilitate an immune response in a mammal. Ten mammalian TLRs are known, e.g., TLR1-10. The term "toll-like receptor agonist" (TLR agonist) refers to a molecule that interacts with a TLR and stimulates the activity of the receptor. Synthetic TLR agonists are chemical compounds that are designed to interact with a TLR and stimulate the activity of the receptor. Examples of TLR agonists include a TLR-7 agonist, TLR-3 agonist or TLR-9 agonist. The term "toll-like receptor antagonist" (TLR antagonist) refers to a molecule that interacts with a TLR and inhibits or neutralizes the signaling activity of the receptor. Synthetic TLR antagonists are chemical compounds designed to interact with a TLR and interfere with the activity of the receptor. Examples of TLR antagonists include a TLR-7 antagonist, TLR-3 antagonist or TLR-9 antagonist.

Thus, in one embodiment, provided herein is a compound having a structure according to Formula I:

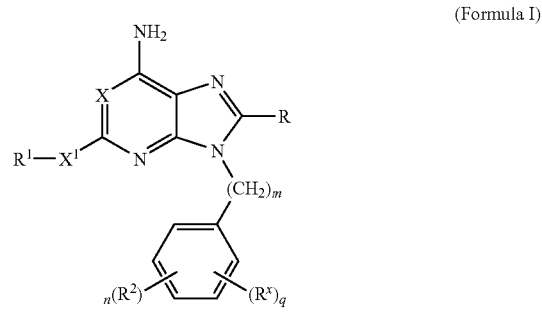

(Formula I)

or a pharmaceutically acceptable salt thereof, including a hydrate thereof, wherein:

X is N or $CR^2$;

R is $-OR^1$, $-SR^1$, or $-NR^aR^b$, $X^1$ is a bond or is $-O-$, $-S-$, or $-NR^c-$;

$R^c$ is hydrogen, C1-C10 alkyl, or substituted C1-C10 alkyl, or $R^c$ and $R^1$ taken together with the nitrogen atom can form a heterocyclic ring or a substituted heterocyclic ring;

$R^1$ is hydrogen, C1-C10 alkyl, substituted C1-C10 alkyl, C1-C10 alkoxy, substituted C1-C10 alkoxy, C1-C10 alkyl C1-C10 alkoxy, substituted C1-C10 alkyl C1-C10 alkoxy, C5-C10 aryl, substituted C5-C10 aryl, C5-C9 heterocyclic, substituted C5-C9 heterocyclic, C3-C9 carbocyclic or substituted C3-C9 carbocyclic;

each $R^2$ independently is hydrogen, $-OH$, C1-C6 alkyl, substituted C1-C6 alkyl, C1-C6 alkoxy, substituted C1-C6 alkoxy, $-C(O)-$C1-C6 alkyl (alkanoyl), substituted $-C(O)-$C1-C6 alkyl, $-C(O)-$C6-C10 aryl (aroyl), substituted $-C(O)-$C6-C10 aryl, $-C(O)OH$ (carboxyl), $-C(O)O-$C1-C6 alkyl (alkoxycarbonyl), substituted $-C(O)O-$C1-C6 alkyl, $-NR^aR^b$, $-C(O)NR^aR^b$ (carbamoyl), substituted $C(O)NR^aR^b$, halo, nitro, or cyano;

the substituents on the alkyl, aryl or heterocyclic groups are hydroxy, C1-C6 alkyl, hydroxy C1-C6 alkylene, C1-C6 alkoxy, C3-C6 cycloalkyl, C1-C6 alkoxy C1-C6 alkylene, amino, cyano, halogen, or aryl;

each $R^a$ and $R^b$ is independently hydrogen, C1-C6 alkyl, C3-C8 cycloalkyl, C1-C6 alkoxy, halo C1-C6 alkyl, C3-C8 cycloalkyl C1-C6 alkyl, C1-C6 alkanoyl, hydroxy C1-C6 alkyl, aryl, aryl C1-C6 alkyl, Het, Het C1-C6 alkyl, or C1-C6 alkoxycarbonyl;

each $R^x$ is independently —$X^2$—$((R^3)_r$—$(R^4)_s)_p$, —C(O)NR$^a$R$^b$, or —CH$_2$NH-biotin;

each $X^2$ independently is a bond or a linking group;

each $R^3$ independently is a polyethylene glycol (PEG) moiety;

each $R^4$ independently is H, —C1-C6 alkyl, —C1-C6 alkoxy, —NR$^a$R$^b$, —N$_3$, —OH, —CN, —COOH, —COOR$^1$, —C1-C6 alkyl-NR$^a$R$^b$, —C1-C6 alkyl-OH, —C1-C6 alkyl-CN, —C1-C6 alkyl-COOH, —C1-C6 alkyl-COOR$^1$, 5 to 6 membered (5-6 membered) ring, substituted 5-6 membered ring, —C1-C6 alkyl-5-6 membered ring, —C1-C6 alkyl-substituted 5-6 membered ring C2-C9 heterocyclic, or substituted C2-C9 heterocyclic;

m is 1, 2, 3, 4, 5, 6, 7, 8, 9 or 10;

n is 0, 1, 2, 3 or 4;

p is 1 to 100;

q is 1, 2, 3, 4 or 5;

r is 1 to 1,000;

s is 1 to 1,000; and the sum of n and q equals 5.

In certain embodiments, also provided is a compound having a structure according to Formula II:

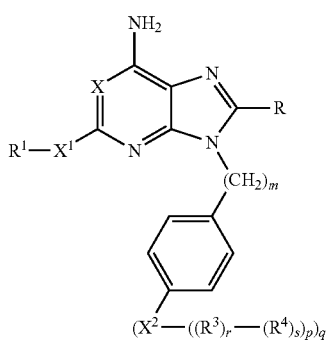

Formula II or a pharmaceutically acceptable salt thereof, or a hydrate thereof, where X, X$^1$, X$^2$, R, R$^1$, R$^2$, R$^3$, R$^4$, m, n, p, q, r and s embodiments are described above for Formula I.

In some embodiments, a compound having a structure according to Formula III is provided:

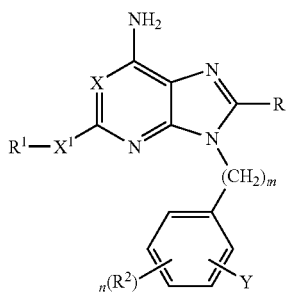

Formula III or a pharmaceutically acceptable salt thereof, or a hydrate thereof, where:

X, X', R, R$^1$ and R$^2$ embodiments are described above for Formula I;

Y is —$X^2$—$((R^3)_r$—$(X^3)_t$—$(X^4)_s)_p)_q$, $X^2$—$((R^3)_r$—$(X^3)_t$—$(X^4)_s$—$(R^4)_u)_p)_q$, $X^2$—$((X^4)_s$—$(X^3)_t$—$(R^3)_r)_p)_q$, or $X^2$—$((X^4)_s$—$(X^3)_t$—$(R^3)_r$—$(R^4)_u)_p)_q$;

$R^3$, $R^4$, m, n, p, q, r and s embodiments are described above for Formula I;

each $X^3$ independently is a bond or linking group;

each $X^4$ independently is a macromolecule;

t is 1 to 1,000; and u is 1 to 1,000.

In some embodiments, X is N. In certain embodiments, $X^1$ is oxygen, and in some embodiments, $R^1$ is a substituted C1-C10 alkyl, such as a C1-C10 alkyl C1-C10 alkoxy moiety (e.g., —CH$_2$CH$_2$OCH$_3$). $R^1$ in some embodiments consists of six or fewer non-hydrogen atoms. In some embodiments, n is 4 and $R^2$ is hydrogen in each instance.

In certain embodiments, $X^2$ and/or $X^3$ independently is an amido linking group (e.g., —C(O)NH— or —NH(O)C—); alkyl amido linking group (e.g., —C1-C6 alkyl-C(O)NH—, —C1-C6 alkyl-NH(O)C—, —C(O)NH—C1-C6 alkyl-, —NH(O)C—C1-C6 alkyl-, —C1-C6 alkyl—NH(O)C—C1-C6 alkyl-, —C1-C6 alkyl-C(O)NH—C1-C6 alkyl-, or —C(O)NH—(CH$_2$)$_t$—, where t is 1, 2, 3, or 4); substituted 5-6 membered ring (e.g., aryl ring, heteroaryl ring (e.g., tetrazole, pyridyl, 2,5-pyrrolidinedione (e.g., 2,5-pyrrolidinedione substituted with a substituted phenyl moiety)), carbocyclic ring, or heterocyclic ring) or oxygen-containing moiety (e.g., —O—, —C1-C6 alkoxy).

A PEG moiety can include one or more PEG units. A PEG moiety can include about 1 to about 1,000 PEG units, including, without limitation, about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800 or 900 units, in some embodiments. In certain embodiments, a PEG moiety can contain about 5 to about 25 PEG units, about 10 to about 50 PEG units, about 50 to about 150 PEG units, about 120 to about 350 PEG units, about 250 to about 550 PEG units or about 650 to about 950 PEG units. A PEG unit is —O—CH$_2$—CH$_2$— or —CH$_2$—CH$_2$—O— in certain embodiments.

In some embodiments, r is about 5 to about 100, and sometimes r is about 5 to about 50 or about 5 to about 25. In certain embodiments, r is about 5 to about 15 and sometimes r is about 10. In some embodiments, $R^3$ is a PEG unit and r is about 2 to about 10 (e.g., r is about 2 to about 4). In certain embodiment $R^3$ is —O—CH$_2$—CH$_2$— or —CH$_2$—CH$_2$—O—.

In some embodiments $R_3$ is —O—CH$_2$—CH$_2$— or —CH$_2$—CH$_2$—O— and r is about 1 to about 1000 (e.g., about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800, 900 or 1000). In certain related embodiments, r is about 5 to about 25, about 10 to about 50, about 50 to about 150, about 120 to about 350, about 250 to about 550 or about 650 to about 950.

In some embodiments, s is about 5 to about 100, and sometimes s is about 5 to about 50 or about 5 to about 25. In certain embodiments, s is about 5 to about 15 and sometimes s is about 10. In some embodiments, s is about 5 or less (e.g., s is 1). In some embodiments the $(R^3)_r$ substituent is linear, and in certain embodiments, the $(R^3)_r$ substituent is branched. For linear moieties, s sometimes is less than r (e.g., when $R_3$ is —O—CH$_2$—CH$_2$— or —CH$_2$—CH$_2$—O—) and at times s is 1. In some embodiments $R_3$ is a linear PEG moiety (e.g., having about 1 to about 1000 PEG units), s is 1 and r is 1. For branched moieties, s sometimes is less than, greater than or equal to r (e.g., when $R_3$ is —O—CH$_2$—CH$_2$— or —CH$_2$—CH$_2$—O—), and at times r is 1, s is 1 and p is about 1 to about 1000 (e.g., p is about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800, 900 or 1000).

In some embodiments, t is about 5 to about 100, and sometimes t is about 5 to about 50 or about 5 to about 25. In certain embodiments, t is about 5 to about 15 and sometimes t is about 10. In some embodiments, t is about 5 or less (e.g., t is 1). In certain embodiments, u is about 5 to about 100, and sometimes u is about 5 to about 50 or about 5 to about 25. In some embodiments, u is about 5 to about 15 and sometimes u is about 10. In certain embodiments, u is about 5 or less (e.g., u is 1).

In certain embodiments, a $R^4$ substituent independently is H, C1-C2 alkyl, —C1-C2 alkoxy (e.g., —OCH$_3$), —NR$^a$R$^b$, —OH, —CN, —COOH, —COOR$^1$, —C1-C2 alkyl-NR$^a$R$^b$, C1-C2 alkyl-OH, C1-C2 alkyl-CN, C1-C2 alkyl-COOH or C1-C2 alkyl-COOR$^1$. In some embodiments, $R^4$ is an optionally substituted 5-6 membered ring (e.g., aryl ring, heteroaryl ring, carbocyclic ring, heterocyclic ring). In certain embodiments, $R^4$ is not hydrogen, and sometimes $R^4$ is not hydroxyl.

In some embodiments pertaining to a compound having a structure according to Formula I, m is about 1, $R^2$ is hydrogen and n is 4, q is 1, p is 1, r is about 10 and s is 1.

Each $X^4$ can be the same macromolecule or a different macromolecule. In certain embodiments, a macromolecule is selected from the group consisting of an antibody, antibody fragment, antigen, pathogen antigen (e.g., S. aureus antigen), protein (e.g., human serum albumin protein or fragment thereof), glycerol, lipid, phospholipid (e.g., DOPE), sphingolipid and the like. In some embodiments, the macromolecule is DOPE.

In one embodiment, the invention provides a method for preventing, inhibiting or treating an inflammatory or autoimmune condition (disorder or disease) (e.g., rheumatoid arthritis) in a subject, which comprises administering a compound having the following structure:

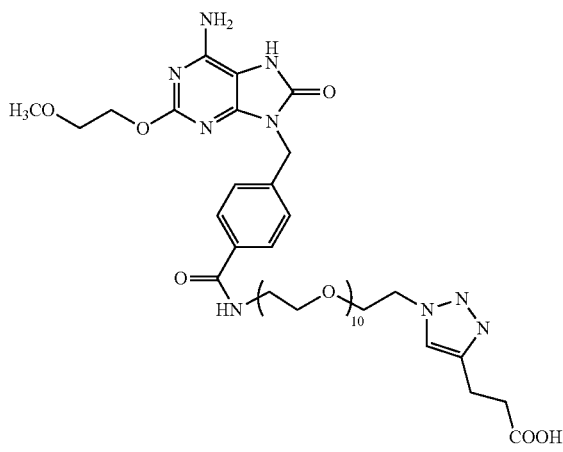

or a pharmaceutically acceptable salt thereof or hydrate thereof, to a human subject in need thereof in an amount effective to prevent, inhibit or treat the rheumatoid arthritis.

Also provided herein is a pharmaceutical composition comprising a pharmaceutically acceptable salt of a compound having a structure according to Formula I, II or III. Provided also herein is a method for preventing, inhibiting or treating an inflammation condition in a subject, which comprises administering a compound having a structure according to Formula I, II or III to a subject in need thereof in an amount effective to prevent, inhibit or treat the condition, e.g., an autoimmune disorder, or a symptom thereof. Also provided herein is a method for preventing, inhibiting treating an autoimmune condition in a subject, which comprises administering a compound having a structure according to Formula I, II or III to a subject in need thereof in an amount effective to prevent, inhibit or treat the condition or a symptom thereof, e.g., inflammation.

Thus, the invention provides compounds for use in medical therapy, such as agents that prevent, inhibit or treat inflammatory disorders or diseases, e.g., rheumatoid arthritis, or cancer, optionally in conjunction with other compounds. Accordingly, the compounds of the invention are useful to prevent, inhibit or treat an autoimmune disorder or disease, an inflammatory disorder or disease or cancer.

Also provided is the use of the compounds for the manufacture of a medicament to prevent, inhibit or treat inflammatory and/or autoimmune disorders or diseases, or cancer. In one embodiment, the invention provides methods for preventing, inhibiting or treating cancer in a subject, which comprises administering a compound having a structure according to Formula I, II or III to a subject in need thereof in an amount effective to prevent, inhibit or treat the cancer. In one embodiment, a compound of the invention is administered to a subject with cancer and in which corticosteroids, e.g., dexamethasone, prednisolone, methylprednisolone, or hydrocortisone, are indicated, cancers such as Hodgkin's lymphoma, Non-Hodgkin's lymphoma, leukemia, multiple myeloma or brain tumor. In one embodiment, a subject at risk of a cancer, the development of which is associated with inflammation, e.g., colon cancer, is administered a compound of the invention. Therefore, the invention provides compounds for use in medical therapy, such as agents that prevent, inhibit or treat cancer, optionally in conjunction with other compounds. Accordingly, the compounds of the technology are useful to prevent, inhibit or treat a variety of autoimmune disorders/diseases, inflammatory disorders/diseases and cancers.

BRIEF DESCRIPTION OF THE DRAWINGS

The drawings illustrate embodiments of the invention and are not limiting. It should be noted that for clarity and ease of illustration, these drawings are not made to scale and that in some instances various embodiments of the invention may be shown exaggerated or enlarged to facilitate an understanding of particular embodiments.

The following abbreviations are used throughout this document. Toll-like receptor (TLR), Lipopolysaccharide (LPS), Myeloid differentiation primary response gene (88) (MyD88), Bone Marrow Derived Mononuclear Cell (BMDM), Peripheral blood mononuclear cell (PBMC), Polyethylene glycol (PEG), Ethanol (EtOH), Tetrahydrofuran (THF), 1,2-Dioleoyl-sn-glycero-3-phosphoethanolamine (DOPE), N,N-Dimethylmethanamide (DMF), O-(7-Azabenzotriazol-1-yl)-N,N,N',N'-tetramethyluronium hexafluorophosphate (HATU), Dichloromethane (DCM), Triethylamine (TEA), Plasmacytoid dendritic cells (pDC), Ovalbumin (OVA), Mouse serum albumin (MSA), Human Serum albumin (HSA), and Immunoglobulin (Ig)

DETAILED DESCRIPTION

Figure 1:
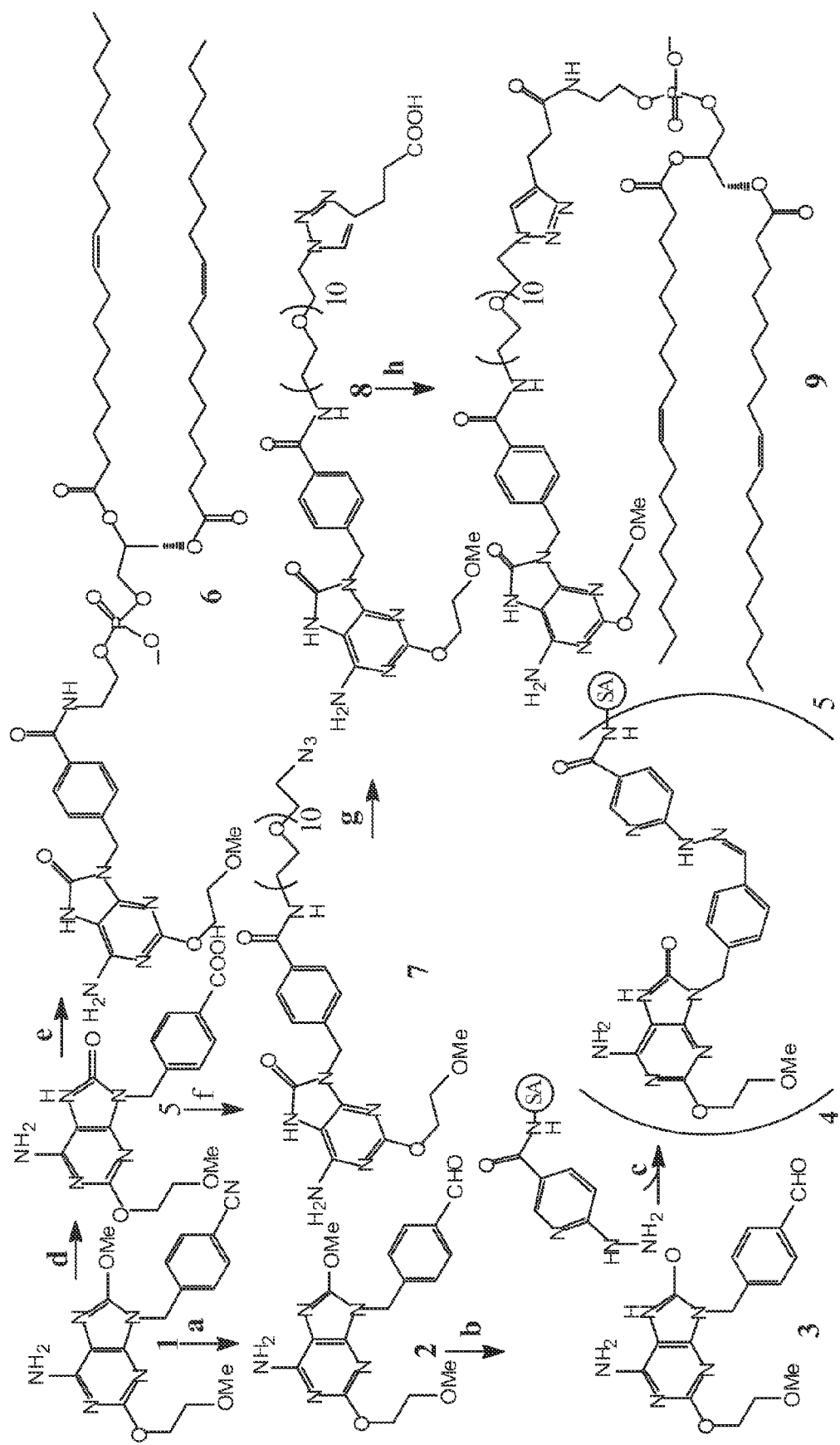
FIG. 1 illustrates the scheme used for synthesis of lipid-(6), PEG-(8), or lipid-PEG (9) TLR7 conjugates. (6), (8), and (9) refer to compound designations.

Provided herein are small molecule conjugates that are agonists or antagonists of one or more toll like receptors. Such conjugates can be utilized in a variety of ways, including, but not limited to, treatments of conditions such as autoimmune, inflammation, and cell proliferative disorders or diseases, for example.

Compounds

Small molecule TLR modulators are known. Examples of small molecules are described in U.S. Pat. No. 6,329,381, issued on Dec. 11, 2001 from patent application Ser. No. 09/555,292 filed on May 26, 2000, and in PCT/US2006/032371, filed on Aug. 21, 2006 (published as WO2007/024707 on Mar. 1, 2007); PCT/US2008/001631, filed on Feb. 7, 2008 (published as WO 2008/115319 on Sep. 25, 2008); PCT/US07/009,840, filed on Apr. 23, 2007 (published as WO/2007/142755 on Dec. 13, 2007); and U.S. provisional application No. 61/026,999, filed on Feb. 7, 2008.

It has been determined that certain small molecule TLR agonists (e.g., referred to as a "small molecule target" herein) can be conjugated to one or more PEG moieties, and the resulting conjugate can exhibit TLR antagonist activity. There are several methods known for conjugating a small molecule target with one or more PEG moieties. For example, several PEG reactants are commercially available and are suitable for conjugation to a variety of reactive groups on the small molecule (e.g., NOF Corporation, Japan (World Wide Web URL peg-drug.com/peg_product/activated_peg.html)). The term "PEG reactant" as used herein refers to a molecule that is combined with a small molecule target under conditions that generate a PEG-small molecule target conjugate product. For example, certain PEG reactants having the following structure can react with a variety of target groups on a small molecule:

$CH_3O(CH_2CH_2O)_n$—X, where X is a reactive group according to Table 1:

| Reactive Group | Reactive Group on Small Molecule Target |
|---|---|
| —CO—CH$_2$CH$_2$—COO—NHS* | —NH$_2$, —OH, —SH |
| —CO—CH$_2$CH$_2$CH$_2$—COO—NHS* | —NH$_2$, —OH, —SH |
| —CH$_2$—COO—NHS* | —NH$_2$, —OH, —SH |
| —CH$_2$CH$_2$CH$_2$CH$_2$CH$_2$—COO—NHS* | —NH$_2$, —OH, —SH |
| —CO$_2$-p-C$_6$H$_4$—NO$_2$ | —NH$_2$ |
| —CH$_2$CH$_2$—CHO | —NH$_2$ |
| —CH$_2$CH$_2$CH$_2$NH$_2$ | —COOH |
| —CH$_2$CH$_2$CH(OC$_2$H$_5$)$_2$ | —NH$_2$ |
| —CH$_2$CH$_2$SH— | SH, —N-Maleimidyl, —COOH |
| —CH$_2$CH$_2$CH$_2$NHCOCH$_2$CH$_2$—N-Maleimidyl | —SH | and where NHS* is N-Succinimidyl.

In some embodiments, a PEG reactant has a structure $CH_3O(CH_2CH_2O)_n$—X—NHS*, where X can be —COCH$_2$CH$_2$COO—, —COCH$_2$CH$_2$CH$_2$COO—, —CH$_2$COO—, and —(CH$_2$)$_5$COO—. In certain embodiments, a PEG reactant has a structure

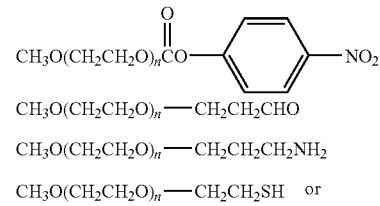

$CH_3O(CH_2CH_2O)_n$—CH$_2$CH$_2$CHO $CH_3O(CH_2CH_2O)_n$—CH$_2$CH$_2$CH$_2$NH$_2$ $CH_3O(CH_2CH_2O)_n$—CH$_2$CH$_2$SH  or

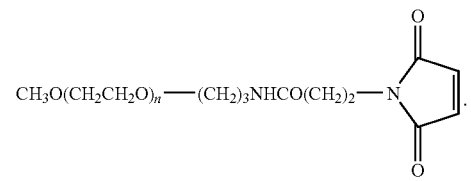

Certain PEG reactants are bifunctional in some embodiments. Examples of bifunctional PEG reactants have a structure X—(OCH$_2$CH$_2$)$_n$—X, where X is (N-Succinimidyloxycarbonyl)methyl (—CH$_2$COO—NHS), Succinimidylglutarate (—COCH$_2$CH$_2$CH$_2$COO—NHS), (N-Succinimidyloxycarbonyl)pentyl (—(CH$_2$)$_5$COO—NHS), 3-(N-Maleimidyl)propanamido, (—NHCOCH$_2$CH$_2$-MAL), Aminopropyl (—CH$_2$CH$_2$CH$_2$NH$_2$) or 2-Sulfanylethyl (—CH$_2$CH$_2$SH) in some embodiments.

In certain embodiments, some PEG reactants are heterofunctional. Examples of heterofunctional PEG reactants have the structures

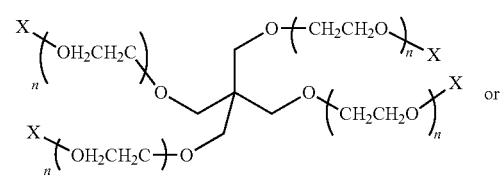

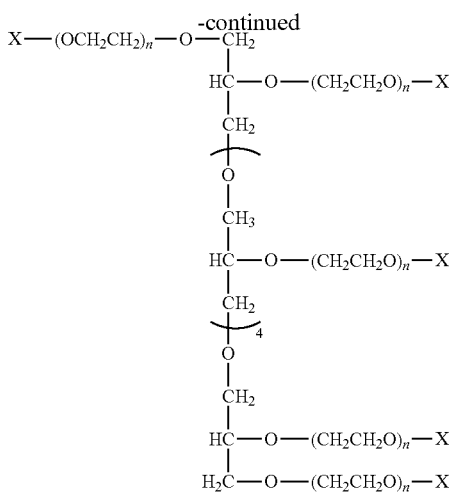

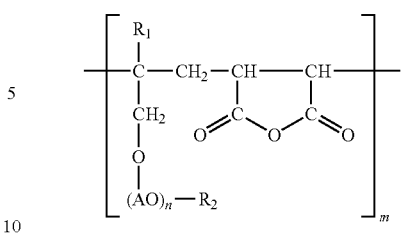

where X can be (N-Succinimidyloxycarbonyl)methyl (—CH$_2$COO—NHS), Succinimidylglutarate (—COCH$_2$CH$_2$CH$_2$COO—NHS), (N-Succinimidyloxycarbonyl)pentyl (—(CH$_2$)$_5$COO—NHS), 3-(N-Maleimidyl) propanamido, (—NHCOCH$_2$CH$_2$-MAL), 3-aminopropyl (—CH$_2$CH$_2$CH$_2$NH$_2$), 2-Sulfanylethyl (—CH$_2$CH$_2$SH), 5-(N-Succinimidyloxycarbonyl)pentyl (—(CH$_2$)$_5$COO—NHS], or p-Nitrophenyloxycarbonyl, (—CO$_2$-p-C$_6$H$_4$NO$_2$), in some embodiments.

Certain branched PEG reactants also may be utilized, such as those having a structure:

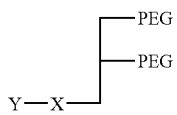

where X is a spacer and Y is a functional group, including, but not limited to, maleimide, amine, glutaryl-NHS, carbonate-NHS or carbonate-p-nitrophenol, in some embodiments. An advantage of branched chain PEG reactants is that they can yield conjugation products that have sustained release properties.

A PEG reactant also may be a heterofunctional reactant, such as

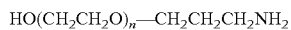

HO(CH$_2$CH$_2$O)$_n$—CH$_2$CH$_2$CH$_2$NH$_2$

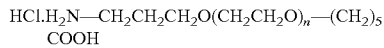

HCl.H$_2$N—CH$_2$CH$_2$CH$_2$O(CH$_2$CH$_2$O)$_n$—(CH$_2$)$_5$ COOH and

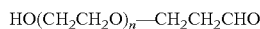

HO(CH$_2$CH$_2$O)$_n$—CH$_2$CH$_2$CHO in certain embodiments. In some embodiments, Boc*-protected-Amino-PEG-Carboxyl-NHS or Maleimide-PEG-Carboxyl-NHS reactants can be utilized.

In certain embodiments, a comb-shaped polymer may be utilized as a PEG reactant to incorporate a number of PEG units into a conjugate. An example of a comb-shaped polymer is shown hereafter.

For purposes of PEG reactants specifically shown in this section entitled "Compounds," substituent "n" or "m" shown in the PEG reactants, only, equals "r," defined above for Formula I, II or III, in some embodiments. A PEG reactant, and/or a PEG conjugate product, can have a molecular weight ranging between about 5 grams per mole to about 100,000 grams per mole. In some embodiments, a PEG reactant, and/or a PEG conjugate product, has a average, mean or nominal molecular weight of about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000 or 90000 grams per mole. In some embodiments the PEG moiety in a compound herein is homogeneous and the molecule weight of the PEG moiety is the same for each molecule of a particular batch of compound (e.g., $R^3$ is one PEG unit and r is 2 to 10).

In certain embodiments, one or more $R^4$ substituents terminate the PEG moiety (e.g., Formula I; linear or branched PEG moiety). Each $R^4$ substituent may be the same or different, and can be selected independently from the group consisting of —CH$_2$—CH$_2$—NH$_2$, —CH$_2$—CH$_2$—OH —CH$_2$—CH$_2$—COOH, —CH$_2$—CH$_2$—COOR$^1$, in some embodiments. The linker can be any suitable linker, including a linker described herein.

A suitable linker can be utilized to construct conjugates (e.g., $X^2$, $X^3$), and multiple linkers are known. Non-limiting examples of linkers that can be utilized include the following:

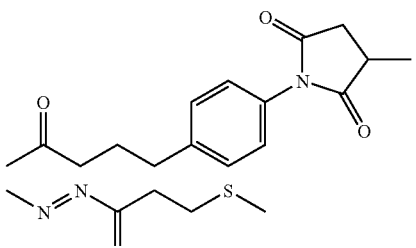

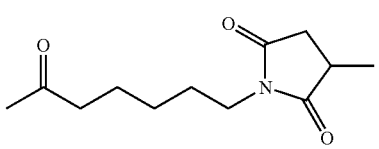

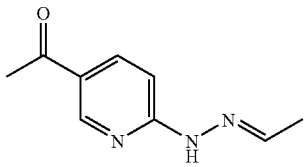

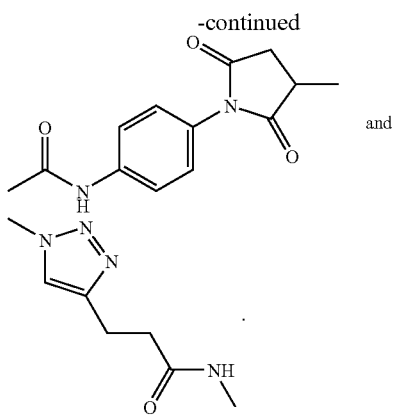
and

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2 propenyl, 3 butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described.

Typically, the alkyl, alkenyl and alkynyl substituents of the invention contain one 10C (alkyl) or two 10C (alkenyl or alkynyl). Preferably they contain one 8C (alkyl) or two 8C (alkenyl or alkynyl). Sometimes they contain one 4C (alkyl) or two 4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often optionally substituted to the extent that such substitution makes sense chemically. Typical substituents include, but are not limited to, halo, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" substituents are 2-10C alkynyl groups that are optionally substituted, and are of the formula —C≡C—Ri, wherein Ri is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each Ri group is optionally substituted with one or more substituents selected from halo, =O, =N—CN, =N—OR', =NR', OR', NR'2, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and wherein two R' can be linked to form a 3-7 membered ring optionally containing up to three heteroatoms selected from N, O and S. In some embodiments, Ri of —C≡C—Ri is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one to three O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5 membered rings as well as 6 membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)— and —$C(Me)_2$— may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R2 is alkyl, this alkyl may optionally be substituted by the remaining substituents listed as embodiments for R2 where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group. A heteroform moiety sometimes is referred to as "Het" herein.

"Halo" or "halogen," as used herein includes fluoro, chloro, bromo and iodo. Fluoro and chloro are often preferred. "Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems. As used herein, the term "heteroatom" refers to any atom that is not carbon or hydrogen, such as nitrogen, oxygen or sulfur. Illustrative examples of heterocycles include but are not limited to tetrahydrofuran, 1,3 dioxolane, 2,3 dihydrofuran, pyran, tetrahydropyran, benzofuran, isobenzofuran, 1,3 dihydro isobenzofuran, isoxazole, 4,5 dihydroisoxazole, piperidine, pyrrolidine, pyrrolidin 2 one, pyrrole, pyridine, pyrimidine, octahydro pyrrolo[3,4 b]pyridine, piperazine, pyrazine, morpholine, thiomorpholine, imidazole, imidazolidine 2,4 dione, 1,3 dihydrobenzimidazol 2 one, indole, thiazole, benzothiazole, thiadiazole, thiophene, tetrahydro thiophene 1,1 dioxide, diazepine, triazole, guanidine, diazabicyclo[2.2.1]heptane, 2,5 diazabicyclo[2.2.1]heptane, 2,3,4,4a,9,9a hexahydro 1H beta carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

In some cases, compounds described herein contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed. The compounds of the invention may also exist in one or more tautomeric forms. For example, when R is —OH, a compound described herein may exist in one or more tautomeric forms.

The term "optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

Pharmaceutical Compositions and Formulations

A compound described herein can be prepared as a pharmaceutically acceptable salt. As used herein, the term "pharmaceutically acceptable salt" refers to a derivative of the disclosed compounds where the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include conventional non-toxic salts or quaternary ammonium salts of the parent compound formed, for example, from non-toxic inorganic or organic acids. For example, conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. In other examples, conventional non-toxic salts include those derived from bases, such as potassium hydroxide, sodium hydroxide, ammonium hydroxide, caffeine, various amines, and the like. Pharmaceutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., p. 1418 (1985), the disclosure of which is hereby incorporated by reference.

The term "pharmaceutically acceptable" as used herein refers to compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The terms "stable compound" and "stable structure" are meant to indicate a compound that is sufficiently robust to survive isolation to a useful degree of purity from a reaction mixture, and formulation into an efficacious therapeutic agent. Stable compounds are contemplated herein for use in treatment methods described.

A compound described herein can be formulated in combination with one or more other agents. The one or more other agents can include, without limitation, another compound described herein, an anti-cell proliferative agent (e.g., chemotherapeutic), an anti-inflammatory agent, and an antigen.

A compound described herein can be formulated as a pharmaceutical composition and administered to a mammalian host, such as a human patient or nonhuman animal, in a variety of forms adapted to the chosen route of administration, e.g., orally or parenterally, by intravenous, intramuscular, topical or subcutaneous routes. In certain embodiments, a composition is locally administered, e.g., intravesicularly. A composition often includes a diluent as well as, in some cases, an adjuvant, buffer, preservative and the like. A compound can be administered also in a liposomal composition or as a microemulsion, in certain embodiments. Various sustained release systems for drugs have also been devised, and can be applied to a compound described herein. See, for example, U.S. Pat. No. 5,624,677, the methods of which are incorporated herein by reference.

Thus, compounds may be systemically administered, e.g., orally, in combination with a pharmaceutically acceptable vehicle such as an inert diluent or an assimilable edible carrier.

Compounds described herein may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

Tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

An active compound may be administered by infusion or injection. Solutions of an active compound or a pharmaceutically acceptable salt thereof can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

A pharmaceutical dosage form can include a sterile aqueous solution or dispersion or sterile powder comprising an active ingredient, which are adapted for the extemporaneous preparation of sterile solutions or dispersions, and optionally encapsulated in liposomes. The ultimate dosage form sometimes is a sterile fluid and stable under the conditions of manufacture and storage. A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. An isotonic agent, for example, a sugar, buffer or sodium chloride is included in some embodiments. Prolonged absorption of an injectable composition can be brought about by the use in the compositions of agents delaying absorption, for example, aluminum monostearate and gelatin. Sterile solutions often are prepared by incorporating an active compound in a required amount in an appropriate solvent, sometimes with one or more of the other ingredients enumerated above, followed by filter sterilization. In the case of sterile powders for the preparation of sterile injectable solutions, preparation methods sometimes utilized are vacuum drying and the freeze drying techniques, which yield a powder of an active ingredient in addition to any additional desired ingredient present in the previously sterile-filtered solutions.

For topical administration, a compound herein may be applied in pure form, e.g., when in liquid form. However, it is generally desirable to administer a compound as a composition or formulation, in combination with an acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949. The ability of a compound herein to act as a TLR agonist or TLR antagonist may be determined using pharmacological models which are known, including the procedures disclosed by Lee et al., PNAS, 100:6646 (2003). Generally, the concentration of the compound(s) in a liquid composition will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general a suitable dose sometimes is in the range of from about 0.5 to about 100 mg/kg, e.g., from about 10 to about 75 mg/kg of body weight per day, such as 3 to about 50 mg per kilogram body weight of the recipient per day, and often is in the range of 6 to 90 mg/kg/day, or about 15 to 60 mg/kg/day. A compound may be conveniently administered in unit dosage form, and for example, contain 5 to 1000 mg, or 10 to 750 mg, or 50 to 500 mg of active ingredient per unit dosage form. An active ingredient can be administered to achieve peak plasma concentrations of an active compound of from about 0.01 to about 100 pM, about 0.5 to about 75 pM, about 1 to 50 pM, or about 2 to about 30 pM. Such concentrations may be achieved, for example, by the intravenous injection of a 0.05 to 5% solution of an active ingredient, optionally in saline, or orally administered as a bolus containing about 1-100 mg of an active ingredient. Desirable blood levels may be maintained by continuous infusion to provide about 0.01-5.0 mg/kg/hr or by intermittent infusions containing about 0.4-15 mg/kg of the active ingredient(s). A desired dose may conveniently be presented in a single dose or as divided doses administered at appropriate intervals, for example, as two, three, four or more sub-doses per day. A sub-dose itself may be further divided, e.g., into a number of discrete loosely spaced administrations; such as multiple inhalations from an insufflator or by application of a plurality of drops into the eye.

Treatments

The terms "treat" and "treating" as used herein refer to (i) preventing a pathologic condition from occurring (e.g. prophylaxis); (ii) inhibiting the pathologic condition or arresting its development; (iii) relieving the pathologic condition; and/or (iv) ameliorating, alleviating, lessening, and removing symptoms of a condition. A candidate molecule or compound described herein may be in a therapeutically effective amount in a formulation or medicament, which is an amount that can lead to a biological effect (e.g., inhibiting inflammation), or lead to ameliorating, alleviating, lessening, relieving, diminishing or removing symptoms of a condition, e.g., disease, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (e.g., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

The term "therapeutically effective amount" as used herein refers to an amount of a compound provided herein, or an amount of a combination of compounds provided herein, to treat or prevent a disease or disorder, or to treat a symptom of the disease or disorder, in a subject. As used herein, the terms "subject" and "patient" generally refers to an individual who will receive or who has received treatment (e.g., administration of a compound described herein) according to a method described herein.

A compound described herein can be administered to a subject in need thereof to potentially prevent, inhibit or treat one or more inflammation disorders. As used hereinafter, the terms "treating," "treatment" and "therapeutic effect" can refer to reducing, inhibiting or stopping (preventing) an inflammation response (e.g., slowing or halting antibody production or amount of antibodies to a specific antigen), reducing the amount of inflamed tissue and alleviating, completely or in part, an inflammation condition. Inflammation conditions include, without limitation, allergy, asthma, autoimmune disorder, chronic inflammation, chronic prostatitis, glomerulonephritis, hypersensitivities, inflammatory bowel diseases, myopathy (e.g., in combination with systemic sclerosis, dermatomyositis, polymyositis, and/or inclusion body myositis), pelvic inflammatory disease, reperfusion injury, rheumatoid arthritis, transplant rejection, vasculitis, and leukocyte disorders (e.g., Chediak-Higashi syndrome, chronic granulomatous disease). Certain autoimmune disorders also are inflammation disorders (e.g., rheumatoid arthritis). In some embodiments, the inflammation disorder is selected from the group consisting of chronic inflammation, chronic prostatitis, glomerulonephritis, a hypersensitivity, myopathy, pelvic inflammatory disease, reperfusion injury, transplant rejection, vasculitis, and leukocyte disorder. In certain embodiments, an inflammation condition includes, but is not limited to, bronchiectasis, bronchiolitis, cystic fibrosis, acute lung injury, acute respiratory distress syndrome (ARDS), atherosclerosis, and septic shock (e.g., septicemia with multiple organ failure). In some embodiments, an inflammation condition is not a condition selected from the group consisting of allergy, asthma, ARDS and autoimmune disorder. In certain embodiments, an inflammation condition is not a condition selected from the group consisting of gastrointestinal tract inflammation, brain inflammation, skin inflammation and joint inflammation. In certain embodiments, the inflammation condition is a neutrophil-mediated disorder.

A compound described herein can be administered to a subject in need thereof to potentially treat one or more autoimmune disorders. In such treatments, the terms "treating," "treatment" and "therapeutic effect" can refer to reducing, inhibiting or stopping an autoimmune response (e.g., slowing or halting antibody production or amount of antibodies to a specific antigen), reducing the amount of inflamed tissue and alleviating, completely or in part, an autoimmune disorder. Autoimmune disorders, include, without limitation, autoimmune encephalomyelitis, colitis, autoimmmune insulin dependent diabetes mellitus (IDDM), and Wegener granulomatosis and Takayasu arteritis. Models for testing compounds for such diseases include, without limitation, (a)(i) C5BL/6 induced by myelin oligodendrocyte glycoprotein (MOG) peptide, (ii) SJL mice PLP139-151, or 178-191 EAE, and (iii) adoptive transfer model of EAE induced by MOG or PLP peptides for autoimmune encephalomyelitis; (b) non-obese diabetes (NOD) mice for autoimmune IDDM; (c) dextran sulfate sodium (DSS)-induced colitis model and trinitrobenzene sulfonic acid (TNBS)-induced colitis model for colitis; and (d) systemic small vasculitis disorder as a model for Wegener granulomatosis and Takayasu arteritis. A compound described herein may be administered to a subject to potentially treat one or more of the following disorders: Acute disseminated encephalomyelitis (ADEM); Addison's disease; alopecia greata; ankylosing spondylitis; antiphospholipid antibody syndrome (APS); autoimmune hemolytic anemia; autoimmune hepatitis; autoimmune inner ear disease; bullous pemphigoid; coeliac disease; Chagas disease; chronic obstructive pulmonary disease; Crohns disease (one of two types of idiopathic inflammatory bowel disease "IBD"); dermatomyositis; diabetes mellitus type 1; endometriosis; Goodpasture's syndrome; Graves' disease; Guillain-Barré syndrome (GBS); Hashimoto's disease; hidradenitis suppurativa; idiopathic thrombocytopenic purpura; interstitial cystitis; lupus erythematosus; mixed connective tissue disease; morphea; multiple sclerosis (MS); myasthenia gravis; narcolepsy; neuromyotonia; pemphigus vulgaris; pernicious anemia; polymyositis; primary biliary cirrhosis; rheumatoid arthritis; schizophrenia; scleroderma; Sjögren's syndrome; temporal arteritis (also known as "giant cell arteritis"); ulcerative colitis (one of two types of idiopathic inflammatory bowel disease "IBD"); vasculitis; vitiligo; and Wegener's granulomatosis. In some embodiments, the autoimmune disorder or disease is not a disorder or disease selected from the group consisting of Chrohns disease (or Chrohn's disease), rheumatoid arthritis, lupus and multiple sclerosis.

A compound described herein can be administered to a subject in need thereof to induce an immune response in the subject. The immune response may be generated automatically by the subject against a foreign antigen (e.g., pathogen infection) in certain embodiments. In some embodiments, an antigen is co-administered with a compound described herein, where an immune response is mounted in the subject against the antigen. An antigen may be specific for a particular cell proliferative condition (e.g., specific cancer antigen) or particular pathogen (e.g., gram positive bacteria wall antigen; S. aureus antigen), in certain embodiments.

A compound described herein can be administered to a subject in need thereof to potentially treat one or more cell proliferative disorders. In such treatments, the terms "treating," "treatment" and "therapeutic effect" can refer to reducing or stopping a cell proliferation rate (e.g., slowing or halting tumor growth), reducing the number of proliferating cancer cells (e.g., ablating part or all of a tumor) and alleviating, completely or in part, a cell proliferation condition. Cell proliferative conditions include, but are not limited to, cancers of the colorectum, breast, lung, liver, pancreas, lymph node, colon, prostate, brain, head and neck, skin, liver, kidney, and heart. Examples of cancers include hematopoietic neoplastic disorders, which are diseases involving hyperplastic/neoplastic cells of hematopoietic origin (e.g., arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (reviewed in Vaickus, Crit. Rev. in Oncol./Hemotol. 11:267-297 (1991)); lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In a particular embodiment, the cell proliferative disorder is non-endocrine tumor or endocrine tumors. Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor.

Cell proliferative conditions also include inflammatory conditions, such as inflammation conditions of the skin, including, for example, eczema, discoid lupus erythematosus, lichen planus, lichen sclerosus, mycosis fungoides, photodermatoses, pityriasis rosea, psoriasis. Also included are cell proliferative conditions related to obesity, such as proliferation of adipocytes, for example.

Cell proliferative conditions also include viral diseases, including for example, acquired immunodeficiency syndrome, adenoviridae infections, alphavirus Infections, arbovirus Infections, Borna disease, bunyaviridae Infections, caliciviridae Infections, chickenpox, Ccoronaviridae Infections, coxsackievirus Infections, cytomegalovirus Infections, dengue, DNA Virus Infections, eethyma, contagious, encephalitis, arbovirus, Epstein-Barr virus infections, erythema infectiosum, hantavirus infections, hemorrhagic fevers, viral, hepatitis, viral, human, herpes simplex, herpes zoster, herpes zoster oticus, herpesviridae infections, infectious mononucleosis, influenza, e.g., in birds or humans, Lassa fever, measles, Molluscum contagiosum, mumps, oaramyxoviridae Infections, phlebotomus fever, polyomavirus infections, rabies, respiratory syncytial virus Infections, Rift Valley fever, RNA Virus Infections, rubella, slow virus diseases, smallpox, subacute sclerosing panencephalitis, tumor virus infections, warts, West Nile fever, virus diseases and Yellow Fever. For example, Large T antigen of the SV40 transforming virus acts on UBF, activates it and recruits other viral proteins to Pol I complex, and thereby stimulates cell proliferation to ensure virus propagation. Cell proliferative conditions also include conditions related to angiogenesis (e.g., cancers) and obesity caused by proliferation of adipocytes and other fat cells.

Cell proliferative conditions also include cardiac conditions resulting from cardiac stress, such as hypertension, baloon angioplasty, valvular disease and myocardial infarction. For example, cardiomyocytes are differentiated muscle cells in the heart that constitute the bulk of the ventricle wall, and vascular smooth muscle cells line blood vessels. Although both are muscle cell types, cardiomyocytes and vascular smooth muscle cells vary in their mechanisms of contraction, growth and differentiation. Cardiomyocytes become terminally differentiated shortly after heart formation and thus loose the capacity to divide, whereas vascular smooth muscle cells are continually undergoing modulation from the contractile to proliferative phenotype. Under various pathophysiological stresses such as hypertension, balloon angioplasty, valvular disease and myocardial infarction, for example, the heart and vessels undergo morphologic growth-related alterations that can reduce cardiac function and eventually manifest in heart failure. Thus, provided herein are methods for treating cardiac cell proliferative conditions by administering a compound described herein in an effective amount to treat the cardiac condition. The compound may be administered before or after a cardiac stress has occurred or has been detected, and the compound or nucleic acid may be administered after occurrence or detection of hypertension, balloon angioplasty, valvular disease or myocardial infarction, for example. Administration of such a compound may decrease proliferation of vascular muscle cells and/or smooth muscle cells.

Certain embodiments also are directed to treating symptoms of aging and/or treating conditions pertaining to cell senescence by administration of a candidate molecule or nucleic acid described herein. For example, the premature aging disease of Werner Syndrome results from alterations in the Werner gene, which codes for the WRN DNA helicase. Without being limited by theory, this protein is known to localize to the nucleolus and specifically bind to G-quadruplexes, and mutations in the WRN DNA helicase result in senescence.

EXAMPLES

The examples set forth below illustrate, and do not limit, the invention.

TLR molecules can affect receptor localization, cell activation, and cytokine production. In the case of TLR4 and 9, location of TLRs is responsive to the significant profile of cytokine induction (10-12). Lipid conjugation to drugs can facilitate entry of drugs into cells via a polar lipid carrier, thereby achieving effective intracellular concentration of drugs more efficiently and with more specificity than conventional delivery systems. Conjugation of drugs to lipid, formulated with a medicinal ointment or salve, can provide penetration through skin for treatment of skin disorders. PEGylation can prolong blood circulation of drugs by increasing stability in vivo that in turn leads to decreased toxicity (13). Here, lipid and polyethylene glycol were conjugated to a TLR7 agonist (SM), and immune activity of the conjugates were tested. Individual TLR7 agonist conjugates presented distinct immunostimulatory profiles in vivo and in vitro. Conjugation of the TLR7 agonist to lipid improved ability to stimulate innate immunity compared to unconjugated TLR7 agonists (SM). Lipid-TLR7 agonist conjugates showed quick onset and long lasting adjuvant effect in vivo. These data suggest lipid-TLR7 conjugates have a potential application as adjuvants for therapeutic vaccination. Conjugation of the TLR7 agonist to PEG, however, modified the properties of the SM pharmacophore and the conjugate, instead, exhibited TLR7 antagonist activity.

Example 1

Synthesis and Characterization of Conjugates

Materials 1,2-Dioleoyl-sn-glycero-3-phosphoethanolamine (DOPE) was purchased from Avanti Polar Lipids (Alabaster, Ala.). All other reagents and were purchased as at least reagent grade from Sigma-Aldrich (St. Louis Mo.) without further purification. Solvents were purchased from Fischer Scientific (Pittsburgh, Pa.) and were either used as purchased or redistilled with an appropriate drying agent. Ovalbumin (OVA, grade V) was purchased from Sigma-Aldrich.

Endotoxin levels in the reagents and conjugates for experiments of immunological activities were measured using the QCL1000® Endpoint chromogenic LAL assay purchased from BioWhittaker (Walkerville, Md., USA). Reagents that contained less than 1 picogram (pg) endotoxin per microgram (µg) protein or drug were used throughout the experiments. Since DOPE gave false positive results in the LAL assay, bone marrow derived mononuclear (BMDM) cells derived from liposaccharides unresponsive mutant mice (C3H/HeJ) were used to test contamination by endotoxin (see FIG. 1B). The levels of cytokine production by BMDM derived from C3H/HeJ mice were similar to the levels in cells derived from the wild type C3H/HeOuJ strain, indicating that endotoxin contamination was negligible (see FIG. 2B). All conjugates were stored at −80° C. in dry powder. The conjugates were dissolved in DMSO at 100 mM and further diluted before immunological assays.

Analytical TLC was performed using precoated TLC silica Gel 60 F254 aluminum sheets purchased from EMD (Gibbstown, N.J.) and visualized using UV light. Flash chromatography was carried out on EMD silica gel 60 (40-63 µm) using the specified solvent system. Chromatography and mass spectra (ESI) for compounds without lipids were recorded on an 1100 LC/MSD (Agilent Technologies, Inc., Santa Clara Calif.) with a Supelco DISCOVERY HS C18 column (Sigma-Aldrich) with purity above 98% by percent area. Mass spectra (ESI) of lipid containing compounds were recorded on a Finnigan LCQDECA (Thermo Fisher Scientific Inc. Waltham, Mass.). 1H NMR spectra were obtained on a Varian Mercury Plus 400 (Varian, Inc., Palo Alto Calif.). The chemical shifts are expressed in parts per million (ppm) using suitable deuterated NMR solvents in reference to TMS at 0 ppm.

C57BL/6 (B6) mice were purchased from Charles River Laboratories (Wilmington, Mass.). C3H/HeJ and C3H/HeOuJ mice were purchased from The Jackson Laboratories (Bar Harbor, Me.). TLR7 deficient mice (C57BL/6 background) were a gift from Dr. S. Akira, (Osaka University, Osaka, Japan) and were backcrossed ten generations onto the C57BL/6 background. Animals were bred and maintained at UCSD in rooms at 22±0.5° C. on a 12:12-h light-dark cycle from 7 am to 7 pm. All procedures and protocols were approved by the Institutional Animal Care and Use Committee.

Chemical Syntheses

Figure 2A:
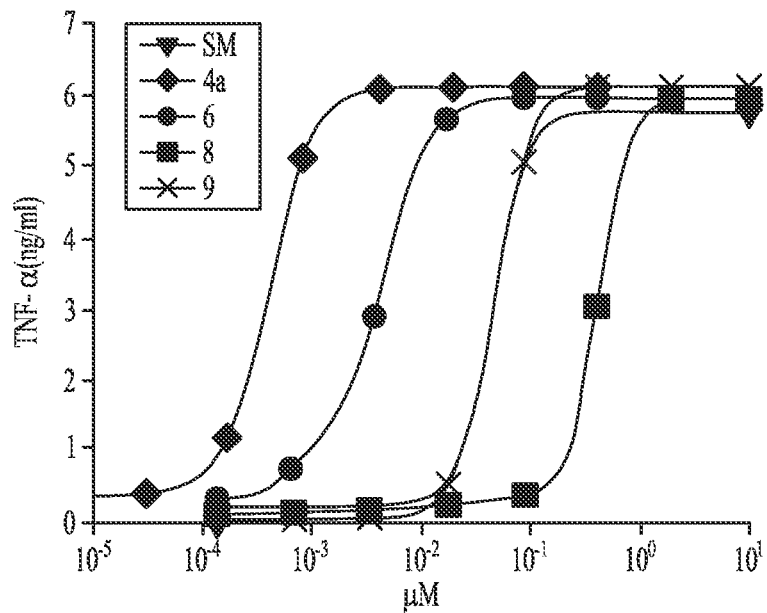
FIGS. 2A-D depict the results of in vitro immunological characterization of TLR7 conjugates in murine macrophages.
Figure 2B:
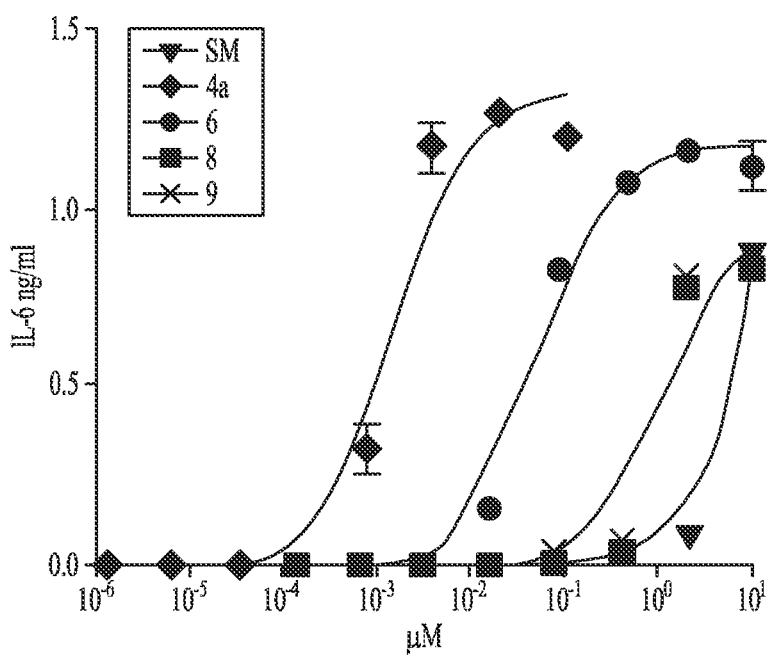
Figure 2C:
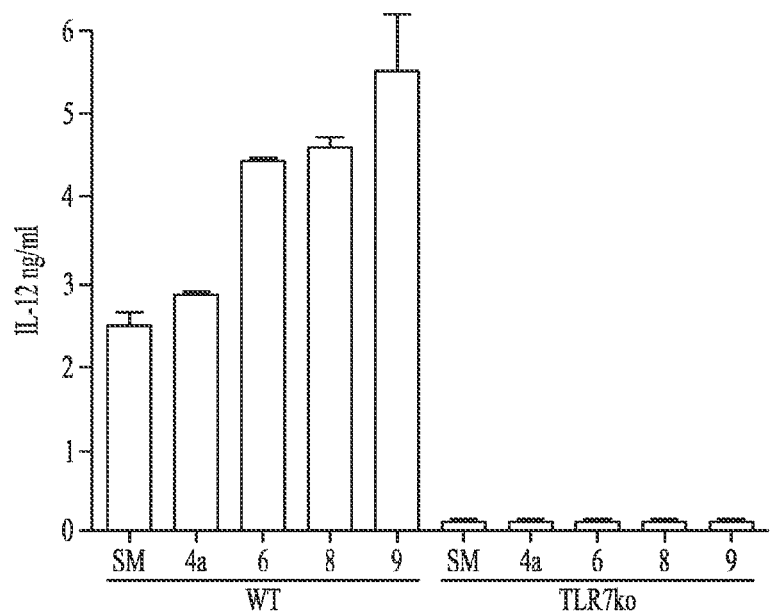
Figure 2D:
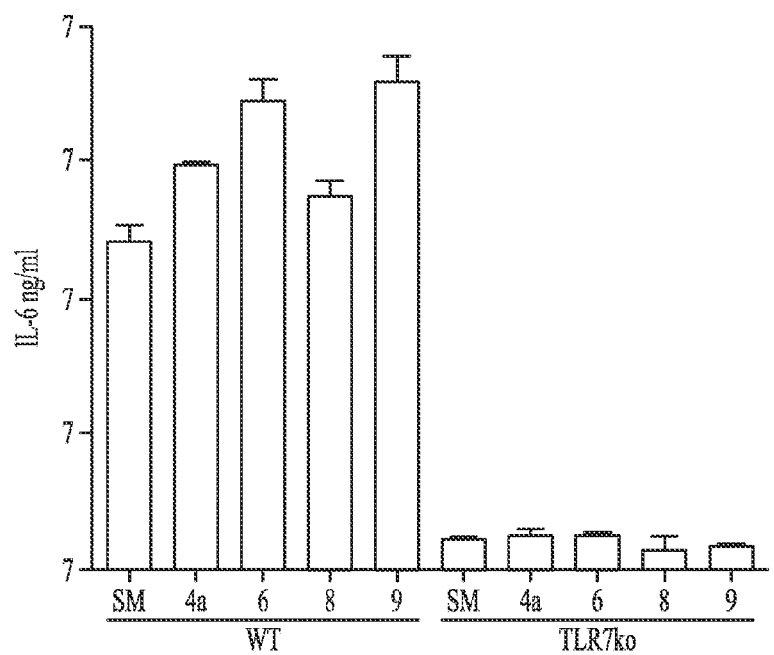
Figure 2E:
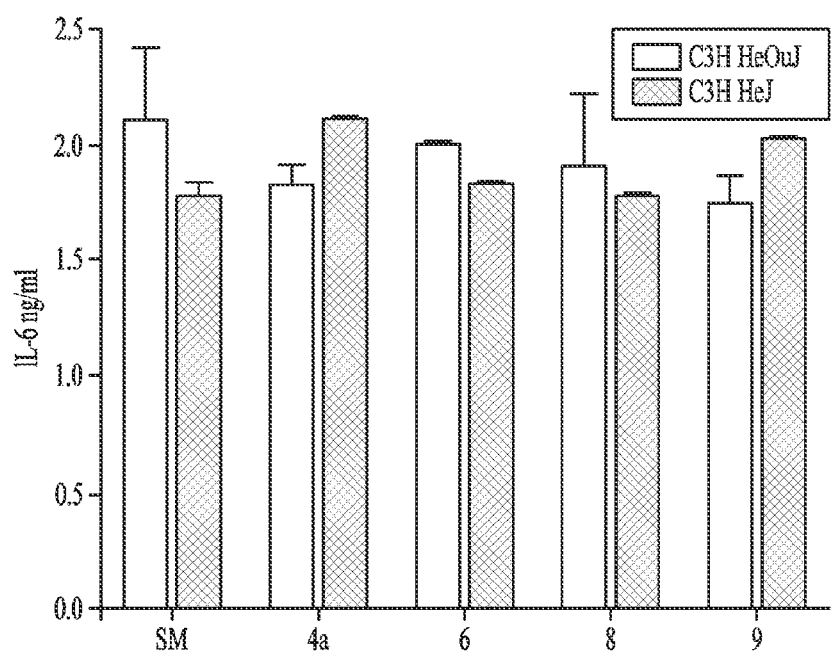
FIG. 2E depicts the results of evaluation of endotoxin contamination using LPS unresponsive mutant and wild type macrophages.

Chemical synthesis schemes described herein use numbers in parenthesis when referring to a compound in FIG. 1, and letters in parenthesis when referring to a reaction step (e.g., chemical(s) added and/or reaction conditions). For example, (a) refers to a reaction step that includes the addition of a reactant, which may result in the formation of compound (2), when combined and reacted with compound (1). The reaction conditions and compounds added for each reaction step are; (a) Lithium N,N'-methylethylenediaminoaluminum hydrides (Cha, J. et al., (2002) Selective conversion of aromatic nitriles to aldehydes by lithium N,N'-dimethylethylenediaminoaluminum hydride, Bull. Korean Chem. Soc. 23, 1697-1698), THF, 0° C.; (b) NaI, chlorotrimethylsilane, $CH_3CN$, r.t.; (c) PBS, r.t.; (d) NaOH:EtOH 1:1, reflux; (e) DOPE, HATU, triethylamine, DMF/DCM 1:1, r.t.; (f) O-(2-Aminoethyl)-O'-(2-azidoethyl)nonaethylene glycol, HATU, triethylamine, DMF, r.t.; (g) 4 pentynoic acid, sodium ascorbate, Cu $(OAc)_2$, t-BuOH/$H_2O$/THF 2:2:1, r.t.; and (h) DOPE, HATU, triethylamine, DMF/DCM 1:1, r.t.

Synthesis of 4-((6-amino-2-(2-methoxyethoxy)-8-oxo-7H-purin-9(8H)-yl)methyl)benzoic acid (see FIG. 1, compound 5). 20 mL of a 1:1 ethanol:water mixture was added to 0.10 g (0.28 mmol) of 4-((6-amino-8-methoxy-2-(2-methoxyethoxy)-9H-purin-9 yl)methyl)benzonitrile (see FIG. 1, compound 1), and the combination refluxed for 8 hours. The reaction mixture was allowed to cool and acidified to pH 2 with conc. HCl. The aqueous solution was further extracted with DCM (3×20 mL), dried over MgSO4 and evaporated in vacuo to yield a mixture of 8-oxo-9-benzoic acid (compound 5), 8-methoxy-9-benzoic acid and 8-oxo-9-ethyl benzoate. Once dried, the products were dissolved in $CH_3CN$ (25 mL) and NaI (0.14 g, 0.96 mmol) was added (FIG. 1, reaction step (b)). To this solution was added 12 µL (0.96 mmol) of chlorotrimethylsilane, dropwise with stirring. The reaction mixture was heated at 40° C. for 4 hours then cooled, filtered and washed with water (20 mL) and then diethyl ether (20 mL) to obtain a white solid in 85% yield. Nuclear Magnetic Resonance (NMR) analysis was performed on the resultant product, with the following results, $^1$H NMR (400 MHz, DMSO-$d_6$) δ (ppm): 10.33 (s, 1H), 7.89 (d, J=8 Hz, 2H), 7.37 (d, J=8 Hz, 2H), 6.65 (s, 2H), 4.92 (s, 2H), 4.24 (t, J=4 Hz, 2H), 3.56 (t, J=4 Hz, 2H), 3.25 (s, 3H). Retention time (Rt) on HPLC=14.3 min. ESI-MS (positive ion mode): calculated for $C_{16}H_{17}N_5O_5$ m/z [M+1] 360.34; found 360.24.

Synthesis of 2-(4-((6-amino-2-(2-methoxyethoxy)-8-oxo-7H-purin-9(8H)-yl)methyl)benzamido)ethyl 2,3-bis(oleoyloxy)propyl phosphate (see FIG. 1, compound 6). To a solution of 0.022 g (0.06 mmol) of compound 5 in 1 mL of anhydrous N,N-dimethylmethanamide (DMF) was added O-(7-azabenzotriazol-1-yl)-N,N,N',N'-tetramethyluronium hexafluorophosphate (HATU) (0.026 g, 0.067 mmol) and anhydrous triethylamine (TEA) (17.0 μL, 0.12 mmol). A solution of 1,2-Dioleoyl-sn-glycero-3-phosphoethanolamine (0.05 g, 0.067 mmol) in anhydrous 1:1 dichloromethane (DCM):DMF (1 mL) was prepared and slowly added to the reaction mixture (FIG. 1 reaction step (e)). The reaction mixture was stirred at room temperature until completion and then evaporated in vacuo. The product was purified by flash chromatography using 15% methanol (MeOH) in DCM to give 0.038 g of white solid in 58% yield. NMR analysis was performed on the resultant product, with the following results, $^1$H NMR (400 MHz, DMSO-d$_6$) δ (ppm): 9.7 (s, 1H), 7.87 (d, J=8.3 Hz, 2H), 7.32 (d, J=8.3 Hz, 2H), 6.61 (s, 2H), 5.30 (m, 4H), 5.05 (m, 1H), 4.88 (s, 2H), 4.26 (m, 4H), 4.06 (m, 1H), 3.77 (m, 4H), 3.57 (m, 2H), 3.35 (m, 2H), 3.26 (s, 3H), 2.23 (m, 4H), 1.95 (m, 8H), 1.46 (m, 4H), 1.22 (m, 40H), 0.83 (m, 6H). ESI-MS (negative ion mode): calculated for $C_{57}H_{92}N_6O_{12}P$ m/z [M−1] 1083.35; found 1083.75.

Synthesis of 4-((6-amino-8-hydroxy-2-(2-methoxyethoxy)-9H-purin-9-yl)methyl)-N-(32-azido-3,6,9,12,15,18,21,24,27,30-decaoxadotriacontyl)benzamide (see FIG. 1, compound 7). To a solution of compound 5 (0.100 g, 0.278 mmol) in anhydrous DMF (5 mL) was added HATU (0.117 g, 0.306 mmol) and anhydrous TEA (77.014 μL, 0.556 mmol) (see FIG. 1, reaction step (f)). A solution of O-(2-aminoethyl)-O'-(2-azidoethyl)nonaethylene glycol (0.150 g, 0.306 mmol) in anhydrous DMF (1 mL) was prepared and slowly added to the reaction mixture. The reaction mixture was stirred at room temperature until completion and then evaporated in vacuo. The product was purified by flash chromatography using 5% MeOH in DCM to give 0.224 g of an opaque oil in 93% yield. Retention time on HPLC=12 min. NMR analysis was performed on the resultant product, with the following results, $^1$H NMR (400 MHz, DMSO-d$_6$) δ (ppm): 10.01 (s, 1H), 8.45 (t, J=5.6 Hz, 1H), 7.78 (d, J=8.3 Hz, 2H), 7.35 (d, J=8.3 Hz, 2H), 6.49 (s, 2H), 4.90 (s, 2H), 4.25 (t, J=4 Hz, 2H), 3.57 (m, 4H), 3.5 (m, 36H), 3.4 (M, 6H), 3.26 (s, 3H). ESI-MS (positive ion mode): calculated for $C_{38}H_{61}N_9O_{14}$ m/z [M+1] 868.94; found 868.59.

Synthesis of 3-(1-(1-(4-((6-amino-8-hydroxy-2-(2-methoxyethoxy)-9H-purin-9-yl)methyl)phenyl)-1-oxo-5,8,11,14,17,20,23,26,29,32-decaoxa-2-azatetratriacontan-34-yl)-1H-1,2,3-triazol-4-yl)propanoic acid (see FIG. 1, compound 8). Compound 7 (0.218 g, 0.251 mmol) and 4-pentynoic acid (0.074 g, 0.753 mmol) were dissolved in 1:1 t-butanol:H2O (3 mL) (see FIG. 1, reaction step (g)). Sodium ascorbate (0.02 g, 100 mmol) and Cu(OAc)$_2$ (0.009 g, 50 mmol) in 1:1 t-butanol:H2O (1 mL) was slowly added to the reaction mixture and stirred at room temperature until compound 7 was fully reacted by TLC. The product was extracted with DCM (10 mL) and H2O (10 mL) and the organic layer was dried over MgSO$_4$ to give 0.230 g of an opaque oil in 95% yield. Retention time on HPLC=11.5 min. NMR analysis was performed on the resultant product, with the following results, $^1$H NMR (400 MHz, DMSO-d$_6$) δ (ppm): 13.48 (s, 1H), 7.76 (d, J=8.29 Hz, 2H), 7.75 (s, 1H), 7.23 (d, J=8.29, 2H), 4.88 (s, 2H), 4.41 (t, J=5.12 Hz, 2H), 4.23 (t, J=4 Hz, 2H), 3.74 (t, J=5.12 Hz, 2H), 3.57 (t, J=4 Hz, 2H), 3.51 (m, 8H), 3.42 (m, 36H), 3.26 (s, 3H), 2.79 (t, J=7.56 Hz, 2H), 2.24 (t, J=7.56 Hz, 2H). ESI-MS (positive ion mode): calculated for $C_{43}H_{67}N_9O_{16}$ m/z [M+1] 966.04; found 966.67.

Synthesis of 2-(3-(1-(1-(4-((6-amino-8-hydroxy-2-(2-methoxyethoxy)-9H-purin-9-yl)methyl)phenyl)-1-oxo-5,8,11,14,17,20,23,26,29,32-decaoxa-2-azatetratriacontan-34-yl)-1H-1,2,3-triazole-4-yl)propanamido)ethyl 2,3-bis(oleoyloxy)propyl phosphate (see FIG. 1, compound 9). To a solution of compound 8 (96 mg, 0.1 mmol), HATU (42 mg, 0.11 mmol) in anhydrous DMF (1 mL) was added anhydrous TEA (2.7 μL, 0.2 mmol). A solution of DOPE (81.4 mg, 0.11 mmol) in 1:1 DCM:DMF (1 mL) was added dropwise to the reaction mixture and stirred at room temperature until completion (see FIG. 1, reaction step (h)). Upon completion the product was isolated by evaporation in vacuo followed by flash chromatography using 15% MeOH in DCM to give 155 mg of opaque oil in 92% yield. NMR analysis was performed on the resultant product, with the following results, $^1$H NMR (400 MHz, DMSO-d$_6$) δ (ppm): 8.5 (s, 2H), 8.39 (s, 1H), 7.79 (m, 3H), 7.33 (d, J=6.23 Hz, 2H), 6.91 (s, 2H), 5.31 (m, 4H), 5.05 (m, 1H), 4.89 (s, 2H), 4.46 (m, 2H), 4.23 (m, 4H), 4.08 (t, J=8 Hz, 2H), 3.76 (m, 4H), 3.63 (t, J=8 Hz, 2H), 3.56 (t, J=8 Hz, 2H), 3.48 (m, 36H), 3.26 (m, 5H), 3.17 (m, 2H), 2.82 (t, J=8 Hz, 2H), 2.39 (t, J=8 Hz, 2H), 2.24 (m, 4H), 1.96 (m, 8H), 1.48 (m, 4H), 1.23 (m, 40H), 0.84 (m, 6H). ESI-MS (positive ion mode): calculated for $C_{84}H_{142}N_{10}O_{23}P$ m/z [M+1] 1691.05; found 1692.82.

Other compounds were synthesized using similar techniques (e.g., compounds shown in Table 2). For example, 4-((6-amino-8-hydroxy-2-(2-methoxyethoxy)-9H-purin-9-yl)methyl0-N-hexadecylbenzamine (compound 1Z7) and 4-((6-amino-8-hydroxy-2-(2-methoxyethoxy)-9H-purin-9-yl)methyl0-N,N-dihexadecylbenzamine (compound 1Z9), were prepared and purified as described above for the preparation of compound 6 in FIG. 1, except that the respective mono- and di-substituted hexadecylamines were used instead of 1,2-dioleoyl-sn-glycero-3-phosphoethanolamine. A mass of 583.7 was observed for compound 1Z7 using ESI-MS (positive ion mode; calculated mass for $C_{32}H_{60}N_6O_4$ m/z [M+1] is 582.78). A mass of 808.2 was observed for 1Z9 using ESI-MS (positive ion mode; calculated mass for $C_{48}H_{82}N_6O_4$ m/z [M+1] is 807.20).

Biotinylated derivative N-(4-((6-amino-8-hydroxy-2-(2-methoxyethoxy)-9H-purin-9-yl)benzyl)-5-((3aS,4S,6aR)-2-oxohexahydro-1H-thieno[3,4-d]imidazol-4-yl)pentanamide (compound 1Z18) was prepared from the aminomethyl derivative (1V184) and was conjugated to biotin using the same procedure as described above. A mass of 571.5 was observed using ESI-MS (positive ion mode; calculated mass for $C_{26}H_{34}N_8O_5S$ m/z [M+1] is 570.66).

Experimental Methods

In Vitro Methods

In vitro measurements of cytokine induction were performed using the mouse leukemic monocyte macrophage cell line, RAW264.7. Raw264.7 mice were obtained from the American Type Culture Collection (ATCC, Rockville, Md.) and cultured in DMEM complete media [Dulbecco's Modified Eagle Medium (Irvine Scientific, Irvine, Calif.) supplemented with 10% heat-inactivated fetal calf serum, 2 mM L-glutamine, and 100 U/mL penicillin/100 μg/mL streptomycin]. BMDM were prepared from C57BL/6 and TLR7 deficient mice as described in Wu, C. C et al., (2007) "Immunotherapeutic activity of a conjugate of a Toll-like receptor 7 ligand", Proc Natl Acad Sci USA 104, 3990-5.

In general, RAW264.7 cells or BMDM were incubated with various concentrations of conjugates for 18 hours at 37° C., 5% CO2 and culture supernatants were collected. The levels of cytokines (IL-6, IL-12 or TNF-α in the supernatants were determined by ELISA (BD Biosciences Pharmingen, La Jolla, Calif.) (Cho, H. J et al., "Immunostimulatory DNA-based vaccines induce cytotoxic lymphocyte activity by a T-helper cell-independent mechanism" [see comments], Nat Biotechnol 18, 509-14 (2000)), and the results presented in FIG. 2A-D. Data are mean±SEM of triplicates and are representative of three independent experiments. Minimum detection levels of these cytokines were 15 pg/mL.

TNFα levels were measured (see FIG. 2A) by incubating approximately 1×10$^6$/mL RAW 264.7 cells with the various conjugates or controls, as described above. IL-6 and IL12 levels were measured (see FIG. 2B-D) by incubating 0.5×10$^6$/mL BMDM with the various conjugates or controls, as described above. Conjugates were prepared as stock solutions (10 μm for SM, and compounds (6), (8), and (9), 0.1 μm for compound (4a)), and serial dilutions (1:5) prepared therefrom.

BMDM were also used to evaluate the level of endotoxin contamination of TLR7 conjugates synthesized using synthesis schemes described herein. 0.5×10$^6$/mL BMDM derived from C3H/HeJ (LPS unresponsive mutant) or C3H/HeOuJ (wild type) were incubated with TLR7 conjugates (10 μM SM, 0.1 μM compound 4a, 10 μM compound 6, 10 μM compound 8 or 10 μM compound 9) for 18 hours. IL-6 or IL-12 levels in culture supernatants were measured by ELISA, and the results presented in FIG. 2B. Each of the TLR7 conjugates induced similar levels of IL-6 both in TLR4 mutant and wild type mice, indicating LPS contamination of these conjugates is minimal.

Human blood peripheral mononuclear cells (PBMC) were isolated from human buffy coats, purchased from The San Diego Blood Bank (San Diego, Calif.), as described in Hayashi, T et al., "Enhancement of innate immunity against *Mycobacterium avium* infection by immunostimulatory DNA is mediated by indoleamine 2,3-dioxygenase", Infect Immun 69:6156-64, (2001). PBMC (1×10$^6$/mL) were incubated with various concentrations of TLR7 conjugates for 18 hours at 37° C., 5% $CO_2$ and culture supernatants were collected. The levels of cytokines (IL-6, TNF-α, or IFNα1) in the supernatants were determined by LUMINEX bead assays (Invitrogen, Carlsbad, Calif.), and the results presented in FIG. 3A-B. Data are mean±SEM of triplicates and are representative of three independent experiments. The minimum detection levels of IL-6, TNF-α, and IFNα1 were 6 pg/mL, 10 pg/mL and 15 pg/mL, respectively.

In Vivo Methods

The pharmacokinetics of pro inflammatory cytokine induction by TLR7 conjugates was examined using 6- to 8-week old C57BL/6 mice. The mice were intravenously injected with TLR7 agonists and their conjugates (40 nmol compound (4a) or 200 nmol SM and compounds (6), (8), or (9) per mouse). Blood samples were collected 2, 4, 6, 24 or 48 hours after injections. Sera were separated and kept at −20° C. until use. The levels of cytokines (e.g. IL-6 and TNF-α 1n the sera were measured by LUMINEX bead microassay, and the results presented in FIG. 4A-B. Data are mean±SEM of five mice and are representative of two independent experiments. The minimum detection levels of IL-6 and TNF-α are 5 pg/mL and 10 pg/mL, respectively.

Immunological reaction initiation (e.g. adjuvanticity) by TLR7 conjugates was also examined. Groups (n=5) of C57BL/6 mice were subcutaneously immunized with 20 μg ovalbumin (OVA) mixed with approximately 10 nmol of various TLR7 conjugates, on days 0 and 7, where 10 nmol is a dosage target for the TLR7 portion of the conjugate, and the actual amount will be dependent on the actual chemical formula of each conjugate. A TLR9-activating immunostimulatory oligonucleotide sequence (ISS-ODN; 1018) was used as a positive control for a Th1 inducing adjuvant (Roman, M et al., Immunostimulatory DNA sequences function as T helper-1-promoting adjuvants (1997), Nat Med 3:849-54). Sera were collected on days 0, 7, 14, 21, 28, 42 and 56. Mice immunized with saline or OVA mixed with vehicle served as controls. Mice were sacrificed on day 56 and the spleens were harvested for preparation of splenocytes and histological slides.

Approximately 200 microliters of a 2.5×10$^6$/mL spleen cell stock were aliquoted into round-bottom tissue culture microtiter plates in triplicate in a total volume of 200 μl RPMI 1640 complete medium [RPMI1640 (Irvine Scientific, Irvine, Calif.) supplemented with 10% heat-inactivated FCS, 2 mM L-glutamine, and 100 U/mL penicillin/100 μg/mL streptomycin] and restimulated with either 100 μg/mL OVA or medium alone. In some experiments the site of injection was examined 24 hours after immunization for signs of inflammation or local reaction. Mice were observed for activity as measures of a potential "sickness" response to immunization and then weighed weekly. In addition to spleen harvesting, lungs, livers, hearts, and kidneys also were collected on day 56, fixed in 10% buffered Formalin (Fisher Scientific, Pittsburgh, Pa.) and embedded in paraffin. Sections 5 μm thick were stained with hematoxylin and eosin (H&E) and evaluated under the microscope.

Anti-OVA antibodies of the IgG subclasses (and in some embodiments specifically IgG1 and IgG2) were measured by ELISA, as described in Cho, H. J et al., "Immunostimulatory DNA-based vaccines induce cytotoxic lymphocyte activity by a T-helper cell-independent mechanism" [see comments], Nat Biotechnol 18, 509-14 (2000), and the results presented in FIGS. 5A and 5B. Each ELISA plate contained a titration of a previously quantitated serum to generate a standard curve. The titer of this standard was calculated as the highest dilution of serum that gave an absorbance reading that was double the background. The various sera samples were tested at a 1:100 dilution. The results are expressed in units per mL, calculated based on the units/mL of the standard serum, and represent the mean±SEM of five animals in each group. * and † denote $P<0.05$ and $P<0.01$ by One-way ANOVA compared to the mice immunized with OVA mixed with vehicle, respectively.

Spleenocytes were prepared from the harvested spleens. Spleenocyte cultures (restimulated either 100 μg/mL OVA or medium alone) were then incubated at 37° C., 5% $CO_2$ and supernatants harvested after 72 hours. The levels of IFNγ in the culture supernatants were measured by ELISA (BD Bioscience PharMingen) as per the manufacturer's instructions (Kobayashi, H et al., Prepriming: a novel approach to DNA-based vaccination and immunomodulation", Springer Semin Immunopathol 22:85-96 (2000), and the results illustrated in FIG. 5C. Average total spleen cell number in each group were calculated and compared to the PBS-immunized groups to monitor the spleen cell proliferation. Data are mean±SEM of five mice and are representative of three independent experiments.

Figures 6A, 6B:
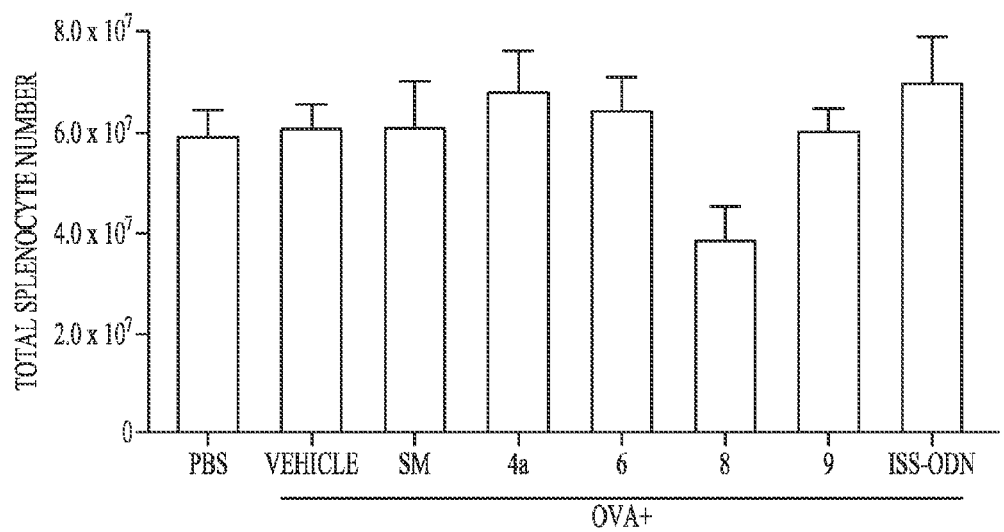
FIGS. 6A-C depict the results of evaluation of possible adverse effects of TLR7 conjugates.
Figure 6C:
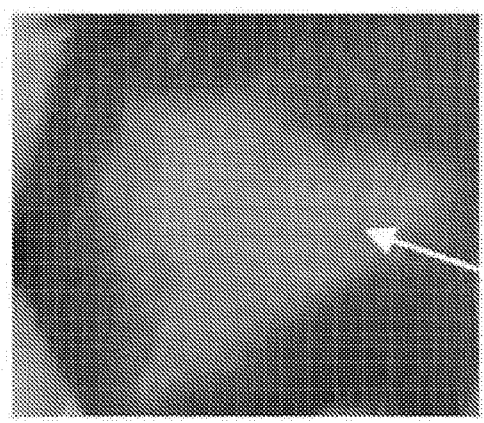
Figure 6C:
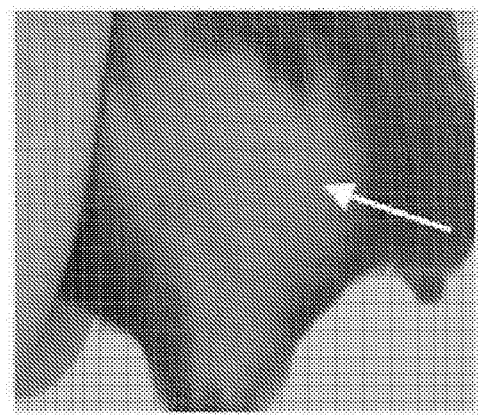

Evaluation of possible adverse effects of TLR7 conjugates was performed by a three-fold analysis (counting of total spleenocytes, histological examination, and visual observation of both the area of injection and general overall health and behavior of treated mice). C57BL/6 mice were immunized with 20 μg OVA mixed with TLR7 conjugate, vehicle, or a control agonist (oligonucleotide sequence ISS-ODN). On day 56, mice were sacrificed and number of total spleenocytes was counted, and the results presented in FIG. 6A. The spleens were collected and submitted to the histological examination, as shown in FIG. 6B (magnification factor=100×). The skin of injection sites is inspected 24 hours after injection, as shown in FIG. 6C. There is no significant difference in the number of splenocytes counted between mice immunized with OVA plus TLR7 conjugates and the mice immunized with OVA alone (see FIG. 6A). Histological examination of the spleens from mice immunized with OVA mixed with TLR7 conjugates did not show any disruption of the white pulps or increased cellularity in red pulp (see FIG.

Figure 7A:
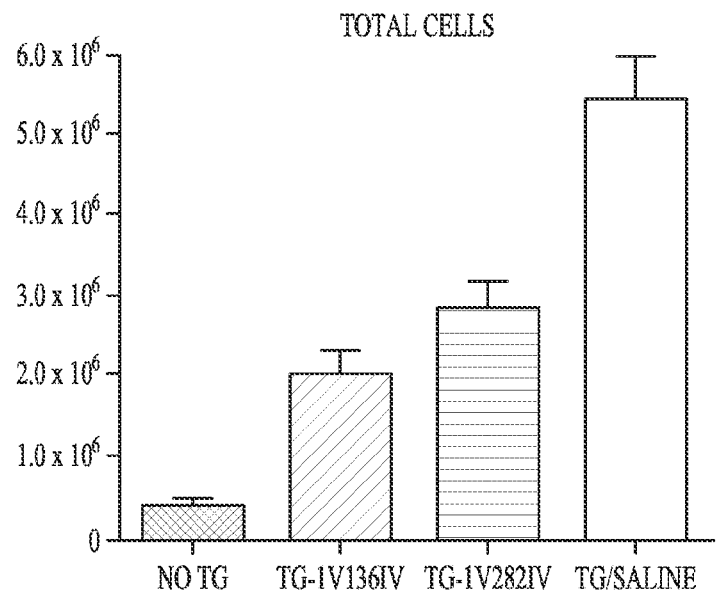
FIGS. 7A-B illustrate a reduction of peritoneal neutrophil infiltration by treatment with 1V136 (free pharmacophore) and 1V282 (compound 8).
Figure 7B:
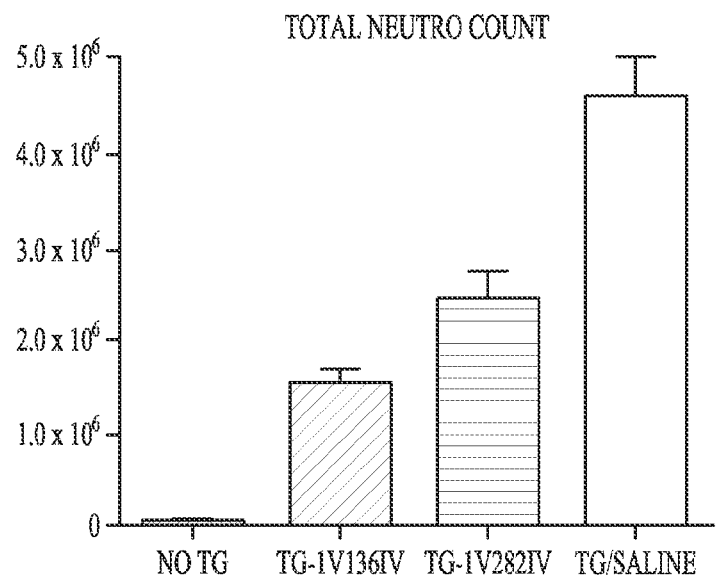

6B). The skin of injection sites did not have visible redness or glaucomatous reaction (see FIG. 6C). Efficacy of treatment with compound (8) was evaluated by measurement of the reduction of number of neutrophils invading the peritoneum of treated mice and also by the effect on induced experimental autoimmune encephalomyelitis (EAE). Reduction of peritoneal neutrophil infiltration was measured by treating C57BL/6 mice with intravenous injections (i.v.) of 50 nmoles of the free pharmacophore (1V136) or compound (8) for three days. 2 ml 3% thioglycolate (TG) were injected intraperitoneally (i.p.) 18 hours after the last compound injection in order to induce neutrophil recruitment. Peritoneal cells were collected four hours after TG injection. Total cells were counted by haematocytometer and neutrophils were morphologically identified. The results are presented in FIGS. 7A and 7B.

The effect of compound (8) on experimental autoimmune encephalomyelitis (EAE) was determined using C57BL/6 mice treated with myelin oligodendrocyte glycoprotein (MOG). MOG is a membrane protein expressed on the oligodendrocyte cell surface and the outermost surface of myelin sheaths. MOG is an auto-antigen protein that when destroyed can result in a disease characterized by the demyelination of neurons, similar to symptoms associated with Multiple Sclerosis, for example. MOG has been shown to be highly encephalitogenic and can induce strong T and B cell responses, in rodents. EAE is an inflammatory demyelinating disease of the central nervous system (CNS), and is widely studied as an animal model of the human CNS demyelinating diseases, including the diseases multiple sclerosis and acute disseminated encephalomyelitis (ADEM), as well as being useful brain inflammation studies.

Figure 8:
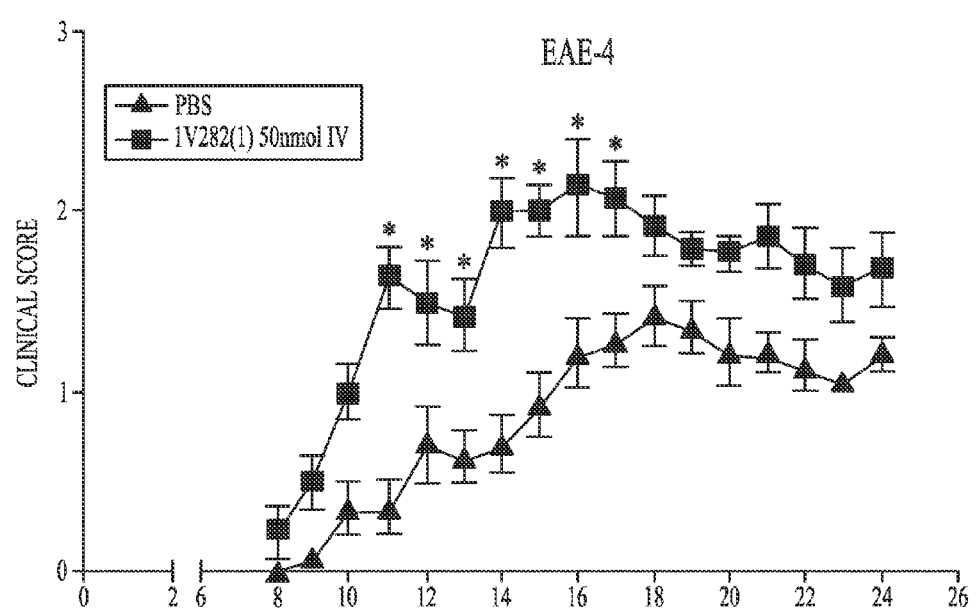
FIG. 8 illustrates the effect of treatment with 1V282 (compound (8)) on induced experimental autoimmune encephalomyelitis (EAE).

Treatment with MOG (or MOG peptides) may be used to induce EAE. Mice were treated with MOG protein for 6 days. On day 6 and onward (see FIG. 8), 50 nmoles of compound (8) or PBS were intravenously (i.v.) injected everyday. EAE clinical scores were used as a clinical metric for demyelination and were determined visually. Statistically significant clinical scores were observed on days 11-17 of compound (8) treatment as indicated on FIG. 8 (see data points with * above them)

In some experiments statistical evaluation was performed to determine the statistical significance of the observed results. A statistical software package (Prism 4.0, GraphPad, San Diego Calif.) was used for statistical analyses including regression analysis. Data were plotted and fitted by non-linear regression assuming a Gaussian distribution with uniform standard deviations between groups. In the adjuvanticity experiments, the statistical difference between the groups were analyzed by two way ANOVA with Bonferroni post-tests to compare control mice with those that were immunized with OVA. A value of $P<0.05$ was considered statistically significant.

Results and Discussion
Chemical Synthesis

The synthesis of compound (4) from compound (1) yielded a consistent conjugation ratio of 5:1 UC1V150 to MSA protein (Wu, C. C et al., "Immunotherapeutic activity of a conjugate of a Toll-like receptor 7 ligand", Proc Natl Acad Sci USA 104, 3990-5 (2007)). Basic hydrolysis (FIG. 1, reaction step (d)) of the 9-benzylnitrile of compound (1) provided a versatile benzoic acid functional group (compound (5)) and allows for the assembly of conjugates (6), (8), and (9). The benzoic acid was coupled with DOPE by activation with HATU in the presence of TEA in anhydrous DMF (FIG. 1, reaction step (e)) to give compound 6 in 58% yield.

Due to the difficulty in dissolution of compound (6) in suitable solvents for testing, a PEG spacer was coupled to provide improved solubility. A readily available amine/azide bifunctional PEG was coupled to the benzoic acid by activation with HATU in the presence of TEA in anhydrous DMF (see FIG. 1, reaction step (f), which results in compound (7)). The formation of a 1,2,3-triazole through a copper(I)-catalyzed azide-alkyne cycloaddition with 4-pentynoic acid (FIG. 1, reaction step (g)) gave compound (8) in 95% yield. Finally, compound (9) was prepared by HATU activated amide formation with DOPE (FIG. 1, reaction step (h)) and compound (8).

In vitro measurement of cytokine induction by lipid-conjugated TLR7 agonists TLR7 agonist compound (4a), when covalently coupled with mouse serum albumin, exhibited a potency of 10 or higher in cytokine induction in vitro and in vivo compared to unconjugated drug (SM) (Wu, C. C et al., "Immunotherapeutic activity of a conjugate of a Toll-like receptor 7 ligand", Proc Natl Acad Sci USA 104, 3990-(2007)). Using a similar assay, the in vitro potency of the lipid-TLR agonist conjugates (FIG. 1, compound 6), PEG-TLR7 agonist conjugates (FIG. 1, compound 8), and PEG-lipid (FIG. 1, compound 9) conjugates were compared using a murine macrophage cell line, RAW264, and primary bone marrow derived macrophages (BMDM). The respective cells were stimulated for 18 hours with serially diluted TLR7 conjugates and the levels of cytokines released in the media were measured by ELISA and compared to the unconjugated TLR7 agonist (SM) (see FIG. 2A, panels A-D).

Compound (4a) (e.g., a TLR7-MSA conjugate) was previously shown to be 100-fold more potent as a cytokine inducer, when compared to the unconjugated agonist, whereas the Lipid-TLR7 conjugate was 10-fold more potent, when normalized to the molar level of the unconjugated agonist. Although the PEG-TLR7 conjugates (compound 8) showed less potency compared to the unconjugated TLR7 (SM), conjugation of lipid to PEG-TLR7 conjugates (lipid PEG-TLR7) (compound 9) restored their potency to the similar level of the unconjugated TLR7 (SM). Substantially similar concentrations of MSA, lipid or PEG without TLR7 conjugation, at the highest levels in the conjugated form, were used as a negative control and induced minimal or no cytokine levels in RAW264.7 cells and BMDM, respectively (data not shown).

In order to evaluate if the conjugated forms of TLR7 agonists were solely inducing macrophage stimulation, as opposed to non-TLR7 macrophage stimulation, BMDM derived from wild type and TLR7 deficient mice (TLR7-KO or knock out mice) were treated with compounds (4a), (6), (8), (9) and SM. Compounds (4a), (6), (8), (9) and SM, induced little or no IL-12 and IL-6 whereas these conjugates were active in wild type BMDM, indicating the agonist activity was due to the TLR7 activity of these conjugates (see FIG. 2C-D). Endotoxin evaluation (FIG. 2B, and described above) further supported the conclusion that the agonist activity was due to the TLR7 activity of these conjugates (e.g., no significant statistical difference in the levels of IL-6 produced).

Figure 3A:
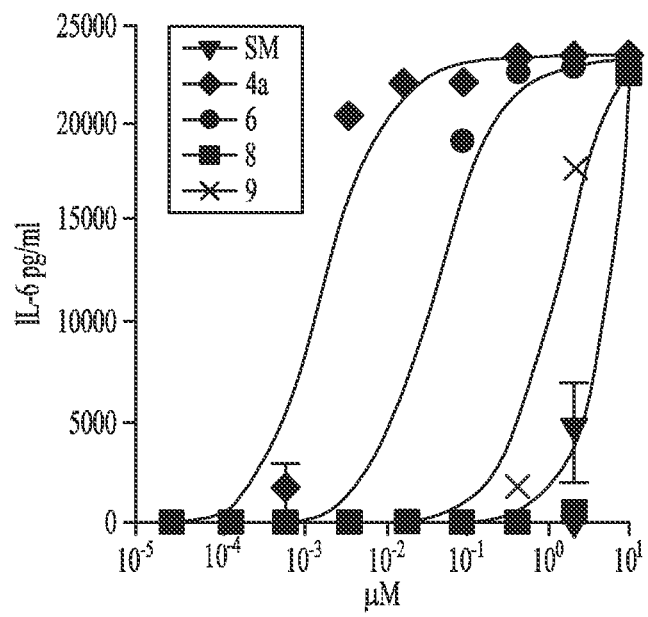
FIGS. 3A-B depict the results of in vitro immunological characterization of TLR7 conjugates in human PBMC.
Figure 3B:
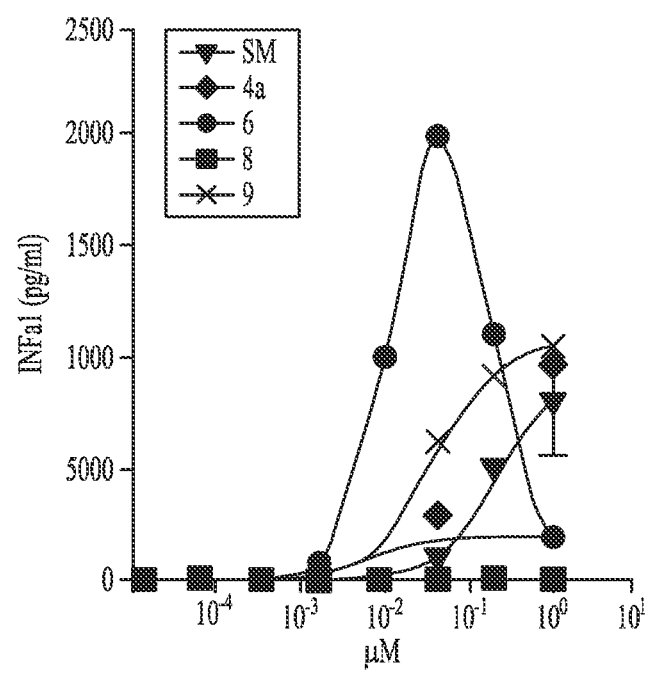

To further investigate the immunological activities in human cells, human PBMC from three donors were treated with TLR7 conjugates and the levels of IL-6 and IFNa1 were determined by LUMINEX assay (FIG. 3A-B). Human serum albumin (HSA) conjugated to TLR7 (4b) was used instead of MSA-conjugates (4a) in this experiment. The order of TLR7 conjugate potency was similar to the order observed in murine macrophages ((4b)>(6)>(9)>/=SM>(8)) (FIG. 3A). A consistent trend in compound potency was observed in PBMC from all donors. Unlike Compound (4a), compound (4b) (e.g., TLR7-HSA conjugate) induced minimum levels of IFNa1 in human PBMC (observed in three donors) (FIG. 3B).

In Vivo Kinetics of Induction of Pro-Inflammatory Cytokines by TLR Conjugates

Figure 4A:
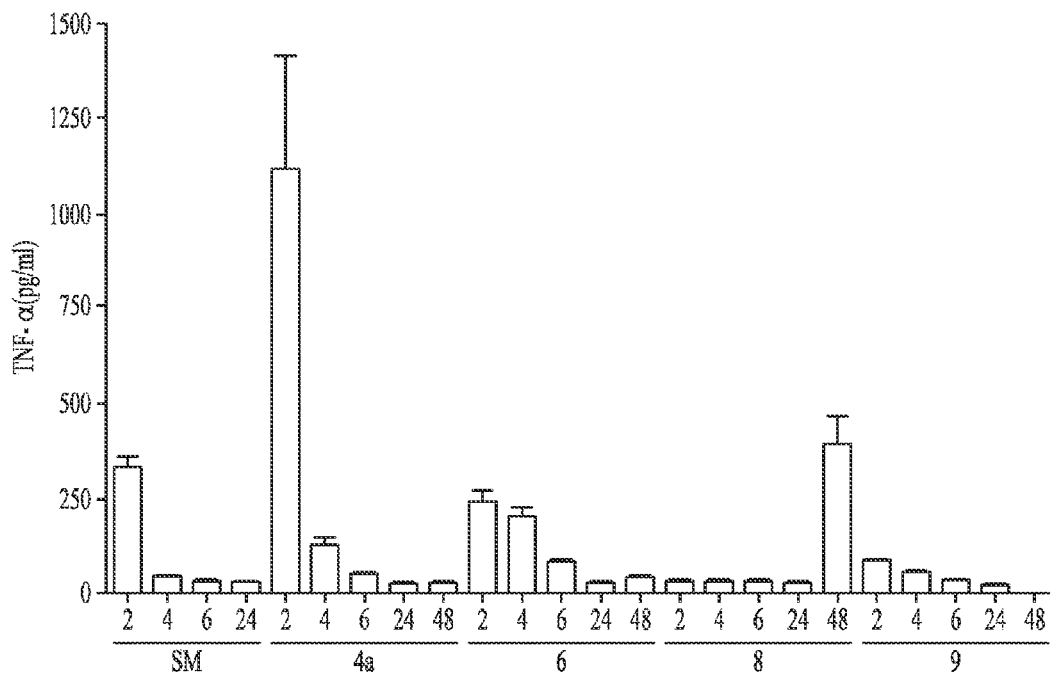
FIGS. 4A-B illustrate the kinetics of pro-inflammatory cytokine induction by TLR7 conjugates in vivo.
Figure 4B:
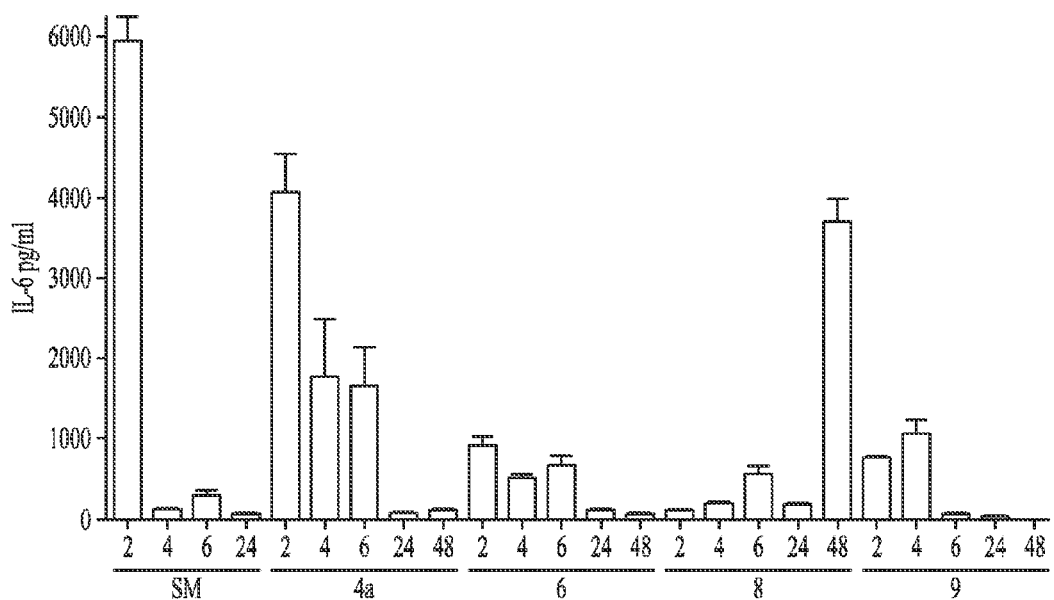

To compare the in vivo immunological properties of TLR7 conjugates, C57BL/5 mice received TLR7 agonist conjugates intravenously and the kinetics of pro-inflammatory cytokines in sera were studied (FIGS. 4A and 4B). Based on a previous study (Wu, C. C et al., Proc Natl Acad Sci USA 104, 3990-5 (2007)), compound (4a) was used at a lower concentration (40 nmol per animal) than compounds SM, (6), (8) and (9) (200 nmol per animal). The maximum induction of TNFα and IL-6 were observed at 2 hours post injection for all TLR7 conjugates (FIGS. 4A-B, respectively). The levels of the cytokines induced by unconjugated TLR7 (SM) declined rapidly after 2 hours. Cytokine induction by compounds (4a), (6), and (9), were sustained for up to 6 hours. Compound (8) induced only a low level of IL-6 (see FIG. 4B), and had no significant induction of TNFα, at any point post injection (see FIG. 4B). Sera from control mice that received saline, MSA, or DOPE revealed little or no detectable cytokine levels (data not shown).

Lipid-TLR7 Conjugates Promote Rapid and Long Lasting Humeral Responses

Figure 5A:
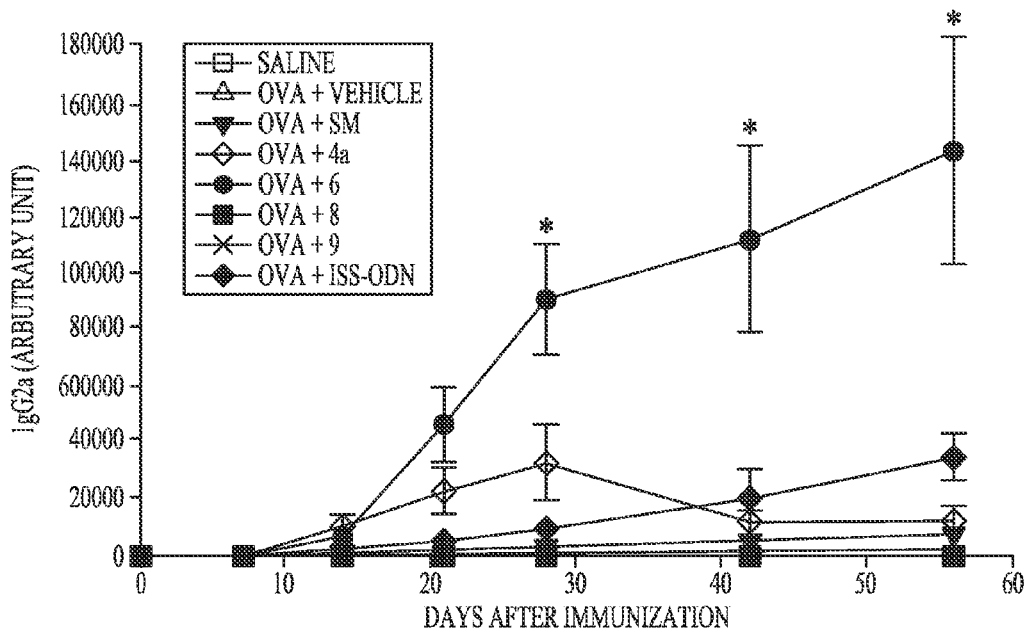
FIGS. 5A-C illustrate the adjuvanticity (e.g., ability to initiate an immunological response) of TLR7 conjugates in vivo.
Figure 5B:
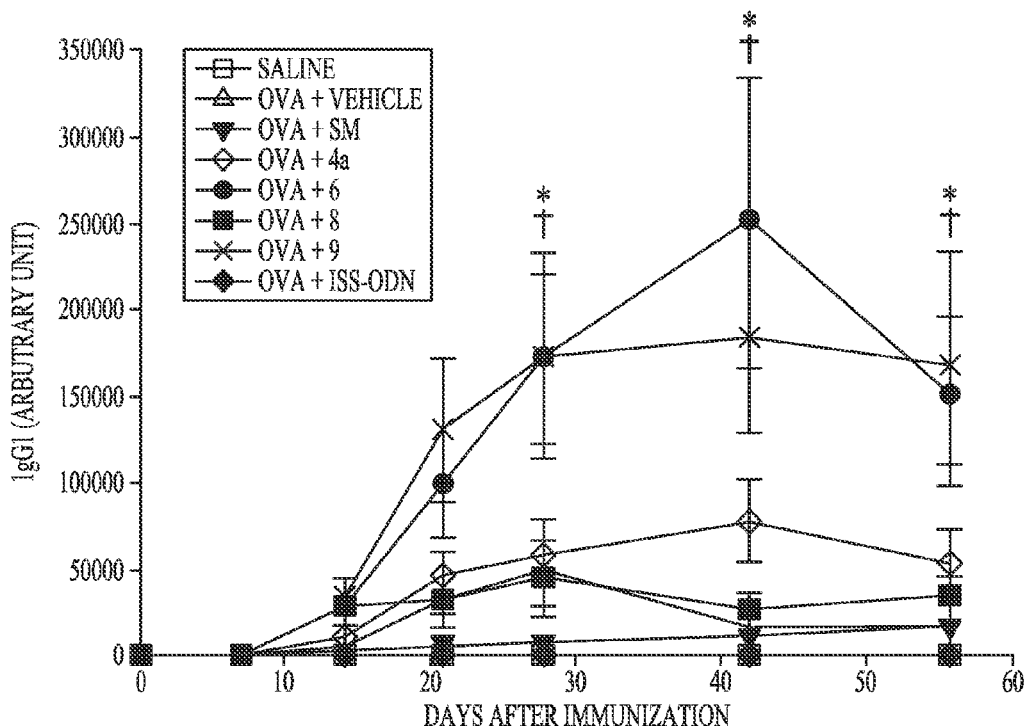

The efficiency of adjuvanticity was assessed by measurement of the levels and isotypes of the antigen-specific IgG that the vaccine induces, in particular IgG1 and IgG2 (Mosmann, T. R., and Coffman, R. L., 'TH1 and TH2 cells: different patterns of lymphokine secretion lead to different functional properties', Annual Review Immunology 7:145-73 (1989)). The groups of C57BL/6 mice (n=5 animals per group) were subcutaneously immunized with OVA (ovalbumin) mixed with TLR7 conjugates. ISS-ODN was used as a potent Th1 adjuvant positive control. Mice immunized with saline or OVA plus vehicle (0.1% DMSO) were used as negative controls. OVA-specific IgG1 and IgG2a serum induction kinetics were monitored by ELISA, on days 0, 7, 14, 21, 28, 42, and 56 (FIGS. 5A-B). Induction of antibodies of the IG subclass was observed as early as 14 days in mice immunized with OVA mixed with compound (4a) or compound (6) (see FIG. 5A). The anti-OVA IgG2a levels continuously increased in mice immunized with OVA/compound (6) mixtures, whereas the levels in mice immunized with OVA/compound (4a) mixture subsequently declined, as illustrated in FIG. 5A. These data are consistent with the enhanced OVA-specific IFNγ secretion by spleen cells of mice immunized with OVA combined with compounds (4a) or (6) (see FIG. 5C).

In Vivo Evaluation of Adverse Effects

TLR7 agonists (SM) can induce anorexic effects and hypothermia in mice (Hayashi, T et al., "Mast cell dependent anorexia and hypothermia induced by mucosal activation of Toll like Receptor 7", Am J Physiol Regul Integr Comp Physiol 295, R123-32 (2008)), causing weight loss in mice. Therefore, as part of the experimental protocol, body weight and skin reaction (at site of injection) of the mice immunized, with lipid-TLR7 agonist conjugates, was monitored. The minimum dose of unconjugated TLR7 agonist (SM) that induced the anorectic reaction in mice was 50 nmoles per mice in mucosal administration (Hayashi, T et al., Am J Physiol Regul Integr Comp Physiol 295, R123-32 (2008)). The dose for the adjuvant experiments (10 nmoles per mouse) was selected to avoid the sickness reaction caused by TLR7 agonists. No significant differences were observed between the average body weights of mice immunized with OVA mixed with compound (6) and the mice injected saline (data not shown).

Chronic administration of TLR7 can also induce myeloid cell proliferation (Baenziger, S et al., "Triggering TLR7 in mice induces immune activation and lymphoid system disruption, resembling HIV-mediated pathology", Blood 113: 377-388 (2009). Total number of spleen cells was calculated as an indicator of the splenic myeloid cell proliferation (see FIG. 6A). There was no significant difference in the total number of spleenocytes between the mice immunized with OVA, TLR7 agonist conjugates and saline control (see FIG. 6B). Histological examination of spleens from mice immunized with OVA mixed with TLR7 agonist showed no structural disruption of the white pulp (germinal center) and no increased cellularity in red pulp (see FIG. 6B). Additionally, no significant difference was observed in the histological examination of the liver, lung, heart and kidney samples collected from each group (data not shown). There also was no macroscopically visible redness or glaucomatous reaction at or near the site of injection with lipid-TLR7 conjugates (see FIG. 6C).

Thioglycolate (TG) can be used as an eliciting agent to recruit leukocytes and macrophages to a site of inflammation. In response to infection or inflammation, neutrophils are typically the first granulocyte cell type to arrive at a site of infection or inflammation. Therefore, treatment with thioglycolate causes a recruitment of many immune response cell types that can be useful for determining potential adverse affects associated with administration of the TLR7 conjugates. The method used for these studies was to pre-treat mice with the various TLR7 conjugate compounds for 3 days, followed by injection of 2 mL of a 3% solution of thioglycolate, 18 hours after the last TLR7 conjugate treatment. 4 hours post TG injection total peritoneal cells were harvested and counted. Neutrophils were identified morphologically and counted. The results are presented in FIGS. 7A-B.

Mice treated with saline only were used as a negative control, and established the basal level of total peritoneal cells and total number of neutrophils, recruited for untreated mice. Mice treated with TG (in saline) but not pre-treated with a TLR7 conjugate were used as a positive control for recruitment and showed approximately $5 \times 10^6$ total cells recruited to the peritoneum, of which approximately 90% were neutrophils (greater than $4 \times 10^6$ neutrophils out of $5 \times 10^6$ total cells). Mice pre-treated with TLR7 free pharmacophore (1V136) or TLR7 conjugate (1V282, compound (8)), showed a reduction in both total cells recruited and neutrophils recruited, indicating that treatment with either free pharmacophore or compound (8) can reduce the level of the inflammation/infection reaction to which leukocytes, granulocytes and macrophages respond, but may have little or no effect on the distribution of cell types recruited (e.g., relative amounts of each cell type). Therefore, free pharmacophore and compound (8) show no additional adverse reaction (e.g., no sickness reaction as described above) when compared to TG and may reduce leukocyte, granulocyte and macrophage recruitment.

MOG protein was also used to evaluate potential adverse effect of various TLR7 conjugates, as described above. Evaluation of the results were by observation of various symptoms associated with MOG induced EAE (e.g., brain inflammation, demyelination of neurons and the like). The severity of symptoms was recorded as a "clinical score", and comparison made between untreated mice (PBS), and mice treated with compound (8) after the initial 6 days of MOG treatment (see FIG. 8). Statistically significant differences in clinical scores are indicated by the * above days 11-17. Treatment with compound (8) significantly reduces the severity of EAE symptoms between days 11 and 17, as well as reducing the initial increase in severity of symptoms as indicated by the difference in slope of the two lines starting at day 8 and going through day 11. Therefore, compound 8 can be said to cause no additional adverse reaction (e.g., no sickness reaction as described above) and may also reduce the severity of symptoms associated with MOG induced EAE.

CONCLUSIONS

Unconjugated TLR7 (SM) is insoluble in aqueous solution. Water-solubility can play a role in controlling drug availability by increasing drug diffusion or promoting uptake to the cells. PEGylation can improve drug solubility and decrease immunogenicity (Veronese, F. M., and Mero, A, "The impact of PEGylation on biological therapies", BioDrugs 22, 315-29 (2008)). PEGylation can also increase drug stability, the retention time of the conjugates in blood and can reduce proteolysis and renal excretion (Veronese, F. M., and Mero, A, BioDrugs 22, 315-29 (2008)). When TLR7 is conjugated to PEG (e.g., compound (8)), the solubility improves dramatically (data not shown). However, potency of cytokine induction is attenuated in comparison to the unmodified TLR7 agonist, in vitro (FIG. 2A, panel A and B) and in vivo (FIGS. 4A and 4B). Activity in both in vitro and in vivo can be restored by further conjugation to DOPE (compound (9)). Compound (9) can induce a Th2 immune response (indicated by IgG1 levels), while exhibiting minimal Th1 response (indicated by IgG2a levels).

Figure 5C:
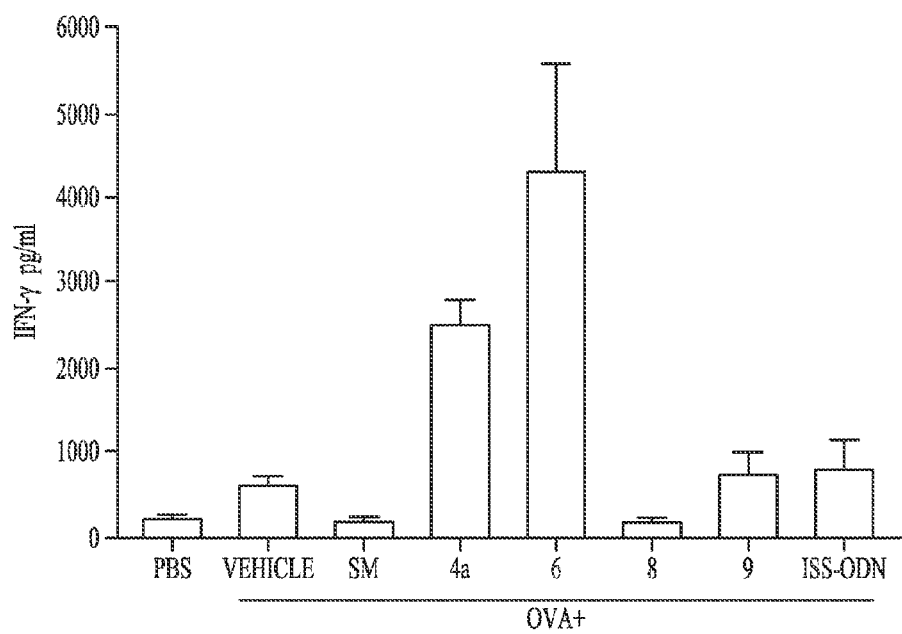

TLR7 agonist conjugates compounds (4a) (MSA conjugate) and (6) (lipid conjugate) promoted rapid elevation of IgG2a titer (FIG. 5A). Levels of IgG2a in mice immunized with MSA-TLR7 conjugates (compound (4a)) declined three weeks after the last immunization, while the mice immunized with OVA mixed with lipidTLR7 conjugates (compound (6)) showed sustained and further accelerated levels of antigen-specific IgG2a (FIG. 5A). Although compound (4a) failed to maintain the levels of IgG2a, the secretion of OVA-specific IFNγ by spleen cells in mice immunized with OVA mixed with compound (4a) maintained relatively high levels (FIG. 5C). The same TLR7 agonists conjugated to different moieties that give distinct immune profiles, can be useful in the design of adjuvants to treat distinct disease categories, such as infection and autoimmune disease, for example.

Various conjugates of a TLR7 agonist were synthesized and found to have distinct immunological profiles both in vivo and in vitro. Diversity in physical properties of reported TLR7 agonist conjugates may allow for a broader range of applications in treatment of different diseases. Water-soluble conjugates can provide a route for systemic administration. Lipid containing conjugates may be suitable for local administration requiring persistent stimulation of the adjacent immune cells (e.g., application of adjuvant for infectious diseases). A lipid moiety can facilitate drug penetration through the skin barrier and may be beneficial for treatment of skin disorders. Conjugation of TLR7 agonist to lipid or PEG moieties may be a promising strategy to expand clinical treatment of infection, cancer or autoimmune disease.

It is concluded from data presented herein that compound (8) has antagonistic activity under certain conditions. FIGS. 4A-B show compound (8) has little or no IL-6 or TNFα stimulating activity, and can reduce certain aspects of inflammation or infection response normally associated with increases in IL-6 or TNFα activity (see FIGS. 7A-B, and FIG. 8). These observations are consistent with antagonistic activity (e.g., a compound can bind but does not stimulate receptor activation). Activation of Toll-like receptors (TLRs) on cells of the innate immune system initiates, amplifies, and directs the antigen-specific acquired immune response. Ligands that stimulate TLRs, therefore, represent potential immune adjuvants. In this study, a potent TLR7 agonist was conjugated with polyethylene glycol (PEG), lipid, or lipid-PEG via a versatile benzoic acid functional group. Compared to the unmodified TLR7 agonist, each conjugate displayed distinctive immunological profile in vitro and in vivo. In mouse macrophages and human peripheral blood mononuclear cells, the lipid-TLR7 conjugates were at least 100 fold more potent than the free TLR7 ligands, while the potencies of PEG and PEG-lipid conjugates were similar to the free form. When the conjugates were administered systemically in vivo, the lipid and lipid-PEG TLR7 conjugates provided sustained levels of immunostimulatory cytokines in serum, compared to the unmodified TLR7 activator. When the conjugates were used as adjuvants during vaccination, only the lipid-TLR7 conjugates induced sustained Th1 as well as Th2 antigen-specific responses. These data show that the immunostimulatory activity of a TLR7 ligand can be amplified and focused by conjugation, thus potentially broadening the potential therapeutic application of these agents.

Additional Compounds and Properties Thereof
Biological Activities

The in vitro activity of a TLR7 agonist conjugated to PEG with various chain lengths was determined by GENEBLAZERCELLSENSOR cell line NFkB-bla RAW 264.7 (Invitrogen) and primary mouse BMDM. Cells were incubated with various concentrations of the TLR7 agonist PEG conjugates. The NFkB activation of GENEBLAZERCELLSENSOR cell line was determined according to the manufacturer's instructions. BMDM were incubated with the conjugates overnight and the level of IL-6 in the supernatant was assessed by ELISA. Estimated EC50 was calculated using Prism.

Figure 9A:
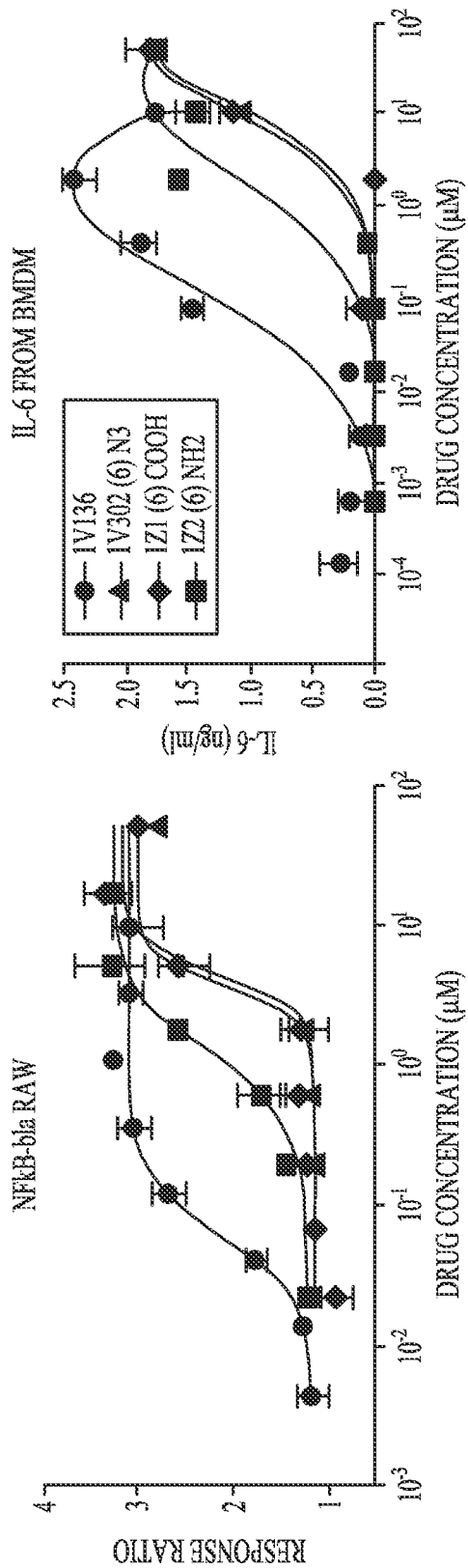
FIGS. 9A-E show the in vitro activity of TLR7 agonist conjugates with varying chain lengths on NFkBbla RAW 264.7 cells and bone marrow derived macrophages (BMDM).
Figure 9B:
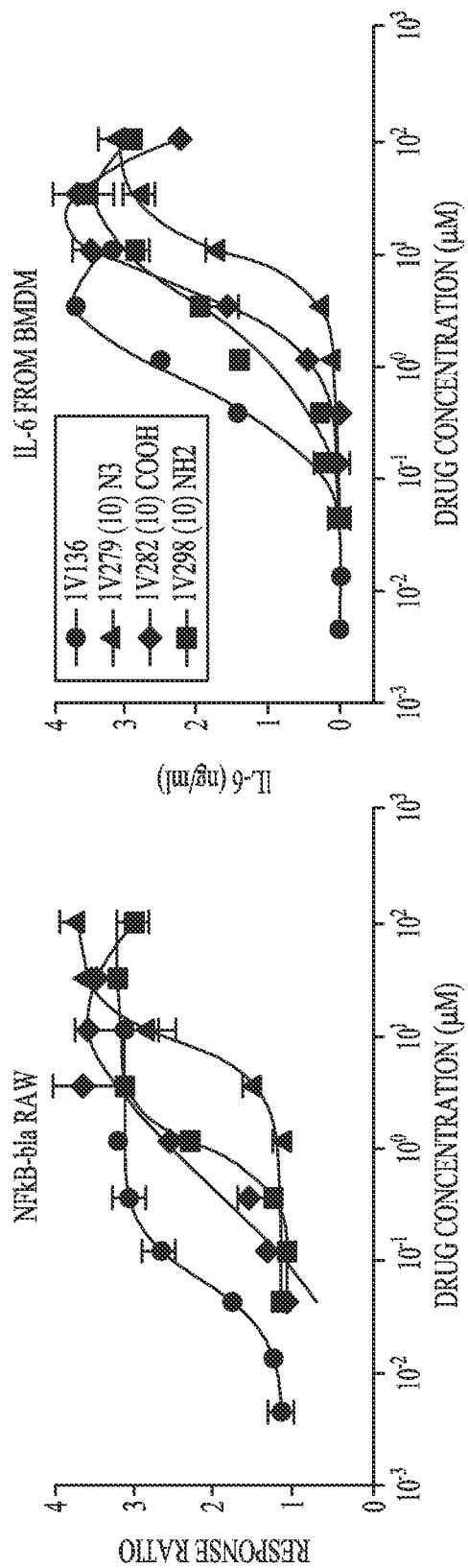
Figure 9C:
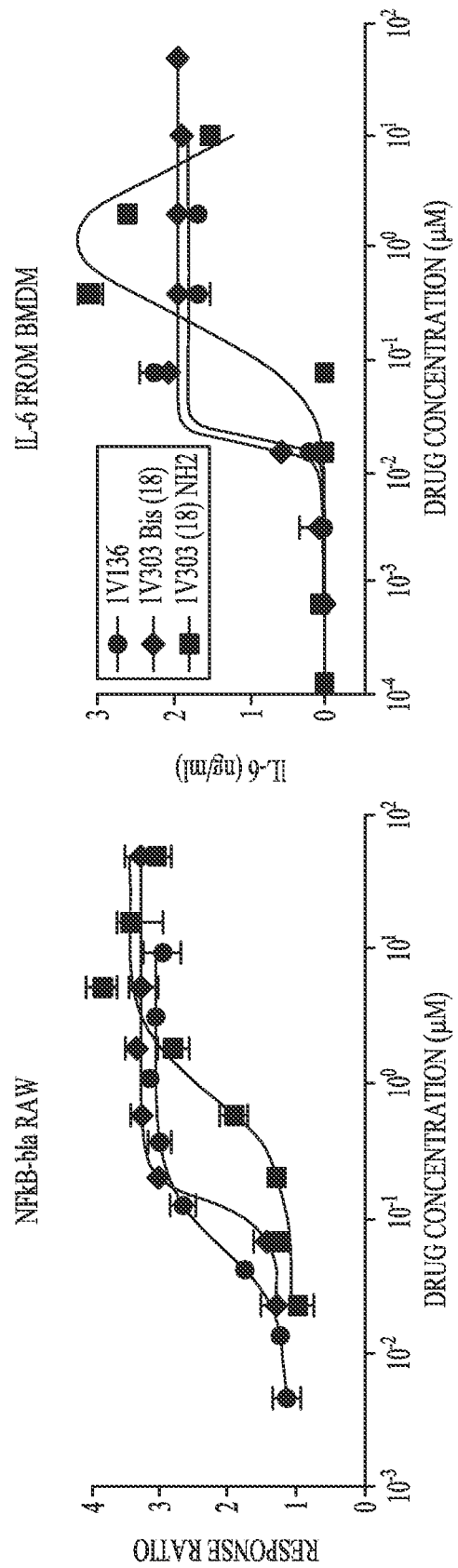
Figure 9D:
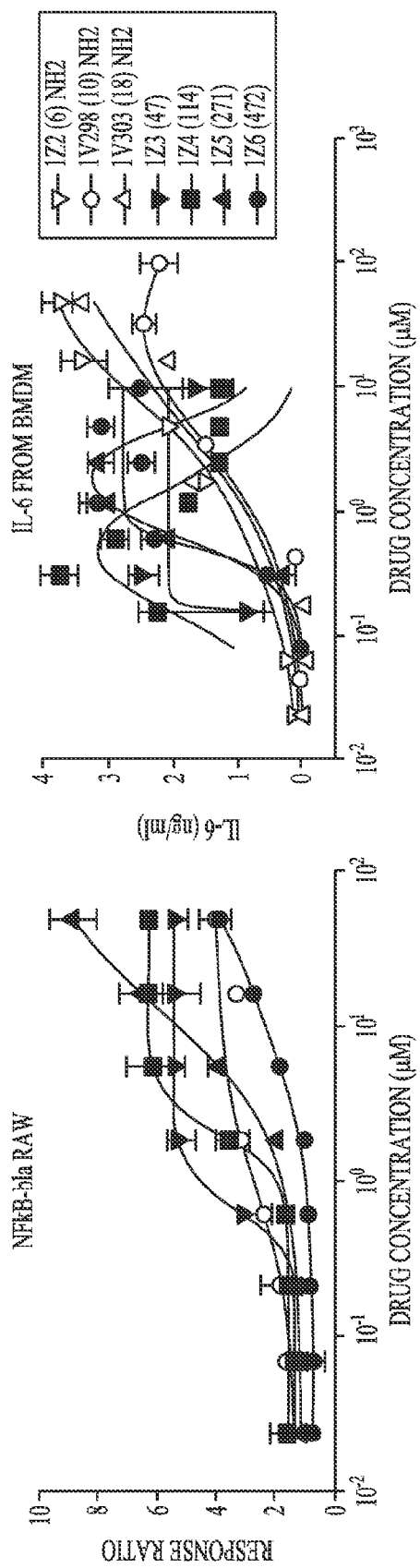
Figure 9E:
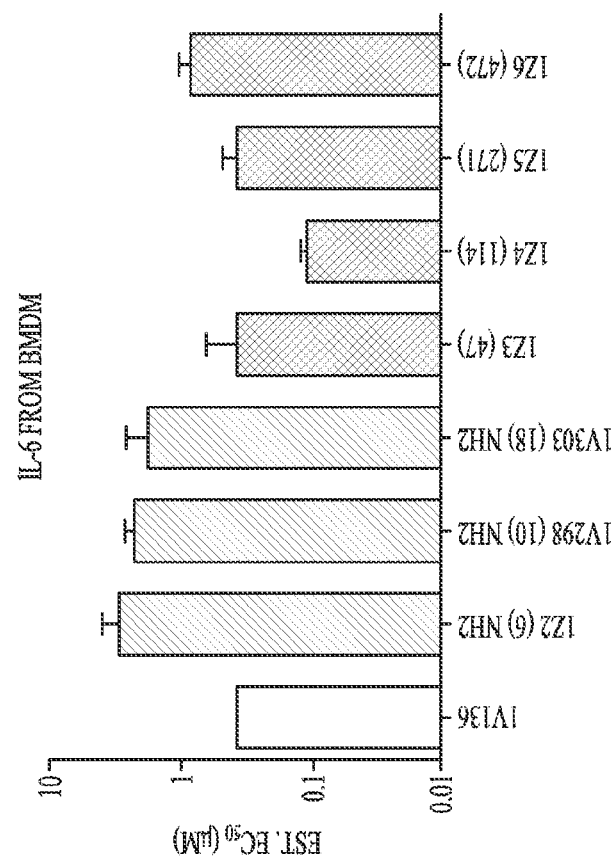
Figure 9E:
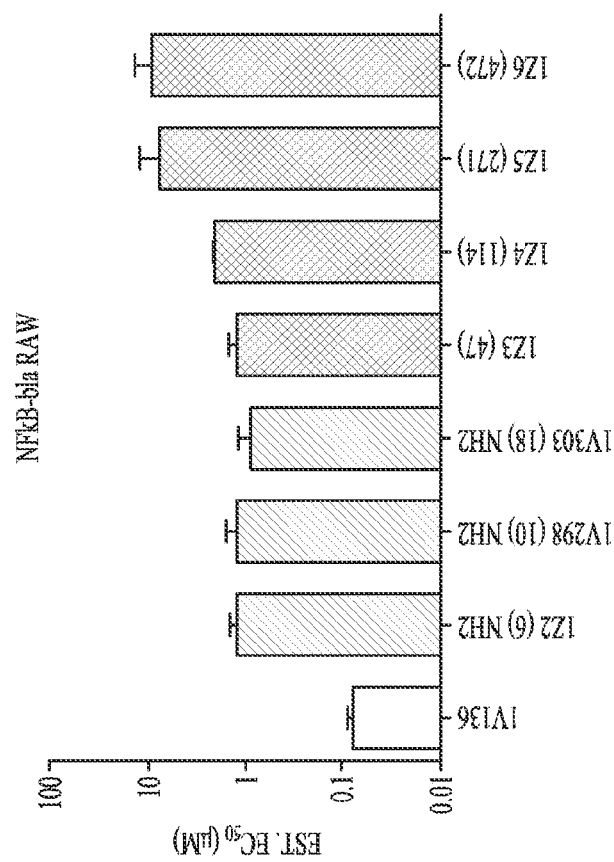

The conjugates with 6, 10, and 18 PEG chains showed similar potency in both NFkB-bla RAW cells and BMDM (FIG. 9A-D). In assays using NFkB-bla RAW cells, the conjugates containing longer PEG chains were less active for activation NFkB (FIG. 9 D-E). In contrast, longer-chain conjugates showed higher activities for IL-6 secretion by BMDM (FIG. 9 D-E). Within the conjugates with 6 PEG chain, the conjugates with $NH_2$ terminal group showed slightly higher activity than the conjugates with COOH or $N_3$ terminal groups (FIG. 9A).

Figure 10A:
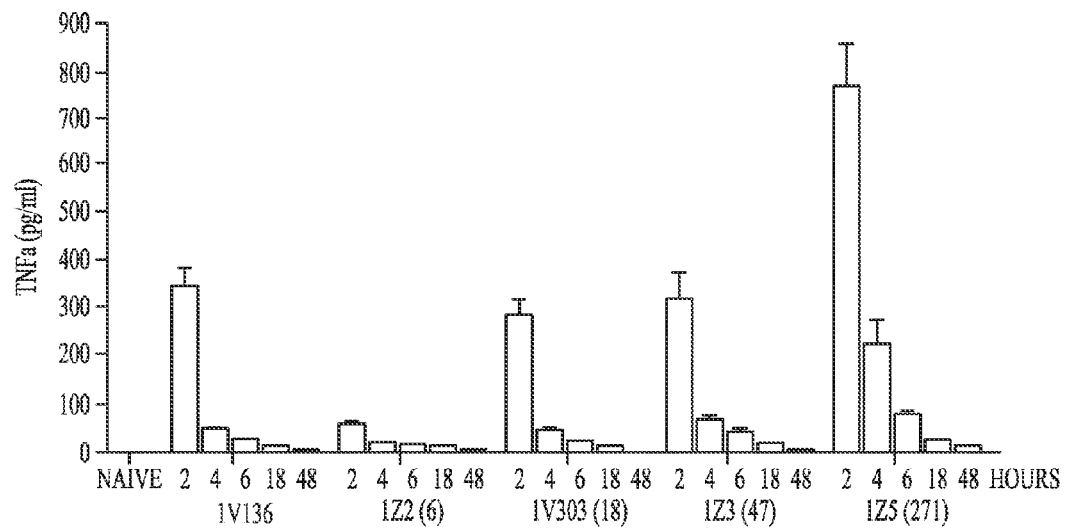
FIGS. 10A-D depict the in vivo pharmacodynamics of TLR7 agonist PEG conjugates administered to mice.
Figure 10B:
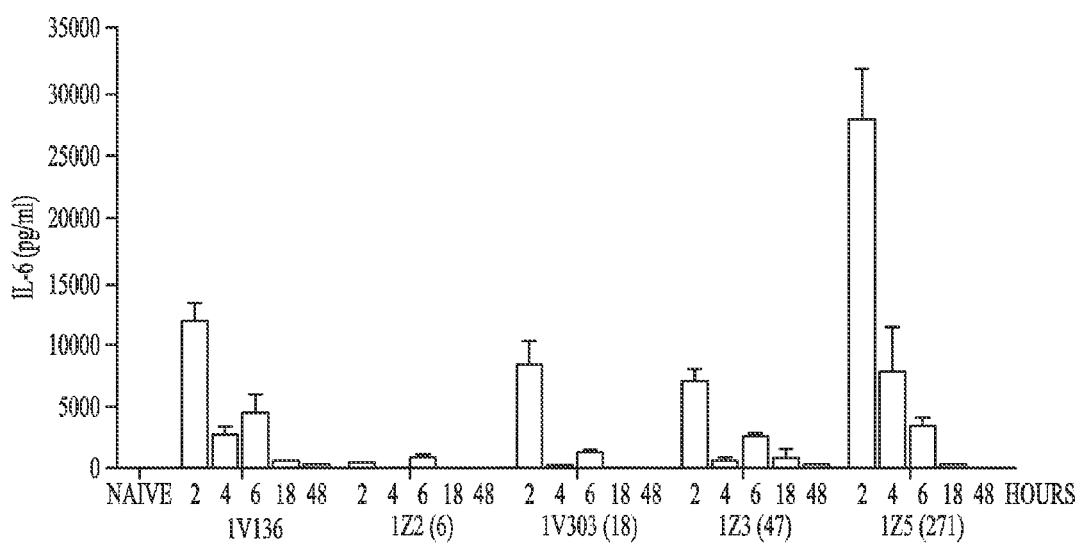

C57BL/6 mice were injected with 200 nmoles of various TLR7 agonist-PEG conjugates in 100 μL saline. Sera were collected at the indicated time points and the levels of cytokines (TNFalpha, IL-6, IL-12) were determined by LUMINEX beads assay (FIG. 10A-B). All compounds used in this study were visibly soluble in 0.1-0.2% DMSO-saline solutions. When free TLR7 agonist was conjugated to 6 PEG chain (1Z2), the activity was diminished (FIG. 10A-B). Conjugates containing longer chains, such as 1V303 (18 PEG chain) and 1Z3 (about s 47 PEG chain), induced cytokines at the level of unconjugated agonist (1V136). 1Z5, which contains approximately a 271-PEG chain, induced higher levels of cytokines than unconjugated TLR7 agonist.

Figure 10C:
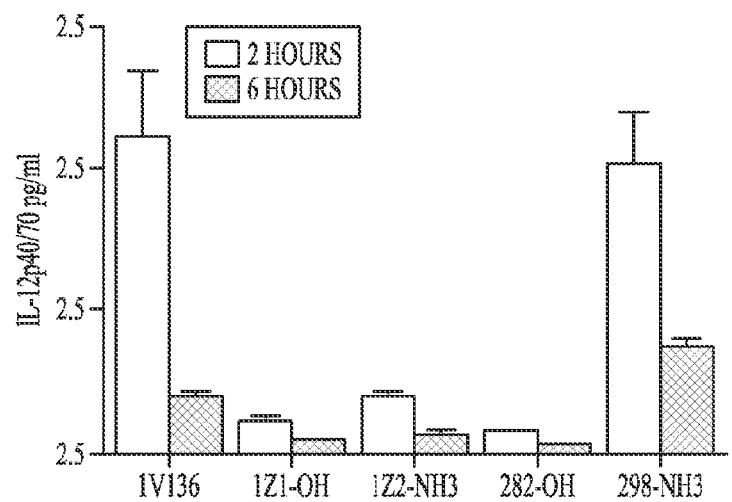
Figure 10D:
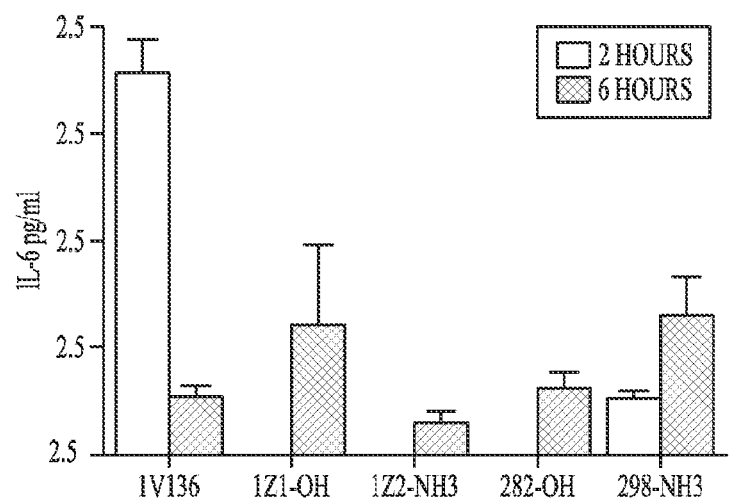

To compare the in vivo bioactivities between $NH_2$ and COOH terminal groups, a 6 PEG chain and a 10 PEG chain conjugated to TLR7 agonists were employed (FIG. 10C). 1Z2 and 1V298 that contain an $NH_2$ terminal group, showed relatively higher cytokine induction than their corresponding conjugates containing a COOH terminal group (FIG. 10C-D).

Figure 11A:
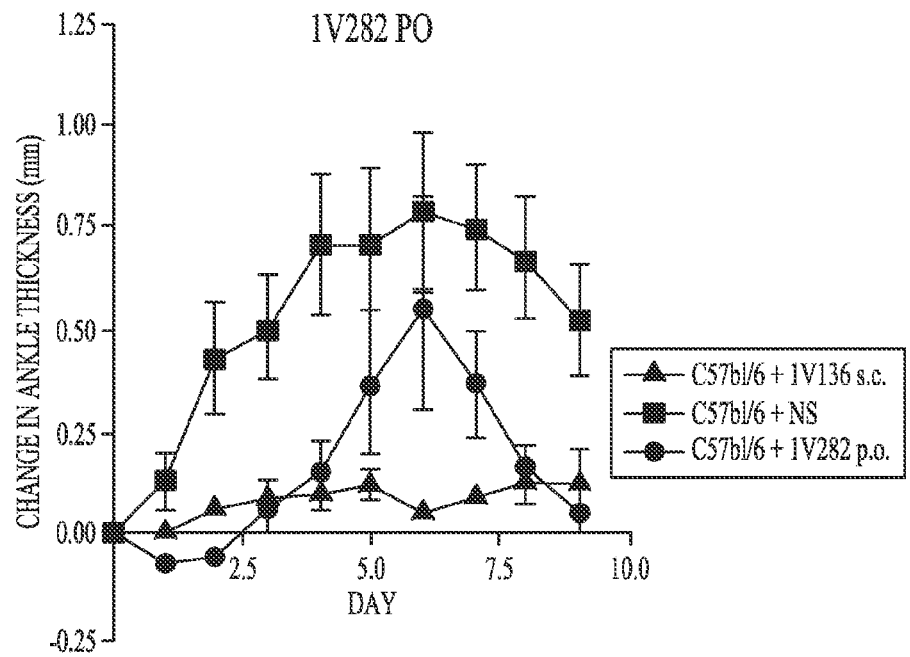
FIGS. 11A-B illustrate the anti-inflammatory effects of 1V282 administered by daily gavage (A) or by subcutaneous injection (B) in a serum transferred arthritis model.
Figure 11B:
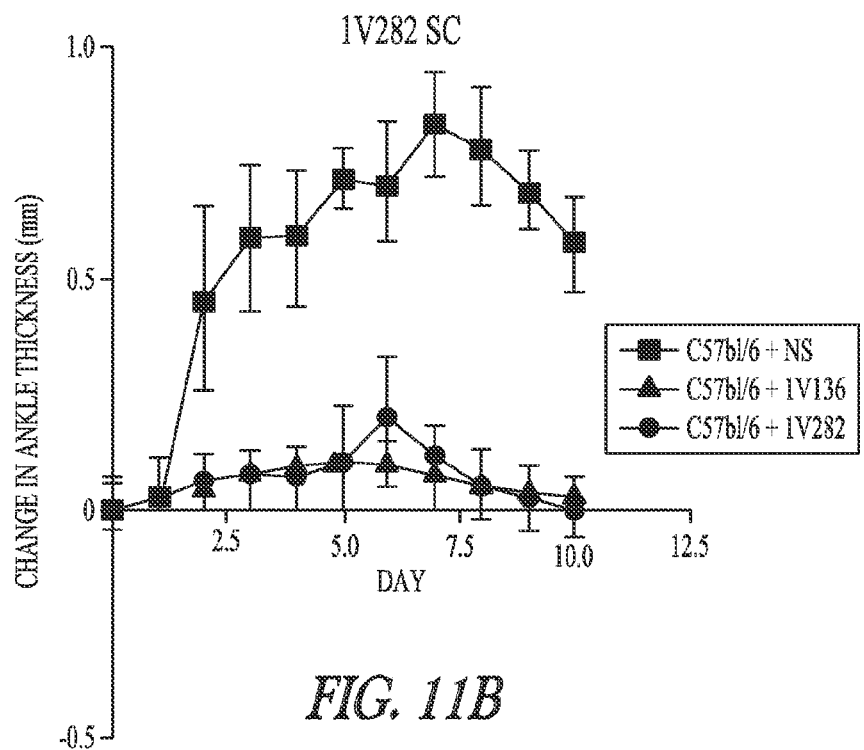

The anti-inflammatory efficacy of TLR7 agonist-PEG conjugates was tested in mouse models of human inflammatory diseases (serum transfer arthritis, experimental allergic encephalomyelitis (EAE) (see above), and thioglycollate induced peritonitis). For serum transferred arthritis (FIG. 11), C57BL/6 mice were injected with K/BxN serum on day 0 and treated by daily gavage (FIG. 11A) or subcutaneous (FIG. 11B) injection of 1V282. Daily administration of 1V282 reduced paw swelling in both subcutaneous and gavage treatment.

Figure 12B:
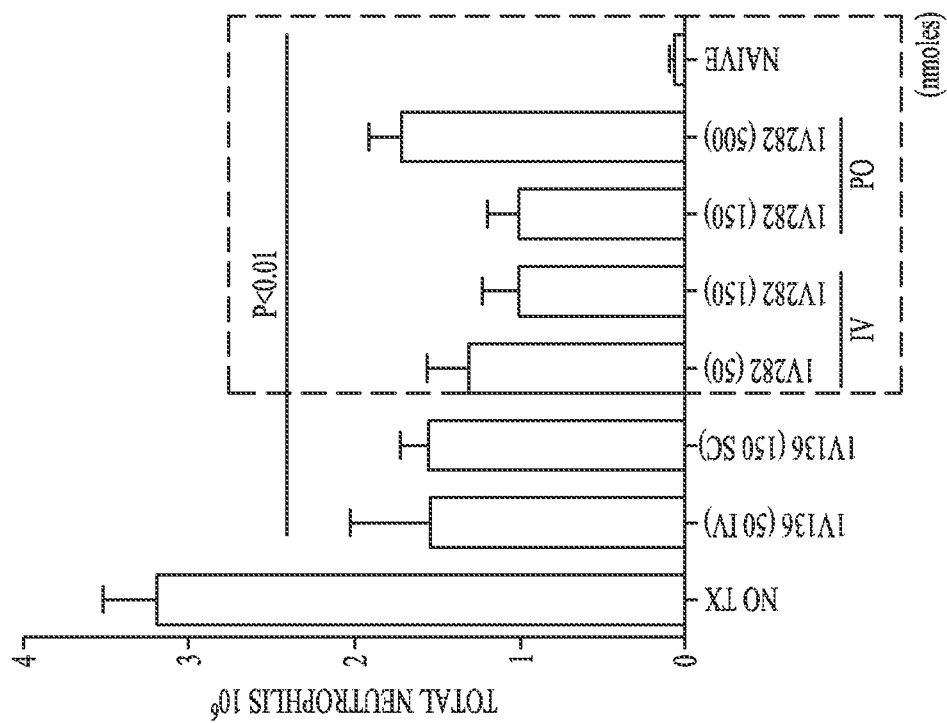
FIGS. 12A-B show the anti-inflammatory effects of TLR7 agonist PEG conjugates in a thioglycolate induced peritonitis model.
Figure 12A:
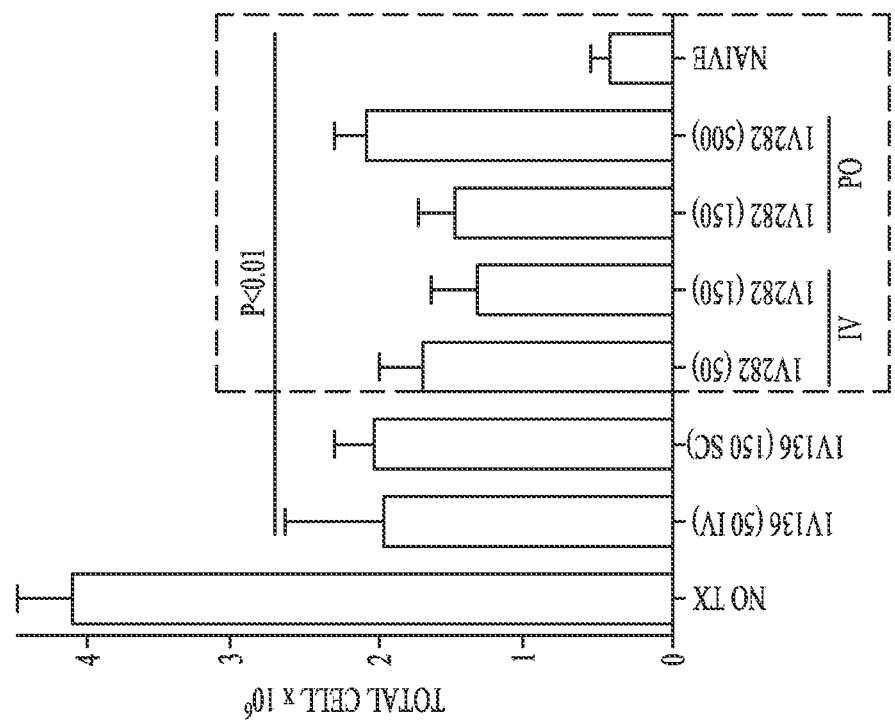

For thioglycollate peritonitis (FIG. 12), C57BL/6 mice were intravenously or orally administered with 1V282 for three days. One day after the last treatment, mice received intraperitoneal injection of 2 ml thioglycollate medium. Intravenous and subcutaneous administrations of 1V136 were used as positive controls. Three hours after the thioglycollate injection, neutrophil infiltration to the peritoneum was evaluated. Administration of 1V282 by both systemic and oral route reduced cell infiltration, particularly neutrophil, to the peritoneal cavity.

Type1 diabetes in humans is characterized by a specific destruction of the pancreatic β cells, commonly associated with immune-mediated damage. Chemically induced diabetes models are employed to test if chronic administration of TLR7 agonist-PEG conjugates can reduce the severity or onset of the diseases. Multiple small doses of streptozotocin (alkylating agent) are used (e.g. 40 mg/kg on five consecutive days). In susceptible rodents this induces an insulinopenic diabetes in which immune destruction plays a role, as in human Type 1 diabetes. Based on the mode of action observed in other related diseases TLR7-PEG conjugates will ameliorate the course of this disease.

TABLE 2

| Compound # | Structure | MW | Chain Length | Chain MW | m/Z |
|---|---|---|---|---|---|
| 1V302 | 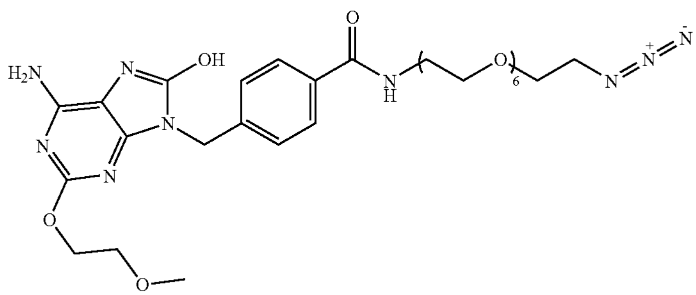 | 691.33 | 6 | 350.42 | 692.6 |
| 1Z1 | 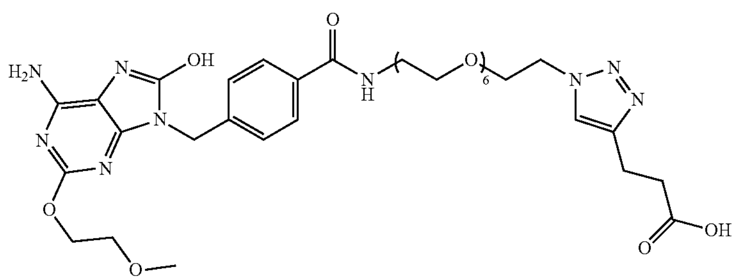 | 789.83 | 6 | 350.42 | 790.6 |
| 1Z2 | 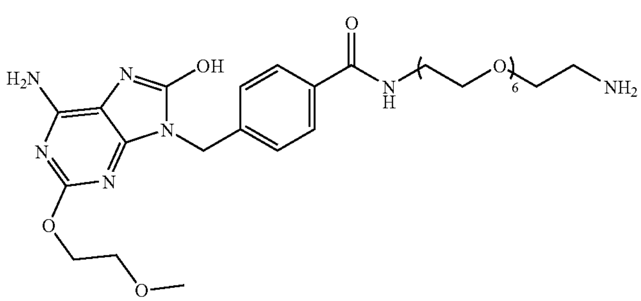 | 665.74 | 6 | 350.42 | 666.6 |
| 1V279 | 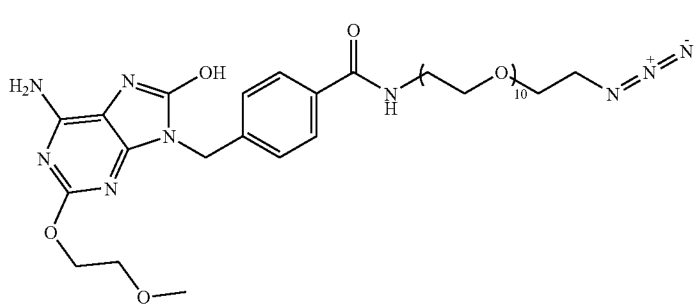 | 867.43 | 10 | 526.62 | 868.5 |

TABLE 2-continued

| Compound # | Structure | MW | Chain Length | Chain MW | m/Z |
|---|---|---|---|---|---|
| 1V298 | 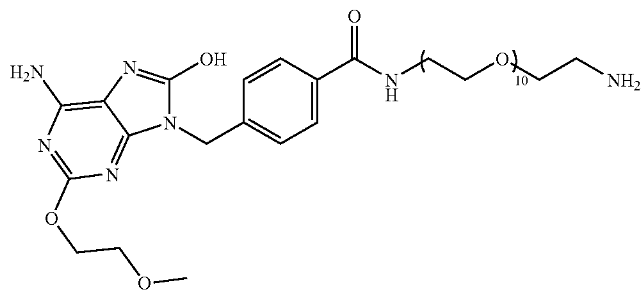 | 841.95 | 10 | 526.62 | 842.6 |
| 1V282 | 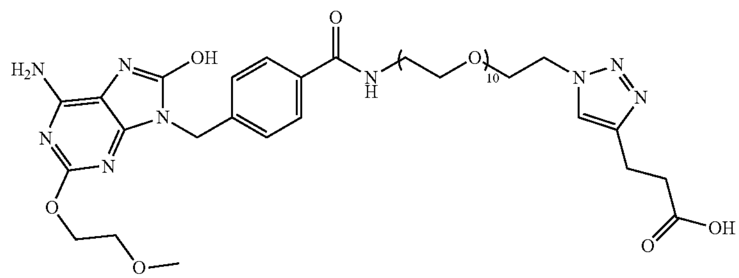 | 966.04 | 10 | 526.62 | 966.8 |
| 1V303 | 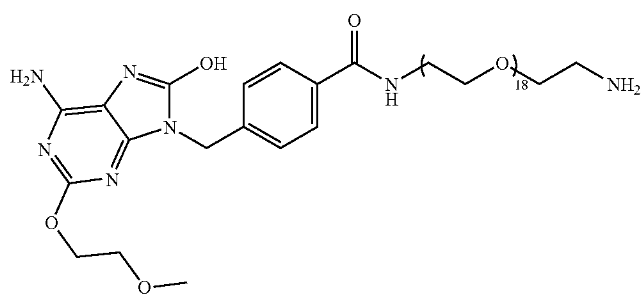 | 1238.42 | 18 | 897.1 | 1238.7 |
| 1V303bis | | 1579.74 | 18 | 897.1 | 1579.1 |
| 1Z3 | 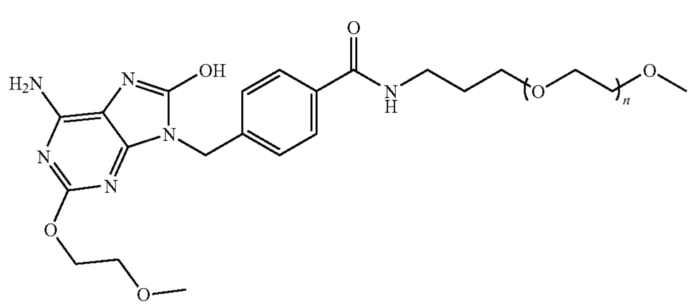 | 2525.13$_a$ | 47$_a$ | 2182 | $_b$ |

TABLE 2-continued

| Compound # | Structure | MW | Chain Length | Chain MW | m/Z |
|---|---|---|---|---|---|
| 1Z4 | 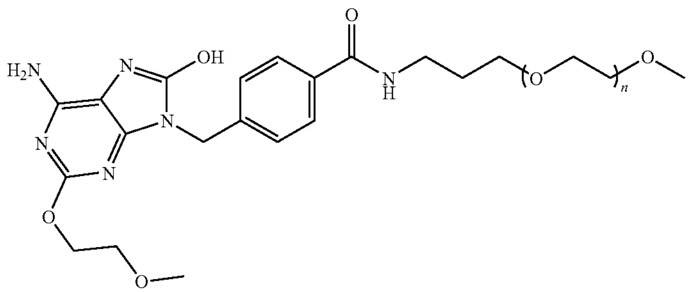 | 5572.13$_a$ | 114$_a$ | 5229 | $_b$ |
| 1Z5 | 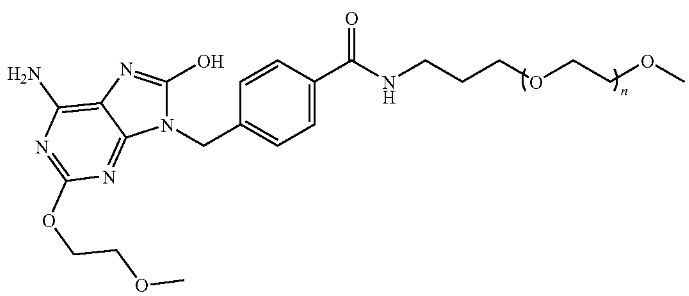 | 12609.13$_a$ | 271$_a$ | 12266 | $_b$ |
| 1Z6 | 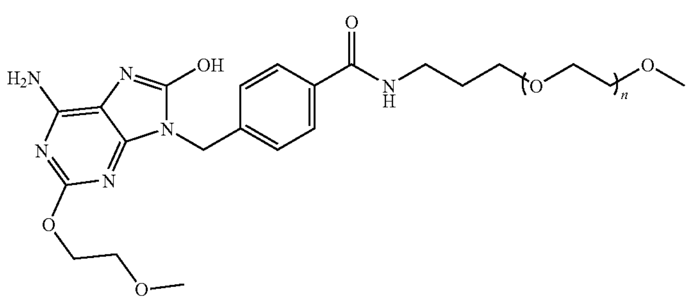 | 21701.13$_a$ | 472$_a$ | 21358 | $_b$ |
| 1Z7 | 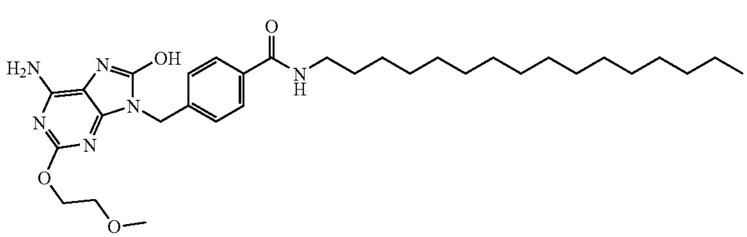 [SMILES: CCCCCCCCCCCCCCCCNC(=O)c1ccc(Cn2c(O)nc3c(N)nc(OCCOC)nc32)cc1] | 582.78 | 16 | 241.46 | 583.7 |
| 1Z9 | 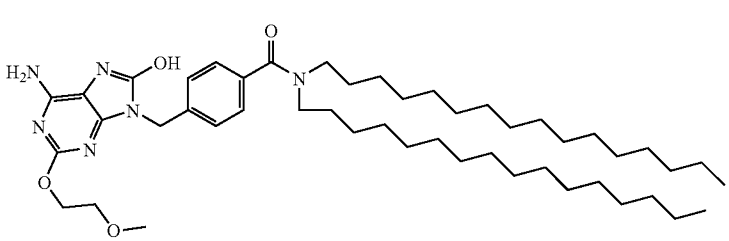 [SMILES: CCCCCCCCCCCCCCCCN(CCCCCCCCCCCCCCCC)C(=O)c1ccc(Cn2c(O)nc3c(N)nc(OCCOC)nc32)cc1] | 807.2 | 2 × 16 | 465.88 | |

TABLE 2-continued

| Compound # | Structure | MW | Chain Length | Chain MW | m/Z |
|---|---|---|---|---|---|
| 1Z18 | 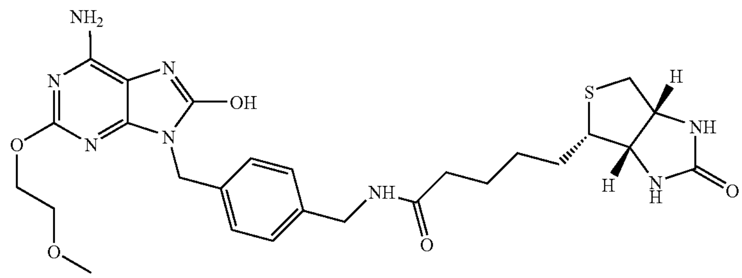 [SMILES: COCCOc1nc(N)c2nc(O)n(Cc3ccc(CNC(=O)CCCC[C@@H]4SC[C@@H]5NC(=O)N[C@@H]54)cc3)c2n1] | 570.66 | — | — | |

<sub>a</sub>Approximate molecular weight due to heterogeneity of PEG polymer.
<sub>b</sub>Characterized by NMR only.

CITATIONS

1) Takeda, K., and Akira, S. (2005) Toll-like receptors in innate immunity. Int Immunol 17, 1-14.
2) Akira, S., and Takeda, K. (2004) Toll-like receptor signalling. Nat Rev Immunol 4, 499-511.
3) Hemmi, H., Kaisho, T., Takeuchi, O., Sato, S., Sanjo, H., Hoshino, K., Horiuchi, T., Tomizawa, H., Takeda, K., and Akira, S. (2002) Small anti☐viral compounds activate immune cells via the TLR7MyD88-dependent signaling pathway. Nat Immunol 3, 196-200.
4) Akira, S. (2006) TLR signaling. Curr Top Microbiol Immunol 311, 1-16.
5) Diebold, S. S., Kaisho, T., Hemmi, H., Akira, S., and Reis e Sousa, C. (2004) Innate antiviral responses by means of TLR7-mediated recognition of single-stranded RNA. Science 303, 1529-31.
6) Lee, J., Chuang, T. H., Redecke, V., She, L., Pitha, P. M., Carson, D. A., Raz, E., and Cottam, H. B. (2003) Molecular basis for the immunostimulatory activity of guanine nucleoside analogs: activation of Toll-like receptor 7. Proc Natl Acad Sci USA 100, 6646-51.
7) Lee, J., Mo, J. H., Katakura, K., Alkalay, I., Rucker, A. N., Liu, Y. T., Lee, H. K., Shen, C., Cojocaru, G., Shenouda, S., Kagnoff, M., Eckmann, L., BenNeriah, Y., and Raz, E. (2006) Maintenance of colonic homeostasis by distinctive apical TLR9 signalling in intestinal epithelial cells. Nat Cell Bio 8, 1327-36.
8) Kurimoto, A., Ogino, T., Ichii, S., Isobe, Y., Tobe, M., Ogita, H., Takaku, H., Sajiki, H., Hirota, K., and Kawakami, H. (2004) Synthesis and evaluation of 2-substituted 8-hydroxyadenines as potent interferon inducers with improved oral bioavailabilities. Bioorg Med Chem 12, 1091-9.
9) Wu, C. C., Hayashi, T., Takabayashi, K., Sabet, M., Smee, D. F., Guiney, D. D., Cottam, H. B., and Carson, D. A. (2007) Immunotherapeutic activity of a conjugate of a Toll-like receptor 7 ligand. Proc Natl Acad Sci USA 104, 3990-5.
10) Guiducci, C., Ott, G., Chan, J. H., Damon, E., Calacsan, C., Matray, T., Lee, K. D., Coffman, R. L., and Barrat, F. J. (2006) Properties regulating the nature of the plasmacytoid dendritic cell response to Toll-like receptor 9 activation. J Exp Med 203, 1999-2008.
11) Honda, K., Ohba, Y., Yanai, H., Negishi, H., Mizutani, T., Takaoka, A., Taya, C., and Taniguchi, T. (2005) Spatiotemporal regulation of MyD88-IRF-7 signalling for robust type-I interferon induction. Nature 434, 1035-40.
12) Kagan, J. C., Su, T., Horng, T., Chow, A., Akira, S., and Medzhitov, R. (2008) TRAM couples endocytosis of Toll-like receptor 4 to the induction of interferon-beta. Nat Immunol 9, 361-8.
13) Veronese, F. M., and Mero, A. (2008) The impact of PEGylation on biological therapies. BioDrugs 22, 315-29.
14) Cho, H. J., Takabayashi, K., Cheng, P. M., Nguyen, M. D., Corr, M., Tuck, S., and Raz, E. (2000) Immunostimulatory DNA-based vaccines induce cytotoxic lymphocyte activity by a T-helper cell-independent mechanism [see comments]. Nat Biotechnol 18, 509-14.
15) Hayashi, T., Rao, S. P., Takabayashi, K., Van Uden, J. H., Kornbluth, R. S., Baird, S. M., Taylor, M. W., Carson, D. A., Catanzaro, A., and Raz, E. (2001) Enhancement of innate immunity against Mycobacterium avium infection by immunostimulatory DNA is mediated by indoleamine 2,3-dioxygenase. Infect Immun 69, 6156-64.
16) Roman, M., Martin-Orozco, E., Goodman, J. S., Nguyen, M. D., Sato, Y., Ronaghy, A., Kornbluth, R. S., Richman, D. D., Carson, D. A., and Raz, E. (1997) Immunostimulatory DNA sequences function as T helper-1-promoting adjuvants [see comments]. Nat Med 3, 849-54.
17) Kobayashi, H., Horner, A. A., Martin-Orozco, E., and Raz, E. (2000) Pre-priming: a novel approach to DNA-based vaccination and immunomodulation. Springer Semin Immunopathol 22, 85-96.
18) Mosmann, T. R., and Coffman, R. L. (1989) TH1 and TH2 cells: different patterns of lymphokine secretion lead to different functional properties. Annual Review Immunology 7, 145-73.
19) Hayashi, T., Cottam, H. B., Chan, M., Jin, G., Tawatao, R. I., Crain, B., Ronacher, L., Messer, K., Carson, D. A., and Corr, M. (2008) Mast cell-dependent anorexia and hypothermia induced by mucosal activation of Toll-like receptor 7. Am J Physiol Regul Integr Comp Physiol 295, R123-32.
20) Baenziger, S., Heikenwalder, M., Johansen, P., Schlaepfer, E., Hofer, U., Miller, R. C., Diemand, S., Honda, K., Kundig, T. M., Aguzzi, A., and Speck, R. F. (2008) Triggering TLR7 in mice induces immune activation and lymphoid system disruption, resembling HIV-mediated pathology. Blood.
21) Rothenfusser, S., Tuma, E., Endres, S., and Hartmann, G. (2002) Plasmacytoid dendritic cells: the key to CpG. Hum Immunol 63, 1111-9.
22) Kenney, J. S., Hughes, B. W., Masada, M. P., and Allison, A. C. (1989) Influence of adjuvants on the quantity, affinity, isotype and epitope specificity of murine antibodies. J Immunol Methods 121, 157-66.

23) Mosmann, T. R., and Coffman, R. L. (1989) TH1 and TH2 cells: different patterns of lymphokine secretion lead to different functional properties. Annu Rev Immunol 7, 145-73.

24) Purdon, C. H., Azzi, C. G., Zhang, J., Smith, E. W., and Maibach, H. I. (2004) Penetration enhancement of transdermal delivery—current permutations and limitations. Crit. Rev Ther Drug Carrier Syst 21, 97-132.

25) Chang, Y. C., Madkan, V., Cook-Norris, R., Sra, K., and Tyring, S. (2005) Current and potential uses of imiquimod. South Med J 98, 914-20.

26) Cha, J. S., Jang, S. H., and Kwon, S. Y. (2002) Selective conversion of aromatic nitriles to aldehydes by lithium N,N'-dimethylethylenediaminoaluminum hydride. Bull. Korean Chem. Soc. 23, 1697-1698.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

What is claimed is:

1. A compound having a structure according to Formula I:

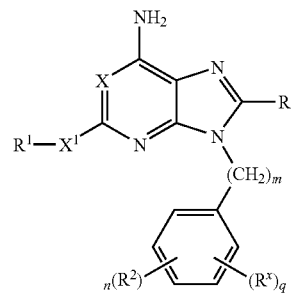

(Formula I)

or a pharmaceutically acceptable salt thereof, wherein:

X is N;

R is —OR$^1$, —SR$^1$, or —NR$^a$R$^b$,

X$^1$ is —O—, —S—, or —NR$^c$—;

R$^c$ is hydrogen, C1-C10 alkyl, or substituted C1-C10 alkyl, or R$^c$ and R$^1$ taken together with the nitrogen atom can form a heterocyclic ring or a substituted heterocyclic ring;

each R$^1$ independently is hydrogen, C1-C10 alkyl, substituted C1-C10 alkyl, C1-C10 alkoxy, substituted C1-C10 alkoxy, C1-C10 alkyl C1-C10 alkoxy, C6-C10 aryl, C5-C10 heteroaryl, substituted C5-C10 aryl, C5-C9 heterocyclic, substituted C5-C9 heterocyclic, C3-C9 carbocyclic or substituted C3-C9 carbocyclic;

each R$^2$ independently is hydrogen, —OH, C1-C6 alkyl, substituted C1-C6 alkyl, C1-C6 alkoxy, substituted C1-C6 alkoxy, —C(O)—C1-C6 alkyl (alkanoyl), substituted —C(O)—C1-C6 alkyl, —C(O)—C6-C10 aryl (aroyl), substituted —C(O)—C6-C10 aryl, —C(O)OH (carboxyl), —C(O)O—C1-C6 alkyl (alkoxycarbonyl), substituted —C(O)O—C1-C6 alkyl, —NR$^a$R$^b$, —C(O)NR$^a$R$^b$ (carbamoyl), substituted C(O)NR$^a$R$^b$, halo, nitro, or cyano;

the substituents on the alkyl, alkoxy, aryl or heterocyclic groups are hydroxy, C1-C6 alkyl, hydroxy C1-C6 alkylene, carboxy C1-C6 alkylene, C1-C6 alkoxy, C3-C6 cycloalkyl, C1-C6 alkoxy C1-C6 alkylene, amino, cyano, halogen, or aryl;

each R$^a$ and R$^b$ is independently hydrogen, C1-C20 alkyl, C3-C8 cycloalkyl, C1-C6 alkoxy, halo C1-C6 alkyl, C3-C8 cycloalkyl C1-C6 alkyl, C1-C6 alkanoyl, hydroxy C1-C6 alkyl, aryl, aryl C1-C6 alkyl, hetero C1-C10 alkyl, wherein C1-C10 alkyl is substituted with one or more O, S or N atoms, heterocyclyl, wherein the heterocyclyl is substituted with one or more O, S or N atoms, or C1-C6 alkoxycarbonyl;

each R$^x$ is independently —X$^2$—((R$^3$)$_r$—(R$^4$)$_s$);

each X$^2$ independently is —C(O)NH—, —NH(O)C—, —C1-C6 alkyl-C(O)NH—, —C1-C6 alkyl-NH(O)C—, —C(O)NH—C1-C6 alkyl-, —NH(O)C—C1-C6 alkyl-, —C1-C6 alkyl—NH(O)C—C1-C6 alkyl-, —C1-C6 alkyl-C(O)NH—C1-C6 alkyl-, or —C(O)NH—(CH$_2$)$_t$—;

each R$^3$ independently is a polyethylene glycol (PEG) moiety;

each R$^4$ independently is H, —C1-C6 alkyl, —C1-C6 alkoxy, —NR$^a$R$^b$, —N$_3$, —OH, —CN, —COOH, —COOR', —C1-C6 alkyl-NR$^a$R$^b$, C1-C6 alkyl-OH, C1-C6 alkyl-CN, C1-C6 alkyl-COOH, C1-C6 alkyl-COOR', 5-6 membered ring, substituted 5-6 membered ring, —C1-C6 alkyl-5-6 membered ring, —C1-C6 alkyl-substituted 5-6 membered ring C2-C9 heterocyclic, or substituted C2-C9 heterocyclic;

m is 1, 2, 3, 4, 5, 6, 7, 8, 9 or 10;
n is 0, 1, 2, 3 or 4;
p is 1 to 100;
q is 1, 2,3, 4 or 5;
r is 2 to 1,000;
s is 1 to 1,000; and
the sum of n and q equals 5.

2. The compound of claim 1, wherein $X^1$ is oxygen.

3. The compound of claim 1 or 2, wherein $R^1$ is a substituted C1-C6 alkyl.

4. The compound of claim 1, wherein $R^1$ is a C1-C10 alkyl or C1-C10 alkoxy moiety.

5. The compound of claim 4, wherein $R^1$ is —$CH_2CH_2OCH_3$.

6. The compound of claim 1, wherein n is 4 and $R^2$ is hydrogen in each instance.

7. The compound of claim 1, wherein each PEG unit is —O—$CH_2$—$CH_2$— or —$CH_2$—$CH_2$—O—.

8. The compound of claim 1, wherein r is 5 to 100.

9. The compound of claim 1, wherein s is 5 to 100.

10. The compound of claim 1, wherein one or more of the PEG moieties are linear.

11. The compound of claim 1, wherein one or more of the PEG moieties are branched.

12. The compound of claim 1, wherein each $R^4$ substituent is independently is H, C1-C2 alkyl, —C1-C2 alkoxy —$NR^aR^b$, —OH, —CN, —COOH, —$COOR^1$, —C1-C2 alkyl-$NR^aR^b$, C1-C2 alkyl-OH, C1-C2 alkyl-CN, C1-C2 alkyl-COOH or C1-C2 alkyl-$COOR^1$.

13. The compound of claim 1, wherein m is 1.

14. The compound of claim 13, wherein $R^2$ is hydrogen, n is 4, q is 1, p is 1, r is 10 and s is 1.

15. A pharmaceutical composition comprising a pharmaceutically acceptable salt of a compound of claim 1 and a pharmaceutically acceptable carrier.

16. The pharmaceutical composition of claim 15, wherein the pharmaceutically acceptable salt is prepared using an acid selected from the group consisting of hydrochloric, hydrobromic, sulfuric, sulfamic, phosphoric and nitric acid.

17. The pharmaceutical composition of claim 15, wherein the pharmaceutically acceptable salt is prepared using an acid selected from the group consisting of acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid.

18. The pharmaceutical composition of claim 15, wherein the pharmaceutically acceptable salt is prepared using a base selected from the group consisting of potassium hydroxide, sodium hydroxide, ammonium hydroxide, caffeine, and an amine.

* * * * *

UNITED STATES PATENT AND TRADEMARK OFFICE
CERTIFICATE OF CORRECTION

PATENT NO.       : 8,729,088 B2
APPLICATION NO.  : 12/704343
DATED            : May 20, 2014
INVENTOR(S)      : Carson et al.

Page 1 of 5

It is certified that error appears in the above-identified patent and that said Letters Patent is hereby corrected as shown below:

On the Title page, in column 2, under "Other Publications", line 8, delete "mailed" and insert --filed--, therefor On Title page 2, in column 2, under "Other Publications", line 20, delete "mailed" and insert --filed--, therefor On Title page 2, in column 2, under "Other Publications", line 29, delete "flied" and insert --filed--, therefor On Title page 3, in column 2, under "Other Publications", line 66, delete "immunomoduiation"," and insert --immunomodulation",--, therefor On Title page 4, in column 1, under "Other Publications", line 1, delete "inimunostimulatory" and insert --immunostimulatory--, therefor On Title page 4, in column 1, under "Other Publications", line 4, delete "imidazoguinoline" and insert --imidazoquinoline--, therefor On Title page 4, in column 1, under "Other Publications", line 5, delete "down-regulation" and insert --downregulation--, therefor On Title page 4, in column 1, under "Other Publications", line 59, delete "PEFylation" and insert --PEGylation--, therefor

IN THE SPECIFICATION:

In column 1, line 57-58, delete "dioleoylphosphatidyl ethanolamine" and insert --dioleoylphosphatidylethanolamine--, therefor Signed and Sealed this
Ninth Day of December, 2014

Michelle K. Lee
*Deputy Director of the United States Patent and Trademark Office*

CERTIFICATE OF CORRECTION (continued)

In column 3, line 65, delete "X'," and insert --$X^1$,--, therefor

In column 6, line 59, delete "(Ig)" and insert --(Ig).--, therefor

In column 8, line 26, after "structures", insert --:--, therefor

In column 8, line 57, delete "structures" and insert --structures:--, therefor

In column 9, equation, line 10, delete " 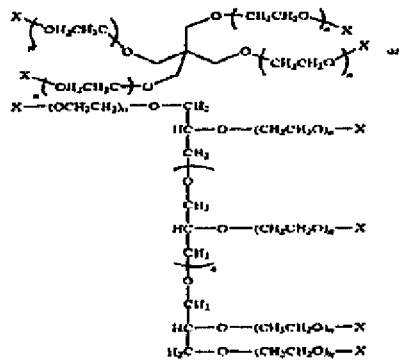 " and insert -- 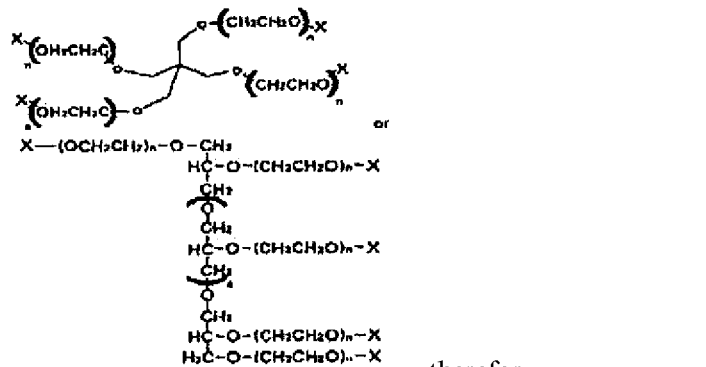 --, therefor In column 9, line 26, delete "propanamido," and insert --propanamide,--, therefor In column 10, line 35, delete "-$CH_2$-$CH_2$-OH" and insert -- -$CH_2$-$CH_2$-OH,--, therefor In column 12, line 7, delete "NR'2," and insert --NR'$_2$,--, therefor In column 14, line 44-45, delete "cyclopropan-1" and insert --cyclopropane-1--, therefor In column 14, line 54, delete "R2" and insert --$R^2$--, therefor In column 14, line 56, delete "R2" and insert --$R^2$--, therefor In column 15, line 49-50, delete "1,3 dihydrobenzomidazol 2 one," and insert --1,3-dihydrobenzomidazol-2-one,--, therefor In column 17, line 7, delete "intravesicularly." and insert --intravesicular.--, therefor CERTIFICATE OF CORRECTION (continued)
U.S. Pat. No. 8,729,088 B2

In column 18, line 42, delete "impregnate" and insert --impregnated--, therefor

In column 20, line 38, delete "automimmune" and insert --autoimmune--, therefor

In column 20, line 54, delete "greata" and insert --areata--, therefor

In column 22, line 5, delete "Ccoronaviridae" and insert --coronaviridae--, therefor In column 22, line 7, delete "eethyma" and insert --ecthyma--, therefor In column 22, line 13, delete "oaramyxoviridae" and insert --paramyxoviridae--, therefor In column 22, line 27, delete "baloon" and insert --balloon--, therefor In column 22, line 40, delete "morphologic" and insert --morphological--, therefor In column 23, line 42, delete "Endopoint" and insert --Endpoint--, therefor In column 23, line 64, delete "DISCOVERY" and insert --DISCOVERY®--, therefor In column 24, line 45, delete "MgSO4" and insert --$MgSO_4$--, therefor In column 25, line 45, delete "t-butanol:H2O" and insert --t-butanol:$H_2O$--, therefor In column 25, line 47-48, delete "t-butanol;H2O" and insert --t-butanol:$H_2O$--, therefor In column 25, line 51, delete "H2O" and insert --$H_2O$--, therefor In column 26, line 46, delete "Raw264.7" and insert --RAW264.7--, therefor In column 26, line 58, delete "CO2" and insert --$CO_2$--, therefor In column 26, line 65, delete "FIG." and insert --FIGS.--, therefor In column 27, line 4, delete "FIG." and insert --FIGS.--, therefor In column 27, line 34, delete "FIG." and insert --FIGS.--, therefor In column 27, line 46, delete "TNF-α In" and insert --TNF-α) in--, therefor In column 27, line 48, delete "FIG." and insert --FIGS.--, therefor In column 28, line 35, delete "spleenocytes" and insert --splenocytes--, therefor In column 28, line 36, delete "spleenocyte" and insert --splenocyte--, therefor

CERTIFICATE OF CORRECTION (continued)
U.S. Pat. No. 8,729,088 B2

In column 28, line 51, delete "spleenocytes," and insert --splenocytes,--, therefor In column 28, line 56-57, delete "spleenocytes" and insert --splenocytes--, therefor In column 29, line 14, delete "haematocytometer" and insert --haemocytometer--, therefor In column 29, line 42, delete "them)" and insert --them).--, therefor In column 30, line 20-21, delete "3990-(2007))." and insert --3990-5 (2007)).--, therefor In column 30, line 53, delete "FIG." and insert --FIGS.--, therefor In column 30, line 61, delete "(FIG." and insert --(FIGS.--, therefor In column 31, line 50, delete "anorexic" and insert --anorexia--, therefor In column 32, line 8, delete "spleenocytes" and insert --splenocytes--, therefor In column 34, line 35, delete "(FIG." and insert --(FIGS.--, therefor In column 34, line 37, delete "(FIG." and insert --(FIGS.--, therefor In column 34, line 39, delete "(FIG." and insert --(FIGS.--, therefor In column 34, line 47, delete "(FIG." and insert --(FIGS.--, therefor In column 34, line 50, delete "(FIG." and insert --(FIGS.--, therefor In column 34, line 61, delete "(FIG." and insert --(FIGS.--, therefor In column 36, line 1, delete "Type1" and insert --Type 1--, therefor In column 41, line 28, delete "anti☐viral" and insert --antiviral--, therefor In column 41, line 29, delete "TLR7MyD88" and insert --TLR7 MyD88--, therefor

IN THE CLAIMS:

In column 44, line 54, in Claim 1, delete "atoms," and insert --atoms--, therefor In column 44, line 56, in Claim 1, delete "-$(R^4)_s$;" and insert --$(R^4)_s)_p$;--, therefor In column 44, line 61-62, in Claim 1, delete "-C(O)NH-$(CH_2)_t$-;" and insert -- -C(O)NH-$(CH_2)_t$-, where t is 1, 2, 3, or 4;--, therefor

CERTIFICATE OF CORRECTION (continued)
U.S. Pat. No. 8,729,088 B2

In column 44, line 67, in Claim 1, delete "-COOR'," and insert -- -COOR$^1$,--, therefor In column 45, line 2, in Claim 1, delete "COOR'," and insert --COOR$^1$,--, therefor In column 45, line 9, in Claim 1, delete "2,3," and insert --2, 3,--, therefor In column 46, line 2, in Claim 12, after "alkoxy", insert --,--, therefor In column 46, line 22, in Claim 17, delete "ethane disulfonic," and insert --ethanedisulfonic,--, therefor

UNITED STATES PATENT AND TRADEMARK OFFICE
CERTIFICATE OF CORRECTION

PATENT NO. : 8,729,088 B2 Page 1 of 1
APPLICATION NO. : 12/704343
DATED : May 20, 2014
INVENTOR(S) : Carson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 572 days.

Signed and Sealed this
Thirtieth Day of May, 2017

Michelle K. Lee
*Director of the United States Patent and Trademark Office*

UNITED STATES PATENT AND TRADEMARK OFFICE
CERTIFICATE OF CORRECTION

PATENT NO. : 8,729,088 B2
APPLICATION NO. : 12/704343
DATED : May 20, 2014
INVENTOR(S) : Carson et al.

Page 1 of 1

It is certified that error appears in the above-identified patent and that said Letters Patent is hereby corrected as shown below:

In the Claims

In Column 44, Line 56, in Claim 1, delete "-$X^2$- (($R^3$)$_r$-($R^4$)$_s$);" and insert -- -$X^2$ - (($R^3$)$_r$ - ($R^4$)$_s$)$_p$;-- therefor Signed and Sealed this
Twenty-eighth Day of April, 2020

Andrei Iancu
*Director of the United States Patent and Trademark Office*